US012673046B2

(12) United States Patent
Fuchss et al.

(10) Patent No.: US 12,673,046 B2
(45) Date of Patent: Jul. 7, 2026

(54) SUBSTITUTED TETRAZOLES AS ACSS2 INHIBITORS

(71) Applicants: Merck Patent GmbH, Darmstadt (DE); RYVU THERAPEUTICS S.A., Cracow (PL)

(72) Inventors: Thomas Fuchss, Darmstadt (DE); Lisa Koetzner, Darmstadt (DE); Christina Schindler, Darmstadt (DE); Daniel Kuhn, Darmstadt (DE)

(73) Assignees: MERCK PATENT GMBH, Darmstadt (DE); RYVU THERAPEUTICS S.A., Krawkow (PL)

( * ) Notice: Subject to any disclaimer, the term of this patent is extended or adjusted under 35 U.S.C. 154(b) by 644 days.

(21) Appl. No.: 17/906,600

(22) PCT Filed: Mar. 16, 2021

(86) PCT No.: PCT/EP2021/056601
§ 371 (c)(1),
(2) Date: Sep. 16, 2022

(87) PCT Pub. No.: WO2021/185793
PCT Pub. Date: Sep. 23, 2021

(65) Prior Publication Data

| | |
|---|---|
| US 2023/0149371 A1 | May 18, 2023 |
| US 2024/0009175 A9 | Jan. 11, 2024 |
| US 2024/0382468 A2 | Nov. 21, 2024 |

(30) Foreign Application Priority Data

Mar. 19, 2020 (EP) .................................... 20164206

(51) Int. Cl.

| | |
|---|---|
| ***A61K 31/41*** | (2006.01) |
| ***A61K 9/02*** | (2006.01) |
| ***A61K 9/06*** | (2006.01) |
| ***A61K 9/08*** | (2006.01) |
| ***A61K 9/19*** | (2006.01) |
| ***A61K 9/20*** | (2006.01) |
| ***A61K 9/28*** | (2006.01) |
| ***A61K 9/48*** | (2006.01) |
| ***A61K 31/437*** | (2006.01) |
| ***A61K 31/444*** | (2006.01) |
| ***A61K 31/501*** | (2006.01) |
| ***A61K 31/506*** | (2006.01) |
| ***A61K 41/17*** | (2020.01) |
| ***A61K 47/02*** | (2006.01) |
| ***A61K 47/44*** | (2017.01) |
| ***C07D 257/04*** | (2006.01) |
| ***C07D 471/04*** | (2006.01) |

(52) U.S. Cl.
CPC .............. *A61K 31/437* (2013.01); *A61K 9/02* (2013.01); *A61K 9/06* (2013.01); *A61K 9/08* (2013.01); *A61K 9/19* (2013.01); *A61K 9/2013* (2013.01); *A61K 9/2059* (2013.01); *A61K 9/2813* (2013.01); *A61K 9/2826* (2013.01); *A61K 9/286* (2013.01); *A61K 9/4825* (2013.01); *A61K 31/444* (2013.01); *A61K 31/501* (2013.01); *A61K 31/506* (2013.01); *A61K 41/17* (2020.01); *A61K 47/02* (2013.01); *A61K 47/44* (2013.01); *C07D 471/04* (2013.01); *C07B 2200/05* (2013.01)

(58) Field of Classification Search
CPC .............................. A61K 31/41; C07D 257/04
USPC .......................................... 514/381; 548/250
See application file for complete search history.

(56) References Cited

FOREIGN PATENT DOCUMENTS

| | | |
|---|---|---|
| JP | 2022538767 A | 7/2023 |
| JP | 2023518285 A | 10/2023 |
| WO | 2015/175845 | 11/2015 |
| WO | 2019067528 A1 | 4/2019 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — EMD SERONO RESEARCH INSTITUTE

(57) ABSTRACT

Substituted tetrazoles of formula I-a, I-b, or I-c:

(I-a)

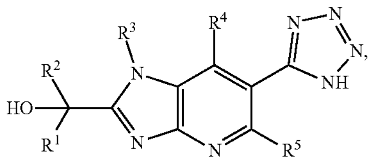

(I-b)

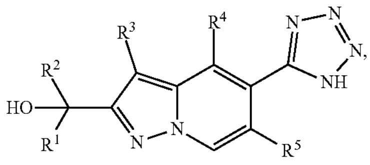

or (I-c)

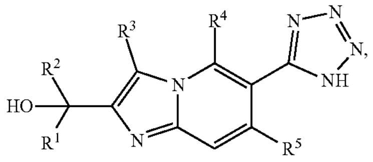

or a pharmaceutically acceptable salt, deuteroisotope, stereoisomer or tautomer thereof; useful as ACSS2 inhibitors are provided.

26 Claims, No Drawings

(56) References Cited

FOREIGN PATENT DOCUMENTS

WO 2020/252407 12/2020
WO WO-2021185793 A1 * 9/2021 ........... A61K 31/437

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Hackam, et al. JAMA, 296(14), 2006, 1731-1732.*
International Search Report dated May 3, 2021, in PCT/EP2021/056601, 3 pages.
Schug et al., "Acetyl-CoA Synthetase 2 Promotes Acetate Utilization and Maintains Cancer Cell Growth under Metabolic Stress", Cancer Cell, vol. 27, Jan. 12, 2015, pp. 57-71.
Schug et al., "The metabolic fate of acetate in Cancer", Nature Reviews—Cancer, vol. 16, Nov. 2016, pp. 708-717.
Written Opinion dated May 3, 2021, in PCT/EP2021/056601, 6 pages.
Sabnis, ACS Med. Chem. Lett., 2021, 12, 1894-1895.
Foster, Allanb. , "Deuterium isotope effects in the metabolism of drugs and xenobiotics: implications for drug design", Advances in Drug Research, vol. 14, 1986, pp. 1-40.
Gillette, et al., "Theory for the observed isotope effects on the formation of multiple products by different kinetic mechanisms of cytochrome P450 enzymes", Biochemistry, vol. 33, No. 10, Mar. 15, 1994, pp. 2927-2937.
Hanzlik, et al., "Active site dynamics of toluene hydroxylation by cytochrome p. 450", The Journal of Organic Chemistry, vol. 55, No. 13, Jun. 1, 1990, pp. 3992-3997.
Jarman, et al., "The deuterium isotope effect for the α-hydroxylation of tamoxifen by rat liver microsomes accounts for the reduced genotoxicity of [D5-ethyl]tamoxifen", Carcinogenesis, vol. 16, No. 4, Apr. 1, 1995, pp. 683-688.
"International Preliminary Report on Patentability received for PCT Application No. PCT/EP2021/056601, mailing date Sep. 29, 2022", 08 Pages.
Reider, et al., "Synthesis of (R)-serine-2-d and its conversion to the broad-spectrum antibiotic fludalanine", The Journal of Organic Chemistry, vol. 52, No. 15, Jul. 1, 1987, pp. 3326-3334.

* cited by examiner

SUBSTITUTED TETRAZOLES AS ACSS2 INHIBITORS

CROSS-REFERENCE TO RELATED APPLICATIONS

This application is the National Stage entry under § 371 of International Application No. PCT/EP2021/056601, filed on Mar. 16, 2021, and which claims the benefit of priority to European Application No. 20164206.3, filed on Mar. 19, 2020. The content of each of these applications is hereby incorporated by reference in its entirety.

BACKGROUND OF THE INVENTION

Field of the Invention

The present invention relates to substituted tetrazole derivatives. These compounds are useful for inhibiting acetyl-CoA synthetase 2 (ACSS2) and for the prevention and/or treatment of several medical conditions including hyperproliferative disorders and diseases that are affected by ACSS2 activity.

Description of Related Art

It is well established that the rapid and uncontrolled growth of tumors and proliferation of cancer cells require increased energy (ATP) and biomass (lipids) production when compared to normal, healthy cells.

In recent years the role of acetate metabolism for cancer cell proliferation has become of growing interest in cancer research and the development of cancer therapy. It has been shown that some tumors primarily utilize acetate for energy production, while others mainly use it for lipid (i.e. biomass) synthesis or regulation of histone acetylation and thus gene transcription (Z. T. Schug, et al., Nature Reviews Cancer 16, 707-717 (2016)). In all these processes acetate is converted into acetyl-CoA by means of acetyl-CoA synthetase, ACSS, etiher by the mitochondria-localized ACSS1 or the nucleo-cytosol-localized ACSS2. Thus, acetyl-CoA is an important metabolite of cancer cells not only with regard to energy production in the mitochondrion but also with regard to lipid and fatty acid synthesis in the cytosol of cancer cells as well as the histone acetylation in the nucleus of the cell.

Studies have shown that in particular ACSS2 is highly expressed in many cancer tissues. These findings and the fact that it is upregulated by hypoxia and low nutrient availability make ACSS2 an attractive target for cancer treatment (Z. T. Schug, et al., Cancer Cell (2015) 27, 57-71; Z. T. Schug, et al., Nature Reviews Cancer 16, 707-717 (2016)).

WO 2015/175845 A1 discloses certain benzimidazole derivatives as inhibitors of ACSS2.

WO 2020/252407 A1 discloses certain benzimidazole derivatives as inhibitors of ACSS2.

SUMMARY OF THE INVENTION

It is an object of the present invention to provide compounds that are useful for the prevention and/or treatment of medical conditions, disorders and/or diseases, in particular of hyperproliferative disorders/diseases, which compounds are inhibitors of ACSS2.

The object has surprisingly been solved by the compounds of the present invention. This invention provides a tetrazole derivative of formula I-a, I-b or I-c

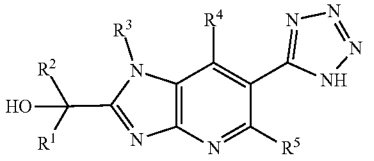

(I-a)

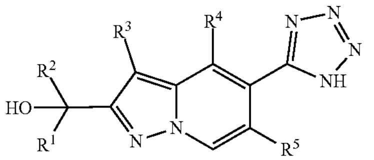

(I-b)

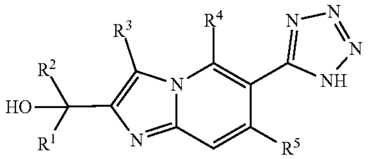

(I-c)

wherein independently from each other $R^1$ denotes $Ar^A$ or $Hetar^A$;

$R^2$ denotes $Ar^B$ or $Hetar^B$ $R^3$ denotes $C_{1-6}$-aliphatic or —O—$C_{1-6}$-aliphatic;

$R^4$ denotes H, D, $C_{1-6}$-aliphatic or —O—$C_{1-6}$-aliphatic;

$R^5$ denotes H, D, $C_{1-6}$-aliphatic, —O—$C_{1-6}$-aliphatic or halogen;

$Ar^A$ is a mono- or biaryl with 5, 6, 7, 8, 9, 10, 11 ring carbon atoms, wherein that aryl may be unsubstituted or substituted with substituents $R^{A1}$, $R^{A2}$, $R^{A3}$, $R^{A4}$ and/or $R^{A5}$ which may be the same or different;

$Ar^B$ is a mono- or biaryl with 5, 6, 7, 8, 9, 10, 11 ring carbon atoms, wherein that aryl may be unsubstituted or substituted with substituents $R^{B1}$, $R^{B2}$, $R^{B3}$, $R^{B4}$ and/or $R^{B5}$ which may be the same or different;

$Hetar^A$ is a mono- or bicyclic heteroaryl with 5, 6, 7, 8, 9, 10, 11 ring atoms wherein 1, 2, 3, 4, 5 of said ring atoms is/are a hetero atom(s) selected from N, O and/or S and the remaining are carbon atoms, wherein that heteroaryl may be unsubstituted or substituted with substituents $R^{A1}$, $R^{A2}$, $R^{A3}$, $R^{A4}$ and/or $R^{A5}$ which may be the same or different;

$Hetar^B$ is a mono- or bicyclic heteroaryl with 5, 6, 7, 8, 9, 10, 11 ring atoms wherein 1, 2, 3, 4, 5 of said ring atoms is/are a hetero atom(s) selected from N, O and/or S and the remaining are carbon atoms, wherein that heteroaryl may be unsubstituted or substituted with substituents $R^{B1}$, $R^{B2}$, $R^{B3}$, $R^{B4}$ and/or $R^{B5}$ which may be the same or different;

$R^{A1}$, $R^{A2}$, $R^{A3}$, $R^{A4}$, $R^{A5}$, $R^{B1}$, $R^{B2}$, $R^{B3}$, $R^{B4}$, $R^{B5}$ are independently from each other H, D, halogen, $C_{1-6}$-aliphatic, —O—$C_{1-6}$-aliphatic;

halogen denotes F, Cl, Br or I;

or any derivative, any N-oxide, prodrug, solvate, tautomer or stereoisomer thereof and/or any pharmaceutically acceptable salt of each of the foregoing, including mixtures thereof in all ratios.

DETAILED DESCRIPTION OF THE INVENTION

In general, all residues, radicals, substituents, groups, moieties, etc. which occur more than once may be identical or different, i.e. are independent of one another. Above and below, the residues and parameters have the meanings indicated for formula I-a, I-b or I-c, unless expressly indicated otherwise. Accordingly, the invention relates, in particular, to the compounds of formula I-a, I-b or I-c in which at least one of the said residues, radicals, substituents has one of the preferred meanings indicated below.

Any of those particular or even preferred embodiments of the present invention as specified below do not only refer to the specified compounds of formula I-a, I-b or I-c but to derivatives, N-oxides, prodrugs, solvates, tautomers or stereoisomers thereof as well as the pharmaceutically acceptable salts of each of the foregoing, including mixtures thereof in all ratios, too, unless indicated otherwise.

In a particular embodiment, PE1, the compound of the present invention is a tetrazole of formula I-a, I-b or I-c, or any derivative, N-oxide, prodrug, solvate, tautomer or stereoisomer thereof and/or any pharmaceutically acceptable salt of each of the foregoing, including mixtures thereof in all ratios, in which $R^1$ and $R^2$ have the same meaning. This means that, for instance, if $R^1$ denotes $Ar^A$, then $R^2$ denotes $Ar^B$ which in turn denotes the same $Ar^A$ as for $R^1$, i.e. it is the same substituent; likewise, if $R^1$ denotes $Hetar^A$, then $R^2$ means $Hetar^B$ which in turn means the same $Hetar^A$ as for $R^1$ (i.e. it is the same substituent).

A further particular embodiment of the present invention, designated as PE2, is a tetrazole of formula I-a, I-b or I-c, or any derivative, N-oxide, prodrug, solvate, tautomer or stereoisomer thereof and/or any pharmaceutically acceptable salt of each of the foregoing, including mixtures thereof in all ratios, in which $R^1$ and $R^2$ have a different meaning. In this embodiment the substituents $R^1$ and $R^2$ are chosen to be non-identical. For instance, if $R^1$ denotes 2-methylphenyl (i.e., $Ar^A$ is a monocyclic 6-membered aromatic ring and one of the substituents $R^{A1}$, $R^{A2}$, $R^{A3}$, $R^{A4}$ and/or $R^{A5}$ being methyl in 2-position relative to the point of connection of $Ar^A$ with the hydroxy-substituted carbon atom to which it is attached while the others are hydrogen), then $R^2$ may be $Hetar^B$ as defined herein or $Ar^B$ except for 2-methylphenyl.

It has to be recognized that any tetrazole derivative of PE2 has a chiral center at the carbon atom that bears the different substituents $R^1$ and $R^2$ as this carbon atom will then be substituted with four different substituents.

In still another particular embodiment of the invention, designated as PE3, the tetrazole derivative of the present invention is a tetrazole of formula I-a, I-b or I-c, or any derivative, N-oxide, prodrug, solvate, tautomer or stereoisomer thereof and/or any pharmaceutically acceptable salt of each of the foregoing, including mixtures thereof in all ratios, in which both substituents $R^1$ and $R^2$ are independently from each other monocyclic rings, i.e.

- $Ar^A$ is phenyl which may be unsubstituted or mono-, di-, tri-, tetra- or pentasubstituted with $R^{A1}$, $R^{A2}$, $R^{A3}$, $R^{A4}$, $R^{A5}$;
- $Ar^B$ is phenyl which may be unsubstituted or mono-, di-, tri-, tetra- or pentasubstituted with $R^{B1}$, $R^{B2}$, $R^{B3}$, $R^{B4}$, $R^{B5}$;
- $Hetar^A$ is a monocyclic heteroaryl with 5 or 6 ring atoms wherein 1 or 2 of said ring atoms is/are a hetero atom(s) selected from N, O and/or S and the remaining are carbon atoms, wherein that heteroaryl may be unsubstituted or mono-, di-, tri-, tetra- or pentasubstituted with $R^{A1}$, $R^{A2}$, $R^{A3}$, $R^{A4}$, $R^{A5}$;
- $Hetar^B$ is a monocyclic heteroaryl with 5 or 6 ring atoms wherein 1 or 2 of said ring atoms is/are a hetero atom(s) selected from N, O and/or S and the remaining are carbon atoms, wherein that heteroaryl may be unsubstituted or mono-, di-, tri-, tetra- or pentasubstituted with $R^{B1}$, $R^{B2}$, $R^{B3}$, $R^{B4}$, $R^{B5}$;
- wherein $R^{A1}$, $R^{A2}$, $R^{A3}$, $R^{A4}$, $R^{A5}$ may be the same or different; and $R^{B1}$, $R^{B2}$, $R^{B3}$, $R^{B4}$, $R^{B5}$ may be the same or different.

If $R^1$ and $R^2$ are identical, i.e. have the same meaning, then this PE3 is also within the scope of PE1. Likewise, if $R^1$ and $R^2$ do not have the same meaning, this PE3 is within the scope of PE2.

In a preferred particular embodiment, PE3a, of PE3

- $Ar^A$ is phenyl which may be unsubstituted or mono- or di-substituted with $R^{A1}$ and/or $R^{A2}$;
- $Ar^B$ is phenyl which may be unsubstituted or mono- or di-substituted with $R^{B1}$ and/or $R^{B2}$;
- $Hetar^A$ is a monocyclic heteroaryl with 5 or 6 ring atoms wherein 1 or 2 of said ring atoms is/are a hetero atom(s) selected from N, O and/or S and the remaining are carbon atoms, wherein that heteroaryl may be unsubstituted or substituted with substituents $R^{A1}$ and/or $R^{A2}$ which may be the same or different;
- $Hetar^B$ is a monocyclic heteroaryl with 5 or 6 ring atoms, wherein 1 or 2 of said ring atoms is/are a hetero atom(s) selected from N, O and/or S and the remaining are carbon atoms, wherein that heteroaryl may be unsubstituted or substituted with substituents $R^{B1}$ and/or $R^{B2}$ which may be the same or different.

In still another preferred particular embodiment, PE3b, of PE3a

- $R^{A1}$, $R^{A2}$, $R^{B1}$, $R^{B2}$ are independently from each other H, F, Cl, $C_{1-4}$-aliphatic, —O—$C_{1-4}$-aliphatic.

If in PE3a substituent $Ar^A$ being phenyl is mono-substituted with substituent $R^{A1}$ or $R^{A2}$, then this substituent $R^{A1}$ or $R^{A2}$ is preferably located in 2-position or 4-position of the phenyl ring. If that phenyl ring $Ar^A$ is di-substituted with $R^{A1}$ and $R^{A2}$, then these two substituents, which may be the same or different, are preferably in 2- and 4-position of that phenyl ring.

Likewise, if in PE3a substituent $Ar^B$ being phenyl is mono-substituted with substituent $R^{B1}$ or $R^{B2}$, then this substituent $R^{B1}$ or $R^{B2}$ is preferably located in 2-position or 4-position of the phenyl ring. If that phenyl ring $Ar^B$ is di-substituted with $R^{B1}$ and $R^{B2}$, then these two substituents, which may be the same or different, are preferably in 2- and 4-position of that phenyl ring.

In still another particular embodiment, PE4, the tetrazole derivative of the present invention is a tetrazole of formula I-a, I-b or I-c, or any derivative, N-oxide, prodrug, solvate, tautomer or stereoisomer thereof and/or any pharmaceutically acceptable salt of each of the foregoing, including mixtures thereof in all ratios, in which independently from each other

- $R^3$ denotes $C_{1-4}$-alkyl, preferably $C_{1-2}$-alkyl which is unsubstituted or mono-substituted with —OH or —$NH_2$;
- $R^4$ denotes H;
- $R^5$ denotes H, $C_{1-4}$-alkyl, —O—$C_{1-4}$-alkyl, F or Cl; preferably H, $C_{1-2}$-alkyl, —O—$C_{1-2}$-alkyl, F or Cl;
- and wherein the remaining radicals, residues, groups or substituents are as defined for the formulas I-a, I-b and I-c above in general or for any other particular embodiments mentioned above, i.e. PE1, PE2, PE3, PE3a, PE3b.

In still another particular embodiment, PE5, the tetrazole derivative of the present invention is a tetrazole of formula I-a, I-b or I-c, or any derivative, N-oxide, prodrug, solvate, tautomer or stereoisomer thereof and/or any pharmaceutically acceptable salt of each of the foregoing, including mixtures thereof in all ratios, in which independently from each other $R^1$ denotes $Ar^A$ or $Hetar^A$;

$R^2$ denotes $Ar^B$ or $Hetar^B$;

$R^3$ denotes methyl, ethyl, 2-aminoethyl or 2-hydroxyethyl:

$R^4$ denotes H;

$R^5$ denotes H, methyl, ethyl, methoxy, F or Cl;

$Ar^A$ is phenyl; deuterophenyl, preferably pentadeuterophenyl; flurophenyl, preferably 2-fluorophenyl; methylphenyl (tolyl), preferably 2-methylphenyl; difluoromethoxy, preferably 4-difluoromethoxy; 4-difluoromethoxy-2-fluorophenyl;

$Ar^B$ phenyl; deuterophenyl, preferably pentadeuterophenyl; flurophenyl, preferably 2-fluorophenyl; methylphenyl (tolyl), preferably 2-methylphenyl; difluoromethoxy, preferably 4-difluoromethoxy; 4-difluoromethoxy-2-fluorophenyl;

$Hetar^A$ methylpyrazolyl, preferably 1-methlypyrazl-3-yl, 1-methylpyrazol-4-yl; thien-2-yl, thien-3-yl; methylthienyl, preferably 5-methylthien-2-yl; thiazolyl, preferably 1,3-thiazol-2-yl; pyridin-2-yl, pyridin-3-yl, pyridin-4-yl; pyrimidinyl, preferably pyrimidin-2-yl, pyrimidin-4-yl; pyridazinyl, preferably pyridazin-3-yl;

$Hetar^B$ methylpyrazolyl, preferably 1-methlypyrazl-3-yl, 1-methylpyrazol-4-yl; thien-2-yl, thien-3-yl; methylthienyl, preferably 5-methylthien-2-yl; thiazolyl, preferably 1,3-thiazol-2-yl; pyridin-2-yl, pyridin-3-yl, pyridin-4-yl; pyrimidinyl, preferably pyrimidin-2-yl, pyrimidin-4-yl; pyridazinyl, preferably pyridazine-3-yl.

If $R^1$ and $R^2$ are identical, i.e. have the same meaning, then this is another particular embodiment PE5a of PE5. Likewise, if $R^1$ and $R^2$ do not have the same meaning, this is yet another particular embodiment PE5b of PE5.

In yet another particular embodiment, PE6, the tetrazole derivative of the present invention is selected from a compound of formula I-a (i.e. 1H-imidazo[4,5-b]pyridine derivatives), or any derivative, N-oxide, prodrug, solvate, tautomer or stereoisomer thereof and/or any pharmaceutically acceptable salt of each of the foregoing, including mixtures thereof in all ratios, in which $R^1$, $R^2$, $R^3$, $R^4$ and $R^5$ are as defined previously in the description or for any of the particular embodiments PE1, PE2, PE3, PE3a, PE3b, PE4, PE5, PE5a, PE5b.

In a specific particular embodiment, PE6a, of PE6

$R^1$ denotes phenyl, 2-methylphenyl, 2-fluorophenyl, 1-methylpyrazol-4-yl, thien-2-yl, thien-3-yl, 1,3-thiazol-2-yl, pyridin-2-yl, pyridin-3-yl, pyridin-4-yl; pyrimidin-2-yl, pyrimidin-4-yl, pyridazine-3-yl, 4-difluoromethoxy; 4-difluoromethoxy-2-fluorophenyl;

$R^2$ denotes phenyl, 2-methylphenyl, 2-fluorophenyl, thien-2-yl, thien-3-yl;

$R^3$ denotes methyl, ethyl, 2-aminoethyl, 2-hydroxyethyl; preferably methyl or ethyl;

$R^4$ H;

$R^5$ H, methyl, methoxy, Cl; preferably methoxy.

In another specific particular embodiment, PE6b, of PE6 or PE6a $R^1$ and $R^2$ are the same. In another specific particular embodiment, PE6c, of PE6 or PE6a $R^1$ and $R^2$ are different.

In yet another particular embodiment, PE7, the tetrazole derivative of the present invention is selected from a compound of formula I-b (i.e. pyrazolo[1,5]a]pyridine derivatives), or any derivative, N-oxide, prodrug, solvate, tautomer or stereoisomer thereof and/or any pharmaceutically acceptable salt of each of the foregoing, including mixtures thereof in all ratios, in which $R^1$, $R^2$, $R^3$, $R^4$ and $R^5$ are as defined previously in the description or for any of the particular embodiments PE1, PE2, PE3, PE3a, PE3b, PE4, PE5, PE5a, PE5b.

In a specific particular embodiment, PE7a, of PE7

$R^1$ denotes phenyl, 2-fluorophenyl;

$R^2$ denotes phenyl, 2-fluorophenyl;

$R^3$ denotes ethyl;

$R^4$ H;

$R^5$ H, methoxy, F, Cl.

In another specific particular embodiment, PE7b, of PE7 or PE7a $R^1$ and $R^2$ are the same. In another specific particular embodiment, PE7c, of PE7 or PE7a $R^1$ and $R^2$ are different.

In yet another particular embodiment, PE8, the tetrazole derivative of the present invention is selected from a compound of formula I-c (i.e. imidazo[1,2-a]pyridine derivatives), or any derivative, N-oxide, prodrug, solvate, tautomer or stereoisomer thereof and/or any pharmaceutically acceptable salt of each of the foregoing, including mixtures thereof in all ratios, in which $R^1$, $R^2$, $R^3$, $R^4$ and $R^5$ are as defined previously in the description or for any of the particular embodiments PE1, PE2, PE3, PE3a, PE3b, PE4, PE5, PE5a, PE5b.

In a specific particular embodiment, PE8a, of PE8

$R^1$ denotes phenyl, 2-fluorophenyl, 1-methlypyrazol-3-yl, 5-methylthien-2-yl, 1,3-thiazol-2-yl, pyridin-2-yl, pyrimidin-2-yl;

$R^2$ denotes phenyl, 2-fluorophenyl;

$R^3$ denotes ethyl;

$R^4$ H;

$R^5$ ethyl, methoxy, F, Cl; preferably methoxy.

In another specific particular embodiment, PE8b, of PE8 or PE8a $R^1$ and $R^2$ are the same. In another specific particular embodiment, PE8c, of PE8 or PE8a $R^1$ and $R^2$ are different.

In still another particular embodiment, PE9, the tetrazole of formula I-a, I-b or I-c, is selected from the group consisting of the compounds shown in Table 1 which is divided in Tables 1a, 1b, 1c, 1d, 1e, 1f, 1g, 1h, 1i and 1j as well as any derivative, any N-oxide, prodrug, solvate, tautomer or stereoisomer thereof and/or any pharmaceutically acceptable salt of each of the foregoing, including mixtures thereof in all ratios.

As used herein, the following definitions shall apply unless otherwise indicated or defined specifically elsewhere in the description for specific substituents, radicals, residues, groups or moieties.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon or tricyclic hydrocarbon that is completely saturated or that contains one or more units of unsaturation, such as one or more C═C double bond(s) and/or C≡C triple bond(s), but which is not aromatic (also referred to herein as "carbocycle", "cycloaliphatic" or "cycloalkyl"), that has—in general and if not defined otherwise in this specification—a single point of attachment to the rest of the molecule. Unless otherwise specified, aliphatic groups contain 1-8 or 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" ("cycloalkyl") refers to a monocyclic $C_3$-$C_7$ hydrocarbon that is completely saturated or that contains one or more units of unsaturation, but which is not aromatic, that has a single point of attachment to the rest of the molecule. In another embodiment the term "carbocycle" refers to a monocyclic or bicyclic cycloaliphatic ring system which is fused to an aromatic, heteroaromatic or heterocyclic ring or ring system via 2 adjacent ring atoms of that aromatic, heteroaromatic or heterocyclic ring or ring system; in other words, such carbocycle shares two ring atoms with the ring or ring system to which it is fused thereby having two points of attachement to the rest of the molecule. Suitable aliphatic groups include, but are not limited to, linear or branched, substituted or unsubstituted alkyl, alkenyl, alkynyl groups and hybrids thereof as (cycloalkyl) alkyl, (cycloalkenyl) alkyl or (cycloalkyl) alkenyl.

The term "alkyl" usually refers to a saturated aliphatic and acyclic moiety, while the term "alkenyl" usually refers to an unsaturated alphatic and acyclic moiety with one or more C═C double bonds and the term "alkynyl" usually refers to an aliphatic and acyclic moiety with one or more C≡C triple bonds. Exemplary aliphatic groups are linear or branched, substituted or unsubstituted $C_{1-8}$-alkyl, $C_{1-6}$-alkyl, $C_{1-4}$-alkyl, $C_{2-8}$-alkenyl, $C_{2-6}$-alkenyl, $C_{2-8}$-alkynyl, $C_{2-6}$-alkynyl groups and hybrids thereof such as (cycloalkyl)alkyl, (cycloalkenyl)alkyl or (cycloalkyl)alkenyl.

In particular, the term "$C_{1-3}$-alkyl" refers to alkyl groups, i.e. saturated acyclic aliphatic groups, having 1, 2 or 3 carbon atoms. Exemplary $C_{1-3}$-alkyl groups are methyl, ethyl, propyl and isopropyl. The term "$C_{1-4}$-alkyl" refers to alkyl groups having 1, 2, 3 or 4 carbon atoms. Exemplary $C_{1-4}$-alkyl groups are methyl, ethyl, propyl, isopropyl, butyl, isobutyl, and tert-butyl. The term "$C_{1-6}$-alkyl" refers to alkyl groups having 1, 2, 3, 4, 5 or 6 carbon atoms. Exemplary $C_{1-6}$-alkyl groups are methyl, ethyl, propyl, isopropyl, butyl, isobutyl, tert-butyl, n-pentyl, 2-pentyl, n-hexyl, and 2-hexyl. The term "$C_{1-8}$-alkyl" refers to alkyl groups having 1, 2, 3, 4, 5, 6, 7, or 8 carbon atoms. Exemplary $C_{1-8}$-alkyl groups are methyl, ethyl, propyl, isopropyl, butyl, isobutyl, tert-butyl, n-pentyl, 2-pentyl, n-hexyl, 2-hexyl n-heptyl, 2-heptyl, n-octyl, 2-octyl, and 2,2,4-trimethylpentyl. Each of these alkyl groups may be straight-chain or—except for $C_1$-alkyl and $C_2$-alkyl—branched and may be unsubstituted or substituted with 1, 2 or 3 substituents that may be the same or different and are, if not specified differently elsewhere in this specification, selected from the group comprising halogen, hydroxy, alkoxy, unsubstituted or mono- or di-substituted amino.

In some instances the $C_{1-3}$-alkyl, $C_{1-4}$-alkyl, $C_{1-6}$-alkyl, $C_{1-8}$-alkyl groups may also comprise those residues in which 1 or 2 of non-terminal and non-adjacent $—CH_2$-(methylene) groups are replaced by —O—, —S— and/or 1 or 2 non-terminal and non-adjacent $—CH_2—$ or —CH— groups are replaced by —NH— or —N—. These replacements yield, for instance, (modified) alkyl groups like $—CH_2—CH_2—O—CH_3$, $—CH_2—CH_2—CH_2—S—CH_3$, $CH_2—CH_2—NH—CH_2—CH_3$, $CH_2—CH_2—O—CH_2—CH_2—O—CH_3$, $CH_2—CH_2—N(CH_3)—CH_2—CH_3$, and the like. Further and/or different replacements of —CH— and $—CH_2—$ groups may be defined for specific alkyl substituents or radicals elsewhere in the description.

The term "$C_{3-7}$-cycloalkyl" refers to a cycloaliphatic hydrocarbon, as defined above, with 3, 4, 5, 6 or 7 ring carbon atoms. $C_{3-7}$-cycloalkyl groups may be unsubstituted or substituted with—unless specified differently elsewhere in this specification—1, 2 or 3 substituents that may be the same of different and are—unless specified differently elsewhere in this specification—selected from the group comprising $C_{1-6}$-alkyl, $O—C_{1-6}$-alkyl (alkoxy), halogen, hydroxy, unsubstituted or mono- or di-substituted amino. Exemplary $C_{3-7}$-cycloalkyl groups are cyclopropyl, 2-methyl-cyclopropyl, cyclopropenyl, cyclobutyl, cyclobutenyl, cyclopentyl, cyclopentenyl, cyclohexyl, cyclohexenyl, cycloheptyl, cycloheptenyl.

The term "aliphatoxy" refers to saturated or unsaturated aliphatic groups or substituents as defined above that are connected to another structural moiety via an oxygen atom (—O—). The term "alkoxy" refers to a particular subgroup of saturated aliphatoxy, i.e. to alkyl substituents and residues that are connected to another structural moiety via an oxygen atom (—O—). Sometimes, it is also referred to as "O-alkyl" and more specifically as "$O—C_{1-4}$-alkyl", "$O—C_{1-6}$-alkyl", "$O—C_{1-8}$-alkyl". Like the similar alkyl groups, it may be straight-chain or—except for $—O—C_1$-alkyl and $—O—C_2$-alkyl—branched and may be unsubstituted or substituted with 1, 2 or 3 substituents that may be the same or different and are, if not specified differently elsewhere in this specification, selected from the group comprising halogen, unsubstituted or mono- or di-substituted amino. Exemplary alkoxy groups are methoxy, trifluoromethoxy, ethoxy, 2,2,2-trifluoroethoxy, n-propoxy, isopropoxy, n-butoxy, sec-butoxy, tert-butoxy, n-pentoxy.

The term "alkylene" refers to a divalent aliphatic group and in particular a divalent alkyl group. An "alkylene chain" is a polymethylene group, i.e., $—(CH_2)_x—$, wherein x is a positive integer, preferably 1, 2, 3, 4, 5 or 6. In the context of the present invention "$C_{1-3}$-alkylene" refers to an alkylene moiety with 1, 2 and 3, respectively, $—CH_2—$ groups; the term "alkylene", however, not only comprises linear alkylene groups, i.e. "alkylene chains", but branched alkylene groups as well. The term "$C_{1-6}$-alkylene" refers to an alkylene moiety that is either linear, i.e. an alkylene chain, or branched and has 1, 2, 3, 4, 5 or 6 carbon atoms. A substituted alkylene chain is a polymethylene group in which one or more methylene hydrogen atoms are replaced by (or with) a substituent. Suitable substituents include those described herein for a substituted alkyl group. In some instances 1 or 2 methylene groups of the alkylene chain may be replaced by, for instance, O, S and/or NH or $N—C_{1-4}$-alkyl. Exemplary alkylene groups are $—CH_2—$, $—CH_2—CH_2—$, $—CH_2—CH_2—CH_2—CH_2—$, $—O—CH_2—O—$, $—O—CH_2—CH_2—O—$, $—O—CH_2—CH_2—CH_2—O—$, $—CH_2—NH—CH_2—CH_2—$, $—CH_2—N(CH_3)—CH_2—CH_2—$.

The term "alkenylene" refers to a bivalent alkenyl group. A substituted alkenylene chain is a polymethylene group containing at least one double bond in which one or more hydrogen atoms are replaced with a substituent. Suitable substituents include those described herein for a substituted aliphatic group.

The term "alkynylene" refers to a bivalent alkynyl group. A substituted alkynylene chain is a polymethylene group containing at least one triple bond in which one or more hydrogen atoms are replaced with a substituent. Suitable substituents include those described herein for a substituted aliphatic group.

The term "halogen" means F, Cl, Br, or I.

The term "heteroatom" means one or more of oxygen (O), sulfur (S), or nitrogen (N), including, any oxidized form of nitrogen or sulfur, e.g. N-oxides, sulfoxides and sulfones; the quaternized form of any basic nitrogen or a substitutable nitrogen of a heterocyclic or heteroaromatic ring, for example N (as in 3,4-dihydro-2H-pyrrolyl), NH (as in pyrrolidinyl) or N-SUB with SUB being a suitable substituent (as in N-substituted pyrrolidinyl).

The term "aryl" used alone or as part of a larger moiety as in "aralkyl", "aralkoxy", or "aryloxyalkyl", refers to monocyclic, bicyclic and tricyclic ring systems having a total of five to fourteen ring members, that ring members being carbon atoms, wherein at least one ring in the system is aromatic, i.e., it has $(4n+2)\pi$ (pi) electrons (with n being an integer selected from 0, 1, 2, 3), which electrons are delocalized over the system, and wherein each ring in the system contains three to seven ring members. Preferably, all rings in the aryl system or the entire ring system are aromatic. The term "aryl" is used interchangeably with the term "aryl ring". In certain embodiments of the present invention, "aryl" refers to an "aromatic ring system". More specifically, those aromatic ring systems may be mono-, bi- or tricyclic with 5, 6, 7, 8, 9, 10, 11, 12, 13, 14 ring carbon atoms. Even more specifically, those aromatic ring systems may be mono- or bicyclic with 6, 7, 8, 9, 10 ring carbon atoms. The term "monoaryl" refers to a monocyclic aryl. The term "biaryl" refers to a bicyclic aryl. Exemplary aryl groups are phenyl, biphenyl, naphthyl, anthracyl and the like, which may be unsubstituted or substituted with one or more identical or different substituents. Also included within the scope of the terms "aryl" or "aromatic ring system", as they are used herein, is a group in which an aromatic ring is fused to one or more non-aromatic rings, such as indanyl, phthalimidyl, naphthimidyl, phenanthridinyl, or tetrahydronaphthyl, and the like. In the latter case the "aryl" group or substituent is attached to its pendant group via the aromatic part of the ring system.

The term "benzo" refers to a six-membered aromatic ring (with carbon ring atoms) that is fused via two adjacent carbon atoms to another ring, being it a cycloaliphatic, aromatic, heteroaromatic or heterocyclic (heteroaliphatic) ring; as a result a ring sytem with at least two rings is formed in which the benzo ring shares two common carbon atoms with the other ring to which it is fused. For example, if a benzo ring is fused to a phenyl ring, a napthaline ring system is formed, while fusing a benzo ring to a pyridine provides for either a quinoline or an isoquinoline.

The terms "heteroaryl" and "heteroar-", used alone or as part of a larger moiety, e.g., "heteroaralkyl", or "heteroaralkoxy", refer to groups having 3, 4, 5, 6, 7, 8, 9, 10, 11, 12, 13, 14 ring atoms (which atoms are carbon and hetero atoms), preferably 5, 6, 9 or 10 ring atoms; having 6, 10, or 14 $\pi$ (pi) electrons shared in a cyclic array; and having, in addition to carbon atoms, 1, 2, 3, 4 or 5 heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, furazanyl, pyridyl (pyridinyl), pyridazinyl, pyrimidinyl, pyrazinyl, indolizinyl, purinyl, naphthyridinyl, pteridinyl, and pyrrolopyridinyl, in particular pyrrolo[2,3-b]pyridinyl. The terms "heteroaryl" and "heteroar-", as used herein, also include groups in which a heteroaromatic ring is fused to one or more aryl, cycloaliphatic, or heterocyclyl rings, where the radical or point of attachment is preferably on the heteroaromatic or, if present, the aryl ring. Nonlimiting examples include indolyl, isoindolyl, benzothienyl (benzothiophenyl), benzofuranyl, dibenzofuranyl, indazolyl, benzimidazolyl, benzothiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, 9H-carbazolyl, dibenzofuranyl and pyrido[2,3-b]-1,4-oxazin-3(4H)-one. For example, an indolyl ring may be attached via one of the ring atoms of the six-membered aryl ring or via one of the ring atoms of the five-membered heteroaryl ring. A heteroaryl group is optionally mono-, bi- or tricyclic. The term "heteroaryl" is used interchangeably with the terms "heteroaryl ring", "heteroaryl group", or "heteroaromatic", any of which terms include rings that are unsubstituted or substituted with one or more identical or different substituents. The term "heteroaralkyl" refers to an alkyl group substituted by a heteroaryl, wherein the alkyl and heteroaryl portions independently are optionally substituted.

A heteroaryl ring can be attached to its pendant group at any of its hetero or carbon ring atoms which attachment results in a stable structure or molecule: any of the ring atoms may be unsubstituted or substituted.

The structures of typical examples of "heteroaryl" substituents as used in the present invention are depicted below:

pyrrolyl

furanyl

thiophenyl

1-oxa-2,3-diazolyl

1-oxa-2,4-diazolyl

1-oxa-3,4-diazolyl

1-oxa-2,5-diazolyl

1-thia-2,3-diazolyl

1-thia-2,4-diazolyl

1-thia-3,4-diazolyl

1-thia-2,5-diazolyl

oxazolyl

isoxazolyl

isothiazolyl

thiazolyl

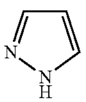
pyrazolyl

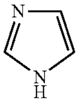
imidazolyl

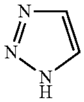
1,2,3-triazolyl

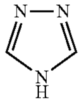
1,3,4-triazolyl

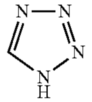
tetrazolyl

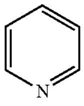
pyridinyl (pyridyl)

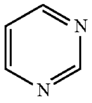
pyrimidinyl

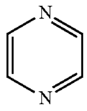
pyrazinyl

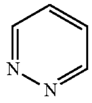
pyridazinyl

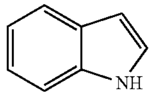
indolyl

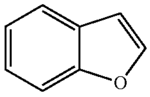
benzofuranyl

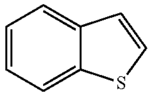
benzothiophenyl

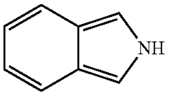
isoindolyl

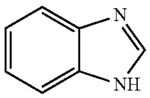
benzimidazolyl

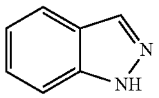
indazolyl

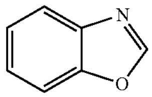
benzoxazolyl

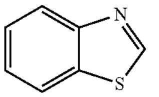
benzothiazolyl

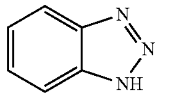
benzotriazolyl

-continued

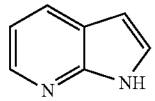
pyrrolo[2,3-b] pyridinyl

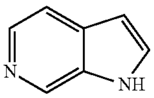
pyrrolo[2,3-c] pyridinyl

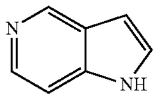
pyrrolo[3,2-c] pyridinyl

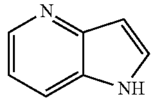
pyrrolo[3,2-b] pyridinyl

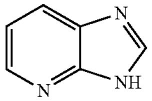
imidazo[4,5-b] pyridinyl

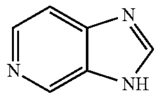
imidazo[4,5-c] pyridinyl

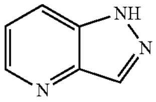
pyrazolo[4,3-d] pyridinyl

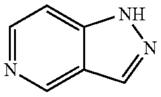
pyrazolo[4,3-c] pyridinyl

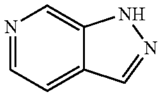
pyrazolo[3,4-c] pyridinyl

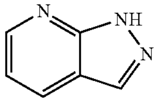
pyrazolo[3,4-b] pyridinyl

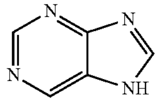
purinyl pyridinyl

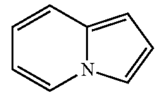
indolizinyl

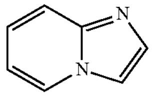
imidazo[1,2-a] pyridinyl

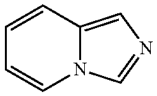
imidazo[1,5-a] pyridinyl

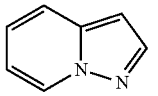
pyrazolo[1,5-a] pyridinyl

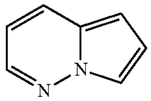
pyrrolo[1,2-b] pyridazinyl

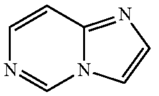
imidazo[1,2-c] pyrimidinyl

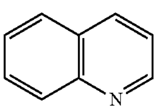
quinolinyl

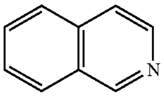
isoquinolinyl

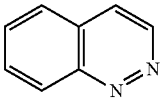
cinnolinyl

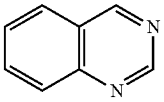
quinazolinyl

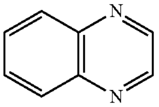
quinoxalinyl

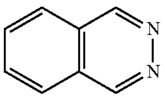
phtalazinyl

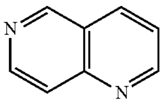
1,6-naphtyridinyl

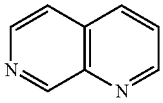
1,7-naphtyridinyl

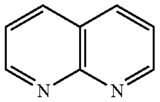
1,8-naphtyridinyl

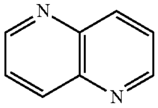
1,5-naphtyridinyl

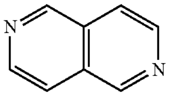
2,6-naphtyridinyl

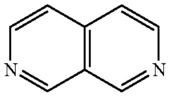
2,7-naphtyridinyl

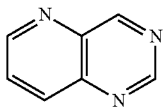
pyrido[3,2-d] pyrimidinyl

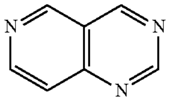
pyrido[4,3-d] pyrimidinyl

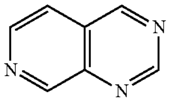
pyrido[3,4-d] pyrimidinyl

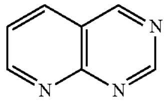
pyrido[2,3-d] pyrimidinyl

-continued

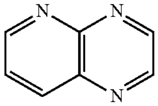
pyrido[2,3-d] pyrazinyl

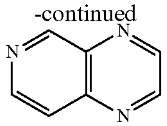
pyrido[3,4-b] pyrazinyl

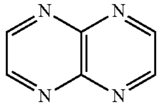
pyrazino[2,3-b] pyrazinyl

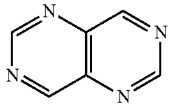
pyrimido[5,4-d] pyrimidinyl

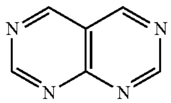
pyrimido[4,5-d] pyrimidinyl

Those heteroaryl substituents can be attached to any pendant group via any of its ring atoms suitable for such an attachment.

When used in reference to a ring atom of a heterocycle, the term “nitrogen” includes a substituted nitrogen. As an example, in a saturated or partially unsaturated ring having 1-3 heteroatoms selected from oxygen, sulfur or nitrogen, the nitrogen is N (as in 3,4-dihydro-2H-pyrrolyl), NH (as in pyrrolidinyl), or N-SUB with SUB being a suitable substituent (as in N-substituted pyrrolidinyl).

The term “unsaturated”, as used herein, means that a moiety or group or substituent has one or more units of unsaturation.

As used herein, the term “bicyclic”, “bicyclic ring” or “bicyclic ring system” refers to any bicyclic ring system, i.e. carbocyclic or heterocyclic, saturated or having one or more units of unsaturation, i.e. being partially unsaturated or aromatic, having one or more atoms in common between the two rings of the ring system. Thus, the term includes any permissible ring fusion, such as ortho-fused or spirocyclic. As used herein, the term “heterobicyclic” is a subset of “bicyclic” that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. Likewise, the term “tricyclic”, “tricyclic ring” or “tricyclic ring system” refers to any tricyclic ring system, i.e. carbocyclic or heterocyclic, saturated or having one or more units of unsaturation, i.e. being partially unsaturated or aromatic, in which a bicyclic ring system (as defined above) is fused with another, third ring. Thus, the term includes any permissible ring fusion. As used herein, the term “heterotricyclic” is a subset of “tricyclic” that requires that one or more heteroatoms are present in one or both rings of the tricycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a tricyclic group has 10-14 ring members and 0-5 heteroatoms independently selected from nitrogen, oxygen, or sulfur.

As described herein, certain compounds of the invention contain “substituted” or “optionally substituted” moieties. In general, the term “substituted”, whether preceded by the term “optionally” or not, means that one or more hydrogens of the designated moiety are replaced with a suitable substituent. "Substituted" applies to one or more hydrogens that are either explicit or implicit from the structure. Unless otherwise indicated, a "substituted" or "optionally substituted" group has a suitable substituent at each substitutable position of the group, and when more than one position in any given structure is substituted with more than one substituent selected from a specified group, the substituent is either the same or different at every position. If a certain group, substituent, moiety or radical is "mono-substituted", it bears one (1) substituent. If it is "di-substituted", it bears two (2) substituents, being either the same or different; if it is "tri-substituted", it bears three (3) substituents, wherein all three are the same or two are the same and the third is different or all three are different from each other. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

If not specified otherwise elsewhere in the specification it is understood that each optional substituent on a substitutable carbon is a monovalent substituent independently selected from halogen; —$(CH_2)_{0-4}R^{\circ}$; —$(CH_2)_{0-4}OR^{\circ}$; —$O(CH_2)_{0-4}R^{\circ}$, —O—$(CH_2)_{0-4}C(O)OR^{\circ}$; —$(CH_2)_{0-4}CH(OR^{\circ})_2$; —$(CH_2)_{0-4}SR^{\circ}$; —$(CH_2)_{0-4}Ph$, which may be substituted with one or more $R^{\circ}$; —$(CH_2)_{0-40}(CH_2)_{0-1}Ph$ which may be substituted with one or more $R^{\circ}$; —CH—CHPh, which may be substituted with one or more $R^{\circ}$; —$CH_2)_{0-40}(CH_2)_{0-1}$— pyridyl which may be substituted with one or more $R^{\circ}$; —$NO_2$; —CN; —$N_3$; —$(CH_2)_{0-4}N(R^{\circ})_2$; —$(CH_2)_{0-4}N(R^{\circ})C(O)R^{\circ}$; —$N(R^{\circ})C(S)$ $R^{\circ}$; —$(CH_2)_{0-4}N(R^{\circ})C(O)NR^{\circ}_2$; —$N(R^{\circ})C(S)$ $NR^{\circ}_2$; —$(CH_2)_{0-4}N(R^{\circ})C(O)OR^{\circ}$; —$N(R^{\circ})N(R^{\circ})C(O)R^{\circ}$; —$N(R^{\circ})N(R^{\circ})C(O)NR^{\circ}_2$; —$N(R^{\circ})N(R^{\circ})C(O)OR^{\circ}$; —$(CH_2)_{0-4}C(O)R^{\circ}$; —$C(S)R^{\circ}$; —$(CH_2)_{0-4}C(O)OR^{\circ}$; —$(CH_2)_{0-4}C(O)SR^{\circ}$; —$CH_2)_{0-4}C(O)OSiR^{\circ}_3$; —$(CH_2)_{0-4}OC(O)$ $R^{\circ}$; —$OC(O)(CH_2)_{0-4}SR$—, $SC(S)SR^{\circ}$; —$(CH_2)_{0-4}SC(O)R^{\circ}$; —$(CH_2)_{0-4}C(O)NR^{\circ}_2$; —$C(S)$ $NR^{\circ}_2$; —$C(S)SR^{\circ}$; —$SC(S)SR^{\circ}$, —$(CH_2)_{0-4}OC(O)NR^{\circ}_2$; —$C(O)N(OR^{\circ})R^{\circ}$; —$C(O)C(O)$ $R^{\circ}$; —$C(O)CH_2C(O)R^{\circ}$; —$C(NOR^{\circ})R^{\circ}$; —$CH_2)_{0-4}$ $SSR^{\circ}$; —$(CH_2)_{0-4}S(O)_2R^{\circ}$; —$(CH_2)_{0-4}S(O)_2OR^{\circ}$; —$(CH_2)_{0-4}OS(O)_2R^{\circ}$; —$S(O)_2NR^{\circ}_2$; —$S(O)(NR^{\circ})$ $R^{\circ}$; —$S(O)_2N{=}C(NR^{\circ}_2)_2$; —$CH_2)_{0-4}S(O)R^{\circ}$; —$N(R^{\circ}S(O)_2NR^{\circ}_2$; —$N(R^{\circ}S(O)_2R^{\circ}$; —$N(OR^{\circ})R^{\circ}$; —$C(NH)NR^{\circ}_2$; —$P(O)_2R^{\circ}$; —$P(O)R^{\circ}_2$; —$OP(O)R^{\circ}_2$; —$OP(O)(OR^{\circ})_2$; $SiR^{\circ}_3$; —$C_{1-4}$ straight or branched alkylene)O—$N(R^{\circ})_2$; or —($C_{1-4}$ straight or branched alkylene)C(O)O—$N(R^{\circ})_2$. It is understood that "Ph" means phenyl; and that "—$(CH_2)_{0-4}$" means that there is either no alkylene group if the subscript is "0" (zero) or an alkylene group with 1, 2, 3 or 4 $CH_2$ units.

Each $R^{\circ}$ is independently hydrogen, halogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^{\circ}$ selected from ═O and ═S; or each $R^{\circ}$ is optionally substituted with a monovalent substituent independently selected from halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\circ}_2$, —$NO_2$, —$SiR^{\bullet}_3$, —$OSiR^{\circ}_3$, —$C(O)SR^{\bullet}$, —($C_{1-4}$ straight or branched alkylene)$C(O)OR^{\bullet}$, or —$SSR^{\bullet}$. It is understood that "Ph" means phenyl; "halo" means halogen; and "—$(CH_2)_{0-2}$" means that there is either no alkylene group if the subscript is "0" (zero) or an alkylene group with 1 or 2 $CH_2$ units.

Each $R^{\bullet}$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens; or wherein an optional substituent on a saturated carbon is a divalent substituent independently selected from ═O, ═S, ═$NNR^*_2$, ═$NNHC(O)R^*$, ═$NNHC(O)OR^*$, ═$NNHS(O)_2$ $R^*$, ═$NR^*$, ═$NOR^*$, —$O(C(R^*_2))_{2-3}O$—, or —$S(C(R^*_2))_{2-3}S$—, or a divalent substituent bound to vicinal substitutable carbons of an "optionally substituted" group is —$O(CR^*_2)_{2-3}O$—, wherein each independent occurrence of $R^*$ is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When $R^*$ is $C_{1-6}$ aliphatic, $R^*$ is optionally substituted with halogen, —$R^{\bullet}$, -(halo$R^{\bullet}$), —OH, —$OR^{\bullet}$, —O(halo$R^{\bullet}$), —CN, —C(O)OH, —$C(O)OR^{\bullet}$, —$NH_2$, —$NHR^{\bullet}$, —$NR^{\circ}_2$, or —$NO_2$, wherein each $R^*$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens.

An optional substituent on a substitutable nitrogen is independently —$R^{\dagger}$, —$NR^{\dagger}_2$, —$C(O)R^{\dagger}$, —$C(O)OR^{\dagger}$, —$C(O)C(O)R^{\dagger}$, —$C(O)CH_2C(O)R^{\dagger}$, —$S(O)_2R^{\dagger}$, —$S(O)_2NR^{\dagger}_2$, —$C(S)NR^{\dagger}_2$, —$C(NH)NR^{\dagger}_2$, or —$N(R^{\dagger})S(O)_2R^{\dagger}$; wherein each $R^{\dagger}$ is independently hydrogen, $C_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when $R^{\dagger}$ is $C_{1-6}$ aliphatic, $R^{\dagger}$ is optionally substituted with halogen, —$R^{\bullet}$, -(halo$R^{\bullet}$), —OH, —$OR^{\bullet}$, —O(halo$R^{\bullet}$), —CN, —C(O)OH, —$C(O)OR^{\bullet}$, —$NH_2$, —$NHR^{\bullet}$, —$NR^{\circ}_2$, or —$NO_2$, wherein each $R^{\bullet}$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens. It is understood that "Ph" means phenyl; and "halo" means halogen.

In the context of the present invention the term "derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

The compounds of the present invention can be in the form of a prodrug compound. "Prodrugs" and "prodrug compound" mean a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, in which the amino group in a compound of the present invention is acylated, alkylated or phosphorylated, e.g., eicosanoylamino, alanylamino, pivaloyl-oxymethylamino or in which the hydroxyl group is acylated, alkylated, phosphorylated or converted into the borate, e.g. acetyloxy, palmitoyloxy, pivaloyloxy, succinyloxy, fumaryloxy, alanyloxy or in which the carboxyl group is esterified or amidated, or in which a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino-, acyloxymethylester, linolenoyl-ester.

The term "solvates" means addition forms of the compounds of the present invention with solvents, preferably pharmaceutically acceptable solvents that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, e.g. a mono- or dihydrate. If the solvent is alcohol, the solvate formed is an alcoholate, e.g., a methanolate or ethanolate. If the solvent is an ether, the solvate formed is an etherate, e.g., diethyl etherate.

The term "N-oxides" means such compounds of the present invention that contain an amine oxide moiety, i.e. the oxide of a tertiary amine group.

The compounds of formula I-a, I-b or I-c may have one or more centres of chirality. They may accordingly occur in various enantiomeric and diastereomeric forms, as the case may be, and be in racemic or optically active form. The invention, therefore, also relates to the optically active forms, enantiomers, racemates, diastereomers, mixtures thereof in all ratios, collectively: "stereoisomers" for the purpose of the present invention, of these compounds. Since the pharmaceutical activity of the racemates or stereoisomers of the compounds according to the invention may differ, it may be desirable to use a specific stereoisomer, e.g. one specific enantiomer or diastereomer. In these cases, a compound according to the present invention obtained as a racemate—or even intermediates thereof—may be separated into the stereoisomeric (enantiomeric, diastereoisomeric) compounds by chemical or physical measures known to the person skilled in the art. Another approach that may be applied to obtain one or more specific stereoisomers of a compound of the present invention in an enriched or pure form makes use of stereoselective synthetic procedures, e.g. applying starting material in a stereoisomerically enriched or pure form (for instance using the pure or enriched (R)- or (S)-enantiomer of a particular starting material bearing a chiral center) or utilizing chiral reagents or catalysts, in particular enzymes. In the context of the present invention the term "pure enantiomer" usually refers to a relative purity of one enantiomer over the other (its antipode) of equal to or greater than 95%, preferably ≥98%, more preferably ≥98.5%, still more preferably 99%.

Thus, for example, the compounds of the invention which have one or more centers of chirality and which occur as racemates or as mixtures of enatiomers or diastereoisomers can be fractionated or resolved by methods known per se into their optically pure or enriched isomers, i.e. enantiomers or diastereomers. The separation of the compounds of the invention can take place by chromatographic methods, e.g. column separation on chiral or nonchiral phases, or by recrystallization from an optionally optically active solvent or by use of an optically active acid or base or by derivatization with an optically active reagent such as, for example, an optically active alcohol, and subsequent elimination of the radical.

In the context of the present invention the term "tautomer" refers to compounds of the present invention that may exist in tautomeric forms and show tautomerism; for instance, carbonyl compounds may be present in their keto and/or their enol form and show keto-enol tautomerism. Those tautomers may occur in their individual forms, e.g., the keto or the enol form, or as mixtures thereof and are described separately and together as mixtures in any ratio. The same applies for cis/trans isomers, E/Z isomers, conformers and the like.

In one embodiment the compounds of the present invention are in the form of free base or acid—as the case may be—, i.e. in their non-salt (or salt-free) form. In another embodiment the compounds of the present invention are in the form of a pharmaceutically acceptable salt, a pharmaceutically acceptable solvate, or a pharmaceutically acceptable solvate of a pharmaceutically acceptable salt.

The term "pharmaceutically acceptable salts" refers to salts prepared from pharmaceutically acceptable bases or acids, including inorganic bases or acids and organic bases or acids. In cases where the compounds of the present invention contain one or more acidic or basic groups, the invention also comprises their corresponding pharmaceutically acceptable salts. Thus, the compounds of the present invention which contain acidic groups, such as carboxyl groups, can be present in salt form, and can be used according to the invention, for example, as alkali metal salts, alkaline earth metal salts, aluminium salts or as ammonium salts. More precise examples of such salts include lithium salts, sodium salts, potassium salts, calcium salts, magnesium salts, barium salts or salts with ammonia or organic amines such as, for example, ethylamine, ethanolamine, diethanolamine, triethanolamine, piperdine, N-methylglutamine or amino acids. These salts are readily available, for instance, by reacting the compound having an acidic group with a suitable base, e.g. lithium hydroxide, sodium hydroxide, sodium propoxide, potassium hydroxide, potassium ethoxide, magnesium hydroxide, calcium hydroxide or barium hydroxide. Other base salts of compounds of the present invention include but are not limited to copper(I), copper(II), iron(II), iron (III), manganese(II) and zinc salts. Compounds of the present invention which contain one or more basic groups, e.g. groups which can be protonated, can be present in salt form, and can be used according to the invention in the form of their addition salts with inorganic or organic acids. Examples of suitable acids include hydrogen chloride, hydrogen bromide, hydrogen iodide, phosphoric acid, sulfuric acid, nitric acid, methanesulfonic acid, p-toluenesulfonic acid, naphthalenedisulfonic acid, sulfoacetic acid, trifluoroacetic acid, oxalic acid, acetic acid, tartaric acid, lactic acid, salicylic acid, benzoic acid, carbonic acid, formic acid, propionic acid, pivalic acid, diethylacetic acid, malonic acid, succinic acid, pimelic acid, fumaric acid, malonic acid, maleic acid, malic acid, embonic acid, mandelic acid, sulfaminic acid, phenylpropionic acid, gluconic acid, ascorbic acid, isonicotinic acid, citric acid, adipic acid, taurocholic acid, glutaric acid, stearic acid, glutamic acid or aspartic acid, and other acids known to the person skilled in the art. The salts which are formed are, inter alia, hydrochlorides, chlorides, hydrobromides, bromides, iodides, sulfates, phosphates, methanesulfonates (mesylates), tosylates, carbonates, bicarbonates, formates, acetates, sulfoacetates, triflates, oxalates, malonates, maleates, succinates, tartrates, malates, embonates, mandelates, fumarates, lactates, citrates, glutarates, stearates, aspartates and glutamates. The stoichiometry of the salts formed from the compounds of the invention may moreover be an integral or non-integral multiple of one.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$)alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Therefore, the following items are also in accordance with the invention:

(a) all stereoisomers or tautomers of the compounds, including mixtures thereof in all ratios;
(b) prodrugs of the compounds, or stereoisomers or tautomers of these prodrugs;
(c) pharmaceutically acceptable salts of the compounds and of the items mentioned under (a) and (b);
(d) pharmaceutically acceptable solvates of the compounds and of the items mentioned under (a), (b) and (c);
(e)N-oxides of the compounds and of the items mentioned under (a), (b), (c), and (d).

It should be understood that all references to compounds above and below are meant to include these items, in particular pharmaceutically acceptable solvates of the compounds, or pharmaceutically acceptable solvates of their pharmaceutically acceptable salts.

There is furthermore intended that a compound of the present invention includes isotope-labelled forms thereof. An isotope-labelled form of a compound of the formula I-a, I-b or I-c is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the present invention by well-known methods include isotopes of hydrogen, carbon, nitrogen, oxygen, phosphorus, sulfur, fluorine and chlorine, for example $^2H$ (D), $^3H$, $^{13}C$, $^{14}C$, $^{15}N$, $^{18}O$, $^{17}O$, $^{31}P$, $^{32}P$, $^{33}S$, $^{34}S$, $^{35}S$, $^{36}S$, $^{18}F$ and $^{36}Cl$, respectively. A compound of formula I-a, I-b or I-c or a pharmaceutically acceptable salt therof which contains one or more of the above-mentioned isotopes and/or other isotopes of other atoms is intended to be part of the present invention. An isotope-labelled compound of formula I-a, I-b or I-c can be used in a number of beneficial ways. For example, an isotope-labelled compound of the present invention into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of formula I-a, I-b or I-c has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of formula I-a, I-b or I-c can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2H$; D) can also be incorporated into a compound of formula I-a, I-b or I-c for the purpose of manipulating the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of the formula Ia and Ib that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I-a, I-b or I-c with improved stability through resistance to such oxidative meta-bolism. Significant improvements in the pharmacokinetic profiles of compounds of the formula I-a, I-b or I-c are thereby obtained, and can be expressed quantitatively in terms of increases in the in vivo half-life (t½), concentration at maximum therapeutic effect ($C_{max}$), area under the dose response curve (AUC), and F; and in terms of reduced clearance, dose and materials costs.

The following is intended to illustrate the above: a compound of formula I-a, I-b or I-c which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is deter-mined that the half-life of the parent compound can be extended by up to 100% as the result of deuterium-hydrogen exchange of this type.

Deuterium-hydrogen exchange in a compound of the present invention can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14,1-40, 1985, Gillette et al, Biochemistry 33(10) 2927-2937, 1994, and Jarman et al. Carcinogenesis 16(4), 683-688, 1995.

Furthermore, the present invention relates to pharmaceutical compositions comprising at least one compound of formula I-a, I-b or I-c, or its derivatives, prodrugs, solvates, tautomers or stereoisomers thereof as well as the pharmaceutically acceptable salts of each of the foregoing, including mixtures thereof in all ratios, as active ingredient, together with a pharmaceutically acceptable carrier.

For the purpose of the present invention the term "pharmaceutical composition" (or "pharmaceutical formulation") refers to a composition or product comprising one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing at least one compound of the present invention and a pharmaceutically acceptable carrier. It may further comprise physiologically acceptable excipients, auxiliaries, adjuvants, diluents and/or additional pharmaceutically active substance other than the compounds of the invention.

The pharmaceutical compositions include compositions and pharmaceutical formulations suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

A pharmaceutical composition of the present invention may additionally comprise one or more other compounds as active ingredients (drugs), such as one or more additional compounds of the present invention. In a particular embodiment the pharmaceutical composition further comprises a second active ingredient or its derivatives, prodrugs, solvates, tautomers or stereoisomers thereof as well as the pharmaceutically acceptable salts of each of the foregoing, including mixtures thereof in all ratios, wherein that second active ingredient is other than a compound of formula I-a, I-b or I-c; preferably, that second active ingredient is a compound that is useful in the treatment, prevention, suppression and/or amelioration of medicinal conditions or pathologies for which the compounds of the present invention are useful as well and which are listed elsewhere hereinbefore or hereinafter. Such combination of two or more active ingredients or drugs may be safer or more effective than either drug or active ingredient alone, or the combination is safer or more effective than it would be expected based on the additive properties of the individual drugs. Such other drug(s) may be administered, by a route and in an amount commonly used contemporaneously or sequentially with a compound of the invention. When a compound of the invention is used contemporaneously with one or more other drugs or active ingredients, a combination product containing such other drug(s) and the compound of the invention—also referred to as "fixed dose combination"—is preferred. However, combination therapy also includes therapies in which the compound of the present invention and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of the invention.

The compounds of the present invention—or derivatives, N-oxides, prodrugs, solvates, tautomers or stereoisomers thereof and/or the pharmaceutically acceptable salts of each of the foregoing, including mixtures thereof in all ratios—can be used as medicaments. They have been found to exhibit pharmacological activity by inhibiting acetyl-CoA synthetase (ACSS2). They may also exhibit lower levels, if any, of CYP induction, in particular CYP3A4 induction when compared to other ACSS2 inhibitors known in the art. Furthermore, when tested in an MNT (micronuclei) in-vitro assay on genotoxicity, they may exhibit improved properties, i.e. a negative MNT assay read-out, in comparison to prior art ACSS2 inhibitors.

Thus, the compounds of the present invention being ACSS2 inhibitors are useful in particular in the treatment, prevention, suppression and/or amelioration of hyperproliferative disorders and cancer, in particular tumors including solid tumors, of bladder, breast, colorectal, colon, kidney, liver, lung, head and neck, esophagus, bladder, gall bladder, ovary, pancreas, stomach, cervix, thyroid, prostate, and skin, including squamous cell carcinoma; leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma and Burkett's lymphoma; chronic lymphocytic leukemia ("CLL"), acute and chronic myelogenous leukemia, myelodysplastic syndrome and promyelocyte leukemia; fibrosarcoma, rhabdomyosarcoma; mantle cell lymphoma, myeloma; astrocytoma, neuroblastoma, glioma, glioblastoma, malignant glial tumors, astrocytoma, hepatocellular carcinoma, gastrointestinal stromal tumors ("GIST") and schwannomas; melanoma, multiple myeloma, seminoma, teratocarcinoma, osteosarcoma, xenoderma pigmentosum, keratoctanthoma, thyroid follicular cancer, endometrial cancer, gastrointestinal tract cancer and Kaposi's sarcoma; acanthoma, acinic cell carcinoma, acoustic neuroma, acral lentiginous melanoma, acrospiroma, acute eosinophilic leukemia, acute lymphoblastic leukemia, acute megakaryoblastic leukemia, acute monocytic leukemia, acute myeloblastic leukemia with maturation, acute myeloid dendritic cell leukemia, acute myeloid leukemia, acute promyelocytic leukemia, adamantinoma, adenocarcinoma, adenoid cystic carcinoma, adenoma, adenomatoid odontogenic tumor, adrenocortical carcinoma, adult T-cell leukemia, aggressive NK-cell leukemia, AIDS-related cancers, AIDS-related lymphoma, alveolar soft part sarcoma, ameloblastic fibroma, anal cancer, anaplastic large cell lymphoma, anaplastic thyroid cancer, angioimmunoblastic T-cell lymphoma, angiomyolipoma, angiosarcoma, appendix cancer, astrocytoma, atypical teratoid rhabdoid tumor, basal cell carcinoma, basallike carcinoma, B-cell leukemia, B-cell lymphoma, bellini duct carcinoma, biliary tract cancer, bladder cancer, blastoma, bone cancer, bone tumor, brain stem glioma, brain tumor, breast cancer, brenner tumor, bronchial tumor, bronchioloalveolar carcinoma, brown tumor, Burkitt's lymphoma, carcinoid tumor, carcinoma, carcinosarcoma, Castleman's disease, central nervous system embryonal tumor, cerebellar astrocytoma, cerebral astrocytoma, cervical cancer, cholangiocarcinoma, chondroma, chondrosarcoma, chordoma, choriocarcinoma, choroid plexus papilloma, chronic lymphocytic leukemia, chronic monocytic leukemia, chronic myelogenous leukemia, chronic myeloproliferative disorder, chronic neutrophilic leukemia, clear cell renal cell carcinoma, clear-cell tumor, colon cancer, colorectal cancer, craniopharyngioma, cutaneous T-cell lymphoma, dermatofibrosarcoma protuberans, dermoid cyst, desmoplastic small round cell tumor, diffuse large B cell lymphoma, dysembryoplastic neuroepithelial tumor, embryonal carcinoma, endodermal sinus tumor, endometrial cancer, endometrial uterine cancer, endometrioid tumor, enteropathyassociated T-cell lymphoma, ependymoblastoma, ependymoma, epithelioid sarcoma, erythroleukemia, esophageal cancer, esthesioneuroblastoma, Ewing's sarcoma, extracranial germ cell tumor, extragonadal germ cell tumor, extrahepatic bile duct cancer, extramammary Paget's disease, fallopian tube cancer, fibroma, fibrosarcoma, follicular lymphoma, follicular thyroid cancer, gallbladder cancer, ganglioglioma, ganglioneuroma, gastric cancer, gastric lymphoma, gastrointestinal cancer, gastrointestinal carcinoid tumor, gastrointestinal stromal tumor, germ cell tumor, germinoma, gestational choriocarcinoma, gestational trophoblastic tumor, giant cell tumor of bone, glioblastoma multiforme, glioma, gliomatosis cerebri, glomus tumor, glucagonoma, gonadoblastoma, granulosa cell tumor, hairy cell leukemia, head and neck cancer, heart cancer, hemangioblastoma, hemangiopericytoma, hemangiosarcoma, hematological malignancy, hepatocellular carcinoma, hepatosplenic T-cell lymphoma, Hodgkin lymphoma, hypopharyngeal cancer, hypothalamic glioma, inflammatory breast cancer, intraocular melanoma, islet cell carcinoma, juvenile myelomonocytic leukemia, Kaposi's sarcoma, kidney cancer, klatskin tumor, krukenberg tumor, laryngeal cancer, lentigo maligna melanoma, leukemia, lip and oral cavity cancer, liposarcoma, lung cancer, luteoma, lymphangioma, lymphangiosarcoma, lymphoepithelioma, lymphoid leukemia, lymphoma, macroglobulinemia, malignant fibrous histiocytoma, malignant glioma, malignant mesothelioma, malignant peripheral nerve sheath tumor, malignant rhabdoid tumor, malignant triton tumor, malt lymphoma, mantle cell lymphoma, mast cell leukemia, mediastinal germ cell tumor, mediastinal tumor, medullary thyroid cancer, medulloblastoma, medulloepithelioma, melanoma, meningioma, merkel cell carcinoma, mesothelioma, metastatic squamous neck cancer with occult primary, metastatic urothelial carcinoma, mixed mullerian tumor, monocytic leukemia, mouth cancer, mucinous tumor, multiple endocrine neoplasia syndrome, multiple myeloma, mycosis fungoides, myelodysplastic disease, myeloid leukemia, myeloid sarcoma, myeloproliferative disease, myxoma, nasal cavity cancer, nasopharyngeal cancer, neoplasm, neurinoma, neuroblastoma, neurofibroma, neuroma, nodular melanoma, non-Hodgkin lymphoma, non-melanoma skin cancer, non-small cell lung cancer, ocular oncology, oligoastrocytoma, oligodendroglioma, oncocytoma, optic nerve sheath meningioma, oral cancer, oropharyngeal cancer, osteosarcoma, ovarian cancer, ovarian epithelial cancer, ovarian germ cell tumor, ovarian low malignant potential tumor, pancoast tumor, pancreatic cancer, papillary thyroid cancer, papillomatosis, paraganglioma, paranasal sinus cancer, parathyroid cancer, penile cancer, perivascular epithelioid cell tumor, pharyngeal cancer, pheochromocytoma, pineal parenchymal tumor of intermediate differentiation, pineoblastoma, pituicytoma, pituitary adenoma, pituitary tumor, plasma cell neoplasm, pleuropulmonary blastoma, polyembryoma, precursor T-lymphoblastic lymphoma, primitive neuroectodermal tumor, prostate cancer, pseudomyxoma peritonei, rectal cancer, renal cell carcinoma, retinoblastoma, rhabdomyoma, rhabdomyosarcoma, Richter's transformation, sacrococcygeal teratoma, salivary gland cancer, sarcoma, schwannomatosis, sebaceous gland carcinoma, secondary neoplasm, seminoma, serous tumor, Sertoli-Leydig cell tumor, sex cord-stromal tumor, sezary syndrome, signet ring cell carcinoma, skin cancer, small blue round cell tumor, small cell carcinoma, small cell lung cancer, small cell lymphoma, small intestine cancer, soft tissue sarcoma, somatostatinoma, soot wart, spinal tumor, splenic marginal zone lymphoma, squamous cell carcinoma, stomach cancer, superficial spreading melanoma, supratentorial primitive neuroectodermal tumor, surface epithelial-stromal tumor, synovial sarcoma, T-cell acute lymphoblastic leukemia, T-cell large granular lymphocyte leukemia, T-cell leukemia, T-cell lymphoma, T-cell prolymphocytic leukemia, teratoma, terminal lymphatic cancer, testicular cancer, thecoma, throat cancer, thymic carcinoma, thymoma, thyroid cancer, transitional cell cancer of renal pelvis and ureter, transitional cell carcinoma, urachal cancer, urethral cancer, urogenital neoplasm, uterine sarcoma, uveal melanoma, vaginal cancer, verner morrison syndrome, verrucous carcinoma, visual pathway glioma, vulvar cancer, Waldenstrom's macroglobulinemia, Warthin's tumor, Wilms' tumor or any combination thereof. However, since activity of ACSS2 plays a role in acetyl-CoA synthesis in normal, i.e. non-cancer cells too, the compounds of the present invention are useful also in the the treatment, prevention, suppression and/or amelioration of an inflammatory disorder or disease, in particular Crohn's disease, ulcerative colitis, idiopathic pulmonary fibrosis, muscular dystrophy, rheumatoid arthritis, and systemic sclerosis (scleroderma); a neurogenerative disorder or disease, in particular Huntington's disease; Lipid metabolism disorders, e.g. NASH (non-alcoholic steatohepatitis), NAFLD (non-alcoholic fatty liver disease), fatty liver disease; viral infections, e.g. with cytomegalovirus; post-traumatic stress disorder (PTSD); bipolar disorder, depression, Tourettes's Syndrome, schizophrenia, obsessive-compulsive disorder, anxiety disorder, panic disorders, phobias, addiction to e.g. alcohol, tobacco, opioids, sedatives, hypnotics, anxiolytics, cocaine, cannabis, amphetamines, hallucinogens, inhalants, phencyclidine, impulse control disorders, behavioral addictions.

In a particular embodiment the compounds of the present invention are for use in the prevention and/or treatment, especially in the treatment of any of the disorders or diseases listed above, preferably of cancer, in particular tumors including solid tumors, of the specific types of cancer disclosed in the previous paragraph; of an inflammatory disorder or disease, in particular Crohn's disease, ulcerative colitis, idiopathic pulmonary fibrosis, muscular dystrophy, rheumatoid arthritis, and systemic sclerosis (scleroderma); a neurogenerative disorder or disease, in particular Huntington's disease; Lipid metabolism disorders, e.g. NASH (non-alcoholic steatohepatitis), NAFLD (non-alcoholic fatty liver disease), fatty liver disease; viral infections, e.g. with cytomegalovirus; post-traumatic stress disorder (PTSD); bipolar disorder, depression, Tourettes's Syndrome, schizophrenia, obsessive-compulsive disorder, anxiety disorder, panic disorders, phobias, addiction to e.g. alcohol, tobacco, opioids, sedatives, hypnotics, anxiolytics, cocaine, cannabis, amphetamines, hallucinogens, inhalants, phencyclidine, impulse control disorders, behavioral addictions.

Another particular embodiment of the present invention is a method for preventing and/or treating, preferably treating a disorder or disease selected from the group consisting of hyperproliferative disorders and cancer, in particular tumors including solid tumors, of the specific types of cancer disclosed in the previous paragraphs; of an inflammatory disorder or disease, in particular Crohn's disease, ulcerative colitis, idiopathic pulmonary fibrosis, muscular dystrophy, rheumatoid arthritis, and systemic sclerosis (scleroderma); a neurogenerative disorder or disease, in particular Huntington's disease; Lipid metabolism disorders, e.g. NASH (non-alcoholic steatohepatitis), NAFLD (non-alcoholic fatty liver disease), fatty liver disease; viral infections, e.g. with cytomegalovirus; post-traumatic stress disorder (PTSD); bipolar disorder, depression, Tourettes's Syndrome, schizophrenia, obsessive-compulsive disorder, anxiety disorder, panic disorders, phobias, addiction to e.g. alcohol, tobacco, opioids, sedatives, hypnotics, anxiolytics, cocaine, cannabis, amphetamines, hallucinogens, inhalants, phencyclidine, impulse control disorders, behavioral addictions.

Still another particular embodiment of the invention is the use of a compound of the present invention—or derivatives, N-oxides, prodrugs, solvates, tautomers or stereoisomers thereof and/or the pharmaceutically acceptable salts of each of the foregoing, including mixtures thereof in all ratios—for the manufacturing of a medicament, in particular for preventing and/or treating, preferably treating a disorder or disease selected from the group consisting of hyperproliferative disorders and cancer, in particular tumors including solid tumors, of the specific types of cancer disclosed in the previous paragraphs; of an inflammatory disorder or disease, in particular Crohn's disease, ulcerative colitis, idiopathic pulmonary fibrosis, muscular dystrophy, rheumatoid arthritis, and systemic sclerosis (scleroderma); a neurogenerative disorder or disease, in particular Huntington's disease; Lipid metabolism disorders, e.g. NASH (non-alcoholic steatohepatitis), NAFLD (non-alcoholic fatty liver disease), fatty liver disease; viral infections, e.g. with cytomegalovirus; post-traumatic stress disorder (PTSD); bipolar disorder, depression, Tourettes's Syndrome, schizophrenia, obsessive-compulsive disorder, anxiety disorder, panic disorders, phobias, addiction to e.g. alcohol, tobacco, opioids, sedatives, hypnotics, anxiolytics, cocaine, cannabis, amphetamines, hallucinogens, inhalants, phencyclidine, impulse control disorders, behavioral addictions.

Preferably, the present invention relates to a compound of the present invention for use in the prevention and/or treatment of a disease—or, alternatively, a method for preventing and/or treating a disease by administering an effective amount of a compound of the present invention; or, in another alternative, a use of a compound of the present invention for the manufacturing of a medicament for the prevention and/or treatment of a disease—wherein that disease is a cancer, in particular tumors including solid tumors, of the specific types of cancer disclosed in the previous paragraphs; and more preferably, wherein administration of the compound is simultaneous, sequential or in alternation with administration of at least one other active drug agent.

The disclosed compounds of formulas I-a, I-b and I-c can be administered in combination with other known therapeutic agents, including anticancer agents. As used here, the term "anticancer agent" relates to any agent which is administered to a patient with cancer for the purposes of treating the cancer. The anti-cancer treatment defined above may be applied as a monotherapy or may involve, in addition to the herein disclosed compounds of formulas I-a, I-b and I-c, conventional surgery or radiotherapy or medicinal therapy. Such medicinal therapy, e.g. a chemotherapy or a targeted therapy, may include one or more, but preferably one, of the following anti-tumor agents:

Alkylating Agents
such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds
such as carboplatin, cisplatin, eptaplatin, miriplatine hydrate, oxaliplatin, lobaplatin, nedaplatin, picoplatin, satraplatin;
lobaplatin, nedaplatin, picoplatin, satraplatin;

DNA Altering Agents
such as amrubicin, bisantrene, decitabine, mitoxantrone, procarbazine, trabectedin, clofarabine;
amsacrine, brostallicin, pixantrone, laromustine[1,3];

Topoisomerase Inhibitors
such as etoposide, irinotecan, razoxane, sobuzoxane, teniposide, topotecan; amonafide, belotecan, elliptinium acetate, voreloxin;

Microtubule Modifiers
such as cabazitaxel, docetaxel, eribulin, ixabepilone, paclitaxel, vinblastine, vincristine, vinorelbine, vindesine, vinflunine; fosbretabulin, tesetaxel;

Antimetabolites
such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer Antibiotics
such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin; aclarubicin, peplomycin, pirarubicin;

Hormones/Antagonists
- such as abarelix, abiraterone, bicalutamide, buserelin, calusterone, chlorotrianisene, degarelix, dexamethasone, estradiol, fluocortolone, fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[13]

Aromatase Inhibitors
- such as aminoglutethimide, anastrozole, exemestane, fadrozole, letrozole, testolactone; formestane;

Small Molecule Kinase Inhibitors
- such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tepotinib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinibi, XL-647[4];

Photosensitizers
- such as methoxsalen[3]; porfimer sodium, talaporfin, temoporfin;

Antibodies
- such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomabi, tabalumab[1,3], EMD-525797[4], atezolizumab, durvalumab, pembrolizumab, nivolumab[13];

Cytokines
- such as aldesleukin, interferon alfa[2], interferon alfa2a[3], interferon alfa2b[2],3 celmoleukin, tasonermin, teceleukin, oprelvekin[1,3], recombinant interferon beta-1a[4];

Drug Conjugates
- such as denileukin diftitox, ibritumomab tiuxetan, iobenguane 1123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines
- such as sipuleucel[3]; vitespen[3], emepepimut-S[3], oncoVAX[4], rindopepimut[3] troVax[4], MGN-1601[4], MGN-1703[4];

Miscellaneous
- alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, Ionidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4], PARP Inhibitors
- Olaparib, Veliparib.

MCT1 Inhibitors
- AZD3965[4], BAY-8002[4].

[1]Prop. INN (Proposed International Nonproprietary Name)

[2]Rec. INN(Recommended International Nonproprietary Names)

[3]USAN (United States Adopted Name)

[4]no INN.

A further embodiment of the present invention is a process for the manufacture of the pharmaceutical compositions of the present invention, characterized in that one or more compounds according to the invention and one or more compounds selected from the group consisting of solid, liquid or semiliquid excipients, auxiliaries, adjuvants, diluents, carriers and pharmaceutically active agents other than the compounds according to the invention, are converted in a suitable dosage form.

In another aspect of the invention, a set or kit is provided comprising a therapeutically effective amount of at least one compound of the invention and/or at least one pharmaceutical composition as described herein and a therapeutically effective amount of at least one further pharmacologically active substance other than the compounds of the invention. It is preferred that this set or kit comprises separate packs of a) an effective amount of a compound of formula I-a, I-b or I-c, or its derivatives, prodrugs, solvates, tautomers or stereoisomers thereof as well as the physiologically acceptable salts of each of the foregoing, including mixtures thereof in all ratios, and b) an effective amount of a further active ingredient that further active ingredient not being a compound of formula I-a, I-b or I-c.

The pharmaceutical compositions (formulations) of the present invention may be administered by any means that achieve their intended purpose. For example, administration may be via oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be via the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below:

Tablets: mixing of active ingredient/s and auxiliaries, compression of said mixture into tablets (direct compression), optionally granulation of part of mixture before compression.

Capsules: mixing of active ingredient/s and auxiliaries to obtain a flowable powder, optionally granulating powder, filling powders/granulate into opened capsules, capping of capsules.

Semi-solids (ointments, gels, creams): dissolving/dispersing active ingredient/s in an aqueous or fatty carrier; subsequent mixing of aqueous/fatty phase with complementary fatty/aqueous phase, homogenization (creams only).

Suppositories (rectal and vaginal): dissolving/dispersing active ingredient/s in carrier material liquified by heat (rectal: carrier material normally a wax, vaginal: carrier normally a heated solution of a gelling agent), casting said mixture into suppository forms, annealing and withdrawal suppositories from the forms.

Aerosols: dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more compounds of the invention into a dosage form suitable for administration to a patient in need of such a treatment. Usually, the transfer of one or more compounds of the invention into such a dosage form comprises the addition of one or more compounds, selected from the group consisting of carriers, excipients, auxiliaries and pharmaceutical active ingredients other than the compounds of the invention. Suitable processing steps include, but are not limited to combining, milling, mixing, granulating, dissolving, dispersing, homogenizing, casting and/or compressing the respective active and nonactive ingredients. Mechanical means for performing said processing steps are known in the art, for example from Ullmann's Encyclopedia of Industrial Chemistry, 5th Edition. In this respect, active ingredients are preferably at least one compound of the invention and optionally one or more additional compounds other than the compounds of the invention, which show valuable pharmaceutical properties, preferably those pharmaceutical active agents other than the compounds of the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The compounds of the invention may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the compounds of the invention, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropylmethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The compounds of the invention can also be lyophilized and the lyophilizates obtained can be used, for example, for the production of injection preparations.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the compounds of the present invention may be in the form of pharmaceutically acceptable salts. Other salts may, however, be useful in the preparation of the compounds of the invention or of their pharmaceutically acceptable salts. Suitable pharmaceutically acceptable salts of the compounds of this invention are those described hereinbefore and include acid addition salts which may, for example be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the compounds of the invention is known to the skilled artisan or can be easily determined by standard methods known in the art.

The compounds of the present invention and the optional additional active substances are generally administered analogously to commercial preparations. Usually, suitable doses that are therapeutically effective lie in the range between 0.0005 mg and 1000 mg, preferably between 0.005 mg and 500 mg and especially between 0.5 mg and 100 mg per dose unit. The daily dose is preferably between about 0.001 mg/kg and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The specific dose for the individual patient, in particular for the individual human patient, depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

The compounds of the present invention can be prepared according to the procedures of the following Schemes and Examples, using appropriate materials, and as further exemplified by the following specific examples. They may also be prepared by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for the said reactions. Use can also be made of variants which are known per se, but are not mentioned here in greater detail.

Likewise, the starting materials for the preparation of compounds of the present invention can be prepared by methods as described in the examples or by methods known per se, as described in the literature of synthetic organic chemistry and known to the skilled person, or can be obtained commercially. The starting materials for the processes described and/or utilized may, if desired, also be formed in situ by not isolating them from the reaction mixture, but instead immediately converting them further into the compounds of the invention or intermediate compounds. On the other hand, in general it is possible to carry out the reaction stepwise.

Preferably, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methyl pyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents or mixtures with water.

The reaction temperature is between about −100° C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilizing the procedures described herein, in conjunction with ordinary skills in the art, additional compounds of the present invention described herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The present invention also refers to a process for manufacturing a compound of formula I-a, I-b or I-c in its most general form as well as any of the particular embodiments, PE1, PE2, PE3, PE3a, PE3b, PE4, PE5, PE5a, PE5b, PE6, PE6a, PE6b, PE6c, PE7, PE7a, PE7b, PE7c, PE8, PE8a, PE8b, PE8c, PE9 described herein, or derivatives, N-oxides, prodrugs, solvates, tautomers or stereoisomers thereof as well as the pharmaceutically acceptable salts of each of the foregoing, the process being characterized in that (a) in case of a tetrazole-1H-imidazo[4.5-b]pyridine derivative of formula I-a the carbonitrile of general formula II-a (II-a)

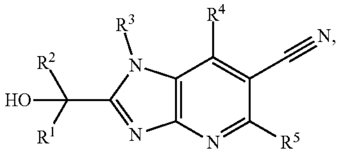

wherein $R^1$, $R^2$, $R^3$, $R^4$ and $R^5$ are as described for formula I-a above, is subjected to a cyclization reaction with a suitable azide reagent, e.g. sodium azide, optionally in the presence of a suitable catalyst, e.g. zinc chloride, to yield the tetrazole derivative of formula I-a:

(I-a)

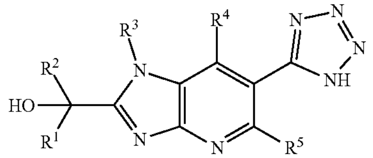

wherein $R^1$, $R^2$, $R^3$, $R^4$ and $R^5$ are as described for formula I-a above;

or (b) in case of a tetrazole-1-pyrazolo[1,5-a]pyridine derivative of formula I-b the carbonitrile of general formula II-b (II-b)

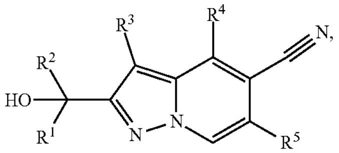

wherein $R^1$, $R^2$, $R^3$, $R^4$ and $R^5$ are as described for formula I-b above, is subjected to a cyclization reaction with a suitable azide reagent, e.g. sodium azide, optionally in the presence of a suitable catalyst, e.g. zinc chloride, to yield the tetrazole derivative of formula I-b:

(I-b)

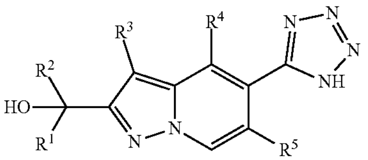

wherein $R^1$, $R^2$, $R^3$, $R^4$ and $R^5$ are as described for formula I-a above;

or (c) in case of a tetrazole-imidazo[1,2-a]pyridine derivative of formula I-c the carbonitrile of general formula II-c (II-c)

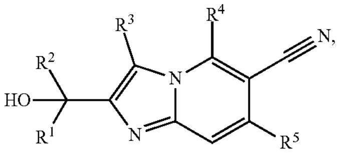

wherein $R^1$, $R^2$, $R^3$, $R^4$ and $R^5$ are as described for formula I-a above, is subjected to a cyclization reaction with a suitable azide reagent, e.g. sodium azide, optionally in the presence of a suitable catalyst, e.g. zinc chloride, to yield the tetrazole derivative of formula I-c:

(I-c)

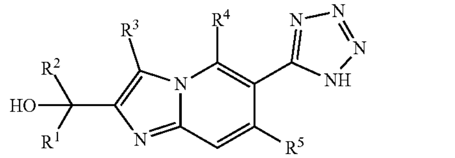

wherein $R^1$, $R^2$, $R^3$, $R^4$ and $R^5$ are as described for formula I-a above.

protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

In the following general synthetic routes that may be utilized to prepare compounds of the present invention are described in more detail in Schemes A to E:

Scheme A

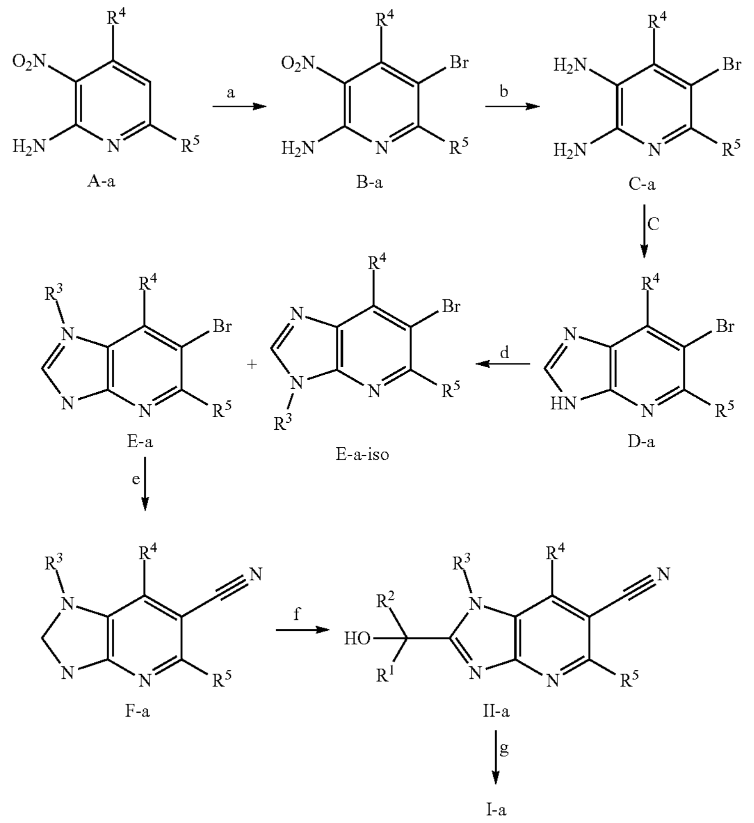

As will be understood by the person skilled in the art of organic synthesis compounds of the present invention, in particular compounds of formula I-a, I-b or I-c, are readily accessible by various synthetic routes, some of which are exemplified in the accompanying Experimental Part. The skilled artisan will easily recognize which kind of reagents and reactions conditions are to be used and how they are to be applied and adapted in any particular instance—wherever necessary or useful—in order to obtain the compounds of the present invention. Furthermore, some of the compounds of the present invention can readily be synthesized by reacting other compounds of the present invention under suitable conditions, for instance, by converting one particular functional group being present in a compound of the present invention, or a suitable precursor molecule thereof, into another one by applying standard synthetic methods, like reduction, oxidation, addition or substitution reactions; those methods are well known to the skilled person. Likewise, the skilled artisan will apply—whenever necessary or useful—synthetic protecting (or protective) groups; suitable Schema A above depicts a general synthesis route for preparing tetrazole compounds of formula I-a. The 2-amino-3-nitro-pyridine derivative A-a, which is readily available by utilizing well-know synthetic methods or through commercial sources, is converted into the 5-bromo-substituted derivative B-a by means of a suitable bromination reaction (step a), for instance, by using N-bromo succinimide (NBS), preferably in slight excess of about 1.05 to 1.15 equivalents related to A-a, in a suitable solvent, e.g., dimethylformamide (DMF). The nitro-substituent of the bromo-substituted pyridine derivative B-a may then be converted into an amino-group by means of a reduction reaction (step b) with gaseous hydrogen in the presence of a suitable metal catalyst, e.g., a sponge nickel catalyst, thereby yielding 2,3-diamino-5-bromo-substituted pyridine derivative C-a. This derivative may be isolated or, preferably, be reacted without isolation with a reaction partner that is suitable for the desired cyclization under adequate reaction conditions to yield the 3H-imidazo[4.5-b]pyridine derivative of formula D-a (step c); such reaction partner and conditions, respectively, can be, for instance, addition of triethyl orthoformate and formic acid and subsequent heating. After usual work-up compound D-a is obtained which can subsequently be converted into 1H-imidazo[4.5-b]pyridine derivative of formula E-a as well as its regioisomer E-a-iso (step d). An example for such a conversion into E-a (and E-a-iso) is the alkylation with a suitable alkylhalogenide, $R^3$—Hal, for instance alkyliodide in the presence of a strong base, e.g. sodium hydride, with subsequent neutralization with, e.g., ammonium chloride solution. Usually the desired regioisomer E-a is obtained as the major product and the other isomer E-a-iso as the minor product which products are subsequently be separated by usual techniques, e.g., chromatography on silica gel. 1H-imidazo[4.5-b]pyridine derivative E-a is then converted into the carbonitrile derivative of formula F-a by bromine/cyanide exchange (step e); this exchange can, for instance, be effected by adding $K_4[Fe(CN)_6]$ and potassium acetate in a suitable solvent, e.g. dioxane, and then adding a suitable catalyst, e.g. an appropriate palladium catatyst like tBuBrett-Phos Pd G3 and subsequently heating the resulting reaction mixture. Carbonitrile F-a may then be converted into the tertiary alcohol II-a by reacting the carbonitrile with a ketone of formula $R^1$—C(═O)—$R^2$ (wherein $R^1$ and $R^2$ are as defined for tetrazoles of formula I-a and may be the same or different) in the presence of a strong base (step f), e.g., lithium dimethylsilylamide in a suitable solvent, e.g. THF. In a final step (step g) the desired tetrazole derivative I-a may be obtained by subjecting the compound of formula II-a to a suitable azide reagent, e.g. sodium azide in the presence of zinc chloride or azidotributylstannane.

Tetrazole compounds of formual I-b with $R^1$ and $R^2$ being identical are readily available via the synthetic route depicted in Scheme B above: 2-propyl-4-carbonitrile substituted pyridine derivative A-b, which is available either from commercial sources or via synthetic procedures well-known to the skilled artisan, is converted into the respective 1-amino-pyridinium compound B-b by using a suitable reagent, e.g., amino 2,4,6-trimethylbenzene-1-sulfonate in dichormethan (step a). B-b is then subjected to a cyclization reaction under typical conditions with an appropriate reaction partner like ethyl oxalochloridate ($H_5C_2O$—C(═O)—C(═O)—Cl) to yield the pyrazolo[1,5-a]pyridine derivative C-b (step b). C-b may then be converted into the tertiary alcohol II-b by reacting with a suitable C-nucleophile, for instance, in a classical Grignard reaction with, e.g., $R^1$—Mg—Cl (or $R^2$—Mg—Cl) (step c). Simliar to step g in Scheme A the carbontrile II-b is converted into the desired tetrazole of formula I-b by reacting it with a suitable azide reagent, e.g., sodium azide in the presence of zinc chloride or azidotributylstannane.

Scheme B

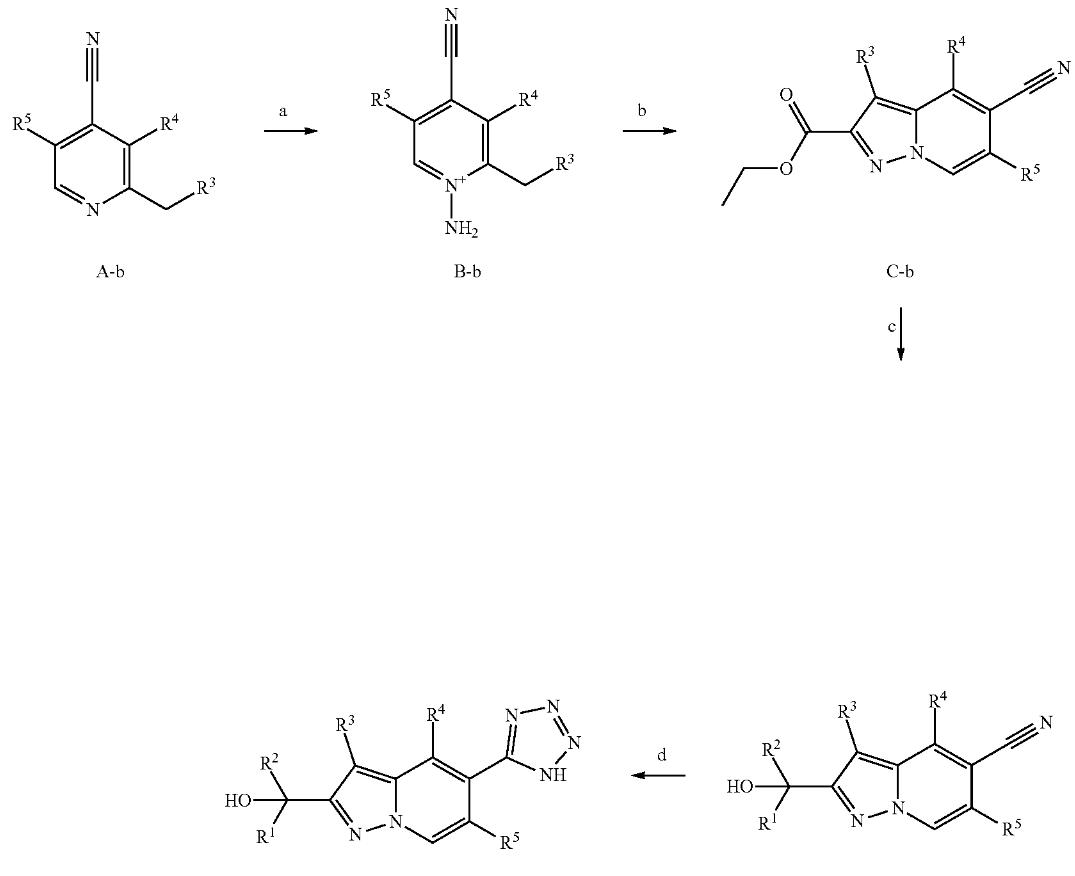

A-b B-b C-b

I-b II-b

Scheme C

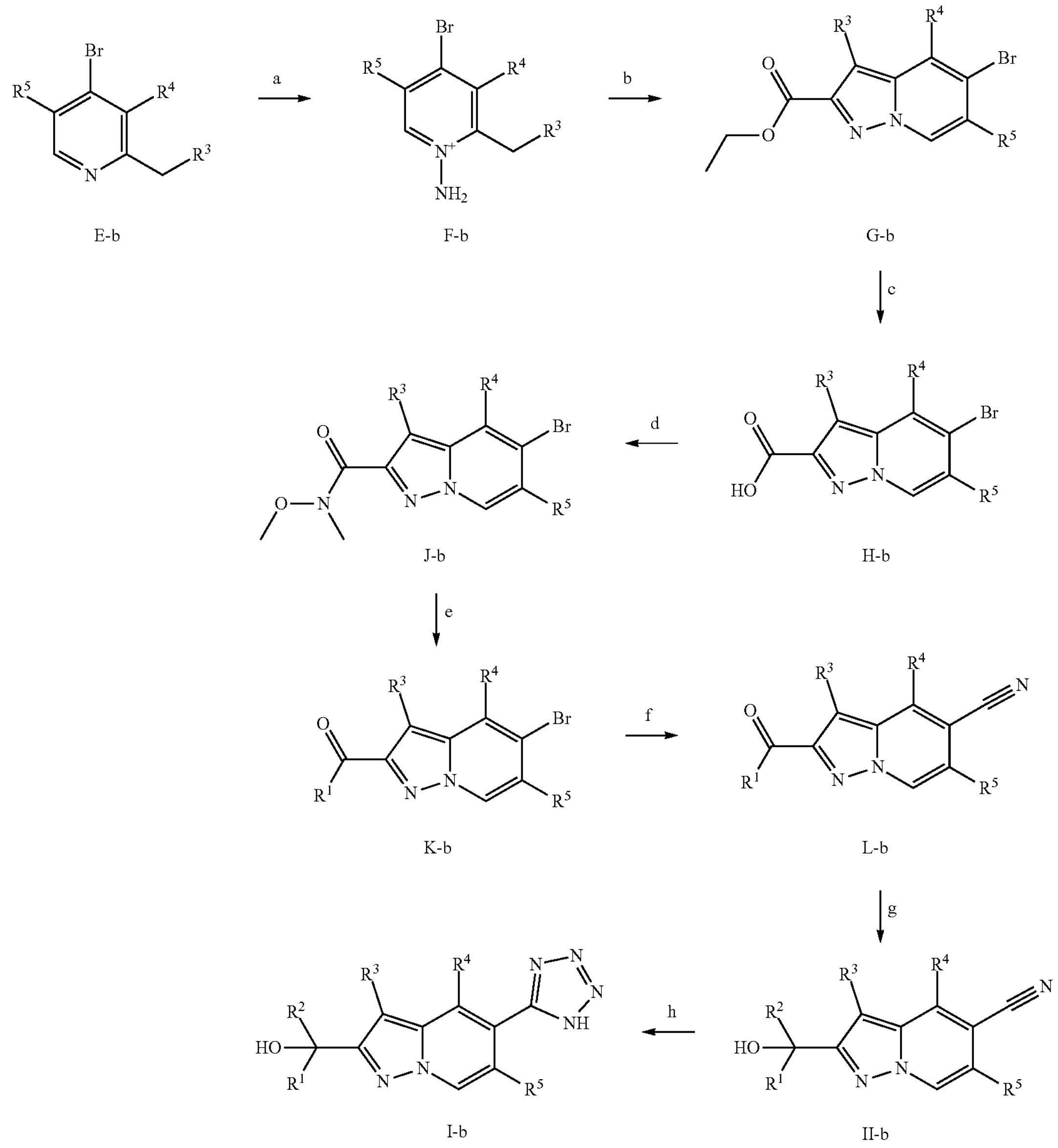

E-b F-b G-b H-b J-b K-b L-b I-b II-b

Tetrazole compounds of formual I-b with $R^1$ and $R^2$ not being identical but different are readily available via the synthetic route depicted in Scheme C above: 2-propyl-4-bromo substituted pyridine derivative E-b, which is available either from commercial sources or via synthetic procedures well-known to the skilled artisan, is converted into the respective 1-amino-pyridinium compound F-b by using a suitable reagent, e.g., amino 2,4,6-trimethylbenzene-1-sulfonate in dichormethan (step a). F-b is then subjected to a cyclization reaction under typical conditions with an appropriate reaction partner like ethyl oxalochloridate ($H_5C_2$—O—C(═O)—C(═O)—Cl) to yield the pyrazolo[1,5-a]pyridine derivative G-b (step b). G-b is then converted into its carboxylic acid H-b under usual saponification conditions, e.g., by adding a base, for instance LiOH, NaOH or KOH. That carboxylic acid H-b is subsequently converted into the carboxamide J-b in a reaction with methoxy(methyl)amine hydrochloride under appropriate conditions, for instance, in the presence of EDC N-(3-dimethylaminopropyl)-N'-ethylcarbodiimide hydrochloride, HOBt (1-hydroxybenzotriazole) and an amine base like triethylamine. Carboxamide J-b can then be reacted with 1 equivalent of a suitable Grignard reagent $R^1$—Mg-Hal to provide the ketone K-b (step e). Subsequent bromine-cyanide exchange (step f) by reacting K-b, for instance, with $Zn(CN)_2$ and a Palladium catalyst like $Pd_2(dba)_3$ and XantPhos in DMF yields carbonitrile L-b which in turn is reacted with a suitable organometallic compound, e.g., $R^2$—Li—that may be prepared in situ by reacting the appropriate halogenide $R^2$-Hal with a suitable lithium-organic base, e.g., n-butyl lithium—to provide the tertiary alcohol II-b (step g). That compound II-b is finally converted (step h) into the desired tetrazole derivative of formula I-b by reacting with an azide reagent, e.g., sodium azide or in the presence of zinc chloride or azidotributylstannane, as described for Schemes A and B.

Scheme D

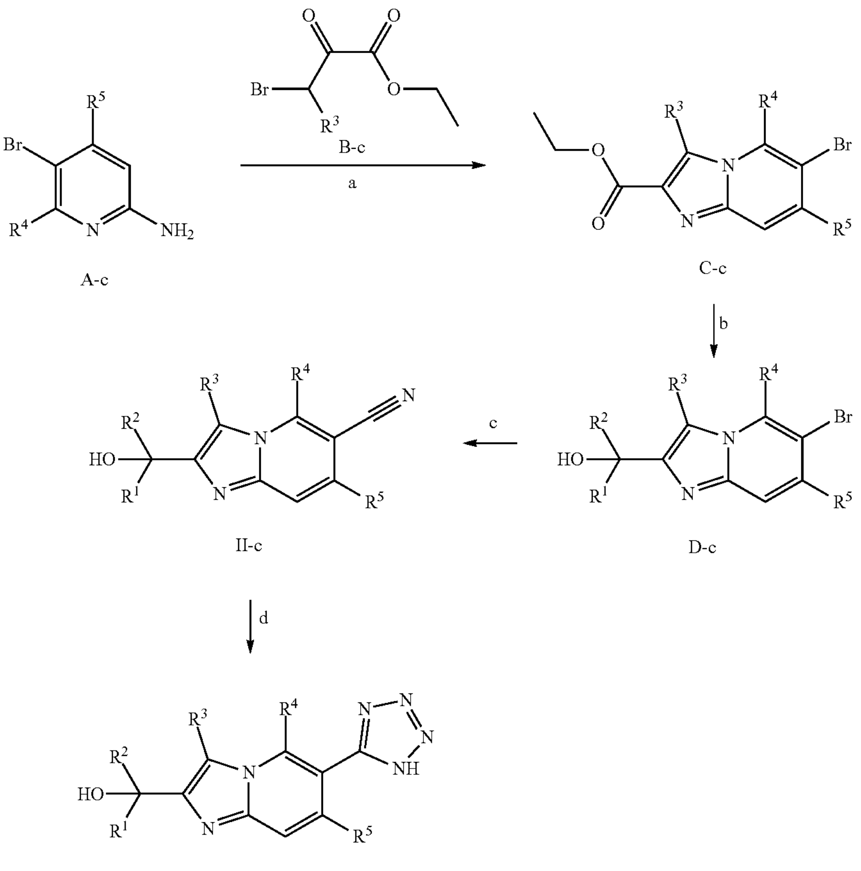

Tetrazole compounds of formula I-c with $R^1$ and $R^2$ being identical are readily available via the synthetic route depicted in Scheme D above: 2-amino-5-bromo-substituted pyridine derivative A-c, which is available either from commercial sources or via synthetic procedures well-known to the skilled artisan, is subjected to a cyclization reaction under typical conditions with an appropriate reaction partner like substituted alpha-halogen-oxalic acid ethyl esters ($C_2H_5$—O—C(═O)—C(═O)—CHHal-$R^3$, e.g. $C_2H_5$—O—C(═O)—C(═O)—CHBr—$C_2H_5$ if Hal=Br and $R^3$=ethyl (B-c)) to yield the imidazo[1,2-a]pyridine derivative C-c (step a). C-c is subsequently converted into the tertiary alcohol D-c by reacting C-c with a suitable C-nucleophile, for instance, in a classical Grignard reaction with, e.g., $R^1$—Mg—Cl (or $R^2$—Mg—Cl) (step b). Subsequent bromine-cyanide exchange (step c) by reacting D-c, for instance, with $Zn(CN)_2$ and a Palladium catalyst like $Pd(PPh_3)_4$ in DMF yields carbonitrile II-c which is then converted (step d) into the desired tetrazole of formula I-c by reacting II-c with a suitable azide reagent, e.g., sodium azide in the presence of zinc chloride or azidotributylstannane.

Scheme E

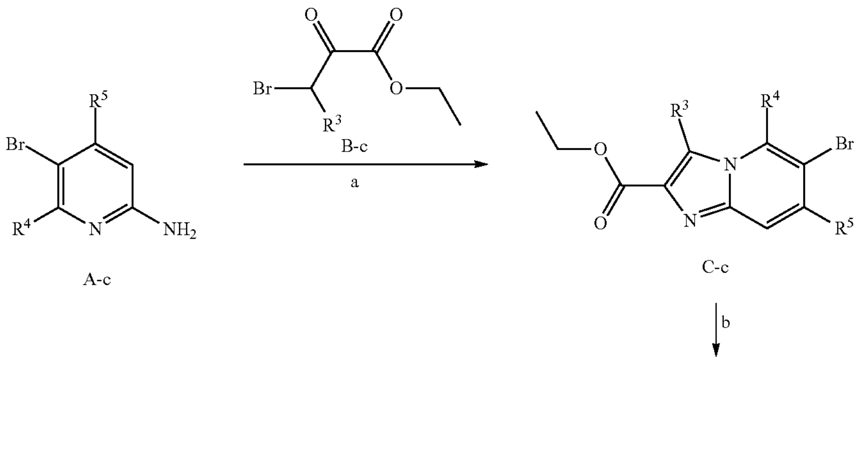

-continued

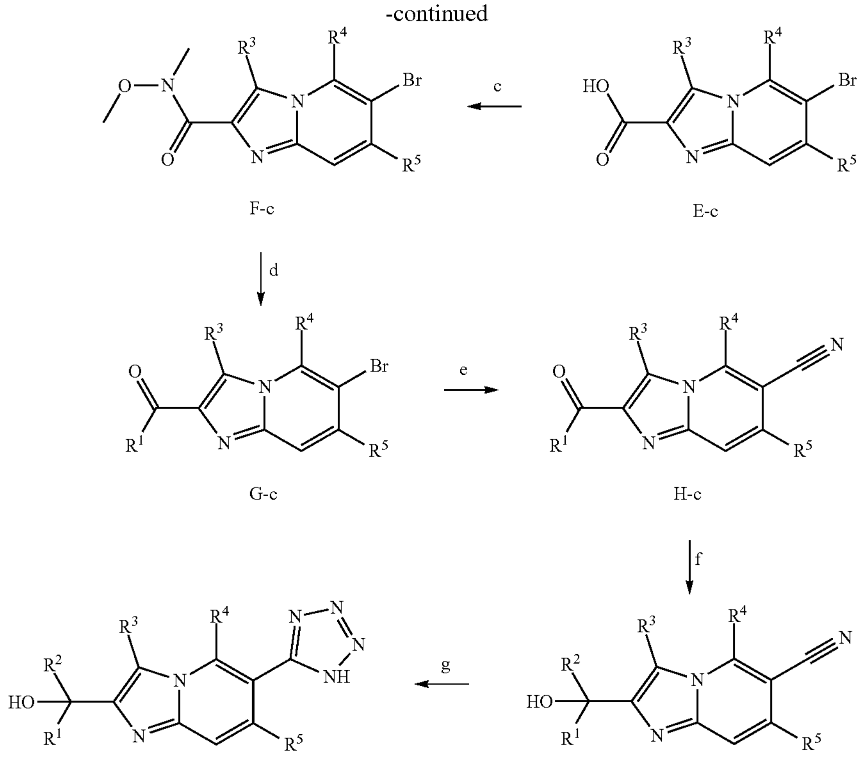

F-c E-c G-c H-c I-c II-c

Tetrazole compounds of formula I-c with $R^1$ and $R^2$ not being the same but different are readily available via the synthetic route depicted in Scheme E above: As shown in and described for Scheme D 2-amino-5-bromo-substituted pyridine derivative A-c is converted into the imidazo[1,2-a]pyridine derivative C-c (step a). Ester C-c is then converted into its carboxylic acid E-c under usual saponification conditions, e.g., by adding a base, for instance LiOH, NaOH or KOH (step b). That carboxylic acid E-c is subsequently converted into the carboxamide F-c in a reaction with methoxy(methyl)amine hydrochloride under appropriate conditions, for instance, in the presence of EDC N-(3-dimethylaminopropyl)-N'-ethylcarbodiimide hydrochloride, HOBt (1-hydroxybenzotriazole) and an amine base like triethylamine (step c). Carboxamide F-c can then be reacted with 1 equivalent of a suitable Grignard reagent $R^1$—Mg-Hal to provide the ketone G-c (step d). Subsequent bromine-cyanide exchange (step e) by reacting K-b, for instance, with $Zn(CN)_2$ in the presence of a Palladium catalyst like $Pd_2(dba)_3$ and XantPhos in DMF yields carbonitrile H-c which in turn is reacted with a suitable organometallic compound, e.g., $R^2$—Li—that may be prepared in situ by reacting the appropriate halogenide $R^2$-Hal with a suitable lithium-organic base, e.g., n-butyl lithium—to provide the tertiary alcohol II-c (step f). That compound II-c is finally converted (step g) into the desired tetrazole dervivative of formula I-c by reacting with an azide reagent, e.g., sodium azide or in the presence of zinc chloride or azidotributylstannane, as described, e.g., for Schemes A and B.

The present invention also refers to carbonitriles of formula II-a, II-b or II-c which are useful intermediates for making tetrazoles of the present invention of formula I-a, I-b or I-c, respectively:

II-a

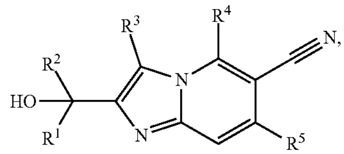

II-b

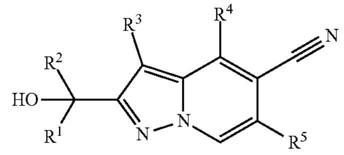

II-c

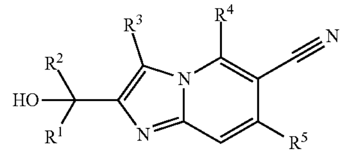

wherein $R^1$, $R^2$, $R^3$, $R^4$ and $R^5$ are as defined above for formulas I-a, I-b and I-C.

"Treating" ot "treatment" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a tetrazole of formula I-a, I-b or I-c refers to an amount (of a compound, drug, pharmaceutical compositions, etc.) capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer or metabolic conditions.

It is to be noted that—except for instances where it is specifically stated or the context provides for a different meaning—in general the number of a term, i.e. its singular and plural form, is used and can be read interchangeably. For example, the term "compound" in its singular form may also comprise or refer to a plurality of compounds, while the term "compounds" in its plural form may also comprise or refer to a singular compound.

EXPERIMENTAL PART

Abbreviations

The compounds of the present invention can be prepared according to the procedures of the following Schemes and Examples, using appropriate materials and are further exemplified by the following specific examples. The compounds are shown in Table 1 which is divided in Tables 1a, 1b, 1c, 1d, 1e, 1f, 1g, 1h, 1i and 1j. Analytical data of compounds made according to the following examples are shown in Table 1 (Tables 1a, 1b, 1c, 1d, 1e, 1f, 1g, 1h, 1i and 1j) too.

The invention will be illustrated, but not limited, by reference to the specific embodiments described in the following examples. Unless otherwise indicated in the schemes, the variables have the same meaning as described above.

Unless otherwise specified, all starting materials are obtained from commercial suppliers and used without further purifications. Unless otherwise specified, all temperatures are expressed in ° C. and all reactions are conducted at RT (room temperature). Compounds are purified by either silica chromatography or preparative HPLC.

$^1$H NMR:

$^1$H-NMR data is provided in Table 1 below. $^1$H NMR spectra were usually acquired on a Bruker Avance DRX 500, Bruker Avance 400 or a Bruker DPX 300 NMR spectrometer under standard conditions using TMS (tetramethylsilan) as internal reference and DMSO-d6 as standard solvents, if not reported otherwise. NS (Number of Scans): 32, SF (Spectrometer Frequence) as indicated. TE (Temperatur): 297 K. Chemical shifts (δ) are reported in ppm relative to the residual solvent signal (δ=2.5 ppm for $^1$H NMR in DMSO-d6, δ=7.27 ppm for $^1$H NMR in $CDCl_3$, δ=3.31 ppm for Methanol-d4). $^1$H NMR data are reported as follows: chemical shift (multiplicity, coupling constants and number of hydrogens). Multiplicity is abbreviated as follows: s (singlet), d (doublet), t (triplet), q (quartet), m (multiplet), dd (doublet of doublets), tt (triplet of triplets), td (triplet of doublets) br (broad) and coupling constants (J) are reported in Hz.

HPLC-MS:

HPLC-MS data provided in Table 1 are given with mass in m/z. The results can be obtained by one of the methods described below. HPLC-MS analyses were usually performed on a Shimadzu LCMS-2020, Shimadzu SP-M20A 2010EV or Shimadzu UFLC-MS 2010EV system utilizing one of the following columns: Shim-pack VP-ODS, Shim-pack XR-ODS, Kinetex XB-C18 100A, Xbridge BEH C18, Gemini-NX 3u C18 110A or ACE UltraCore 2.5 SuperC18.

Standard conditions applied:

Standard Solvent Gradients Using

A: Water+0.1 vol. % formic acid, B: acetonitrile+0.1 vol. % formic acid; or

A: Water+0.05 vol. % trifluoroacetic acid, B: acetonitrile+0.05 vol. % trifluoroacetic acid Detection wavelength: 220 nm, MS-Typ: API-ES General Synthesis 1

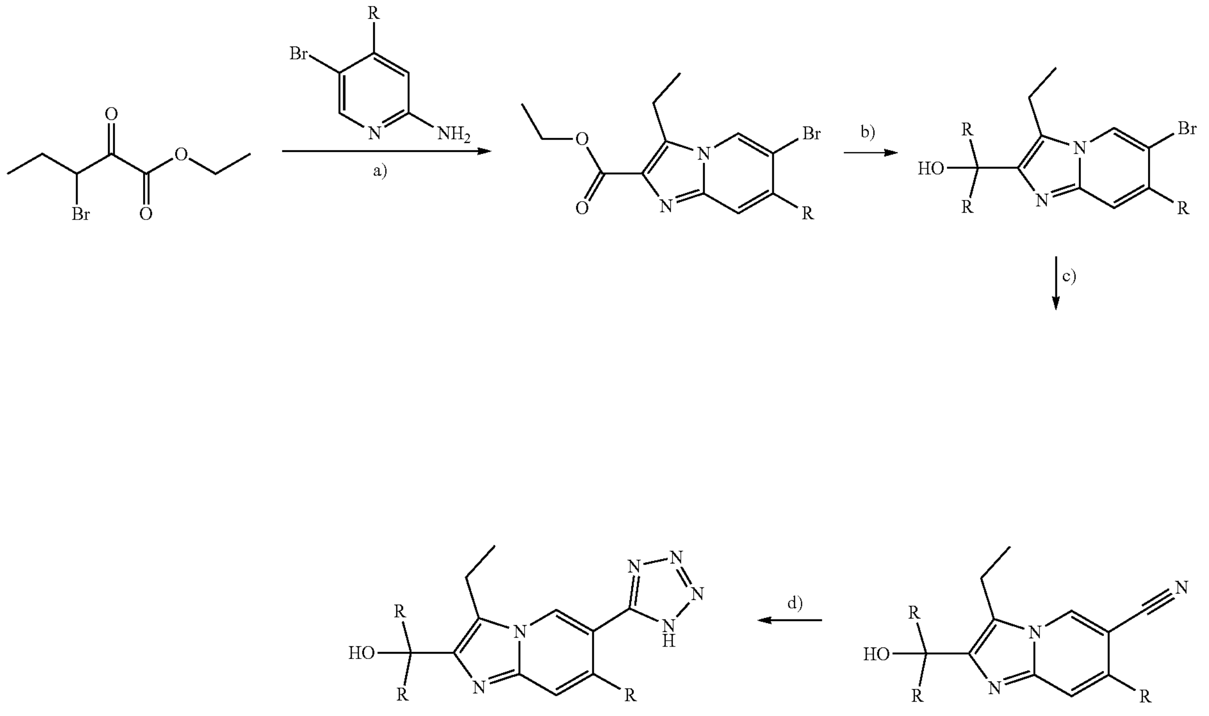

Example 1

[3-Ethyl-7-methoxy-6-(1H-tetrazol-5-yl)-imidazo[1,2-a]pyridin-2-yl]-diphenyl-methanol

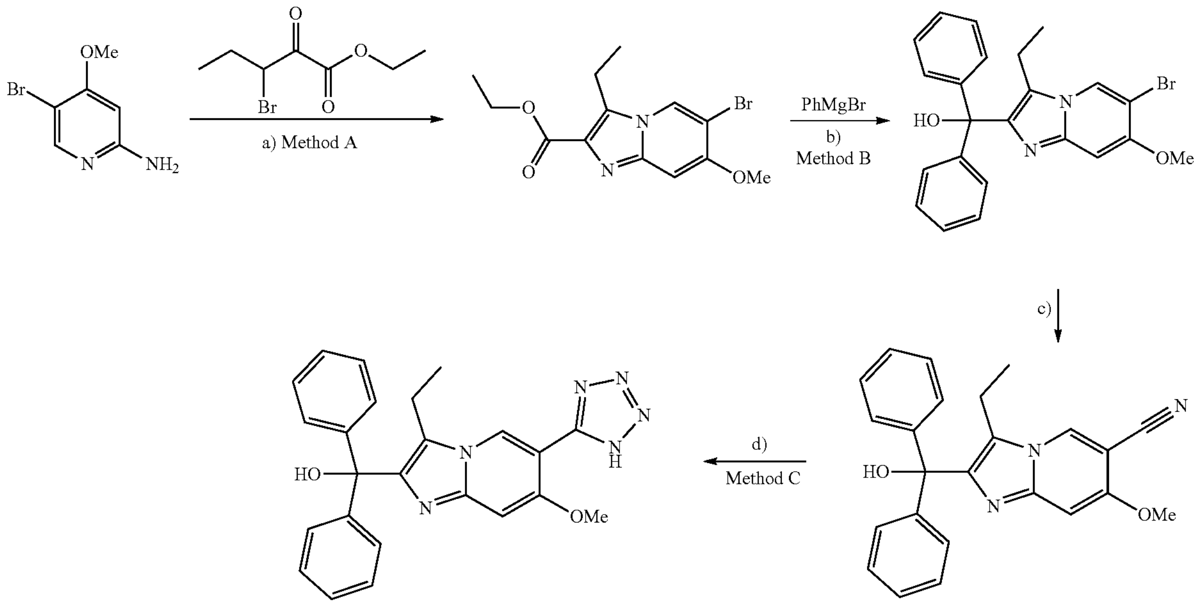

a) Method A: A mixture of 5-bromo-4-methoxypyridin-2-amine (4 g, 19.70 mmol) and ethyl 3-bromo-2-oxopentanoate (8 g, 35.86 mmol) in EtOH (40 mL) was stirred at 80° C. for 16 h. Then the reaction mixture was cooled to room temperature and the pH value was adjusted to 8 with $NaHCO_3$. The mixture was diluted with water (100 mL) and extracted with DCM (100 mL×3). The combined organic phases were washed with brine and dried over $Na_2SO_4$. The solvent was removed under reduced pressure and the residue was purified by flash chromatography eluting with EtOAc in petroleum ether (5% to 30% gradient) to yield ethyl 6-bromo-3-ethyl-7-methoxyimidazo[1,2-a]pyridine-2-carboxylate as light yellow solid (2.8 g, 38%). LC/MS: $[M+H]^+$ 327.1/329.1.

b) Method B: To a solution of ethyl 6-bromo-3-ethyl-7-methoxyimidazo[1,2-a]pyridine-2-carboxylate (1.3 g, 3.97 mmol) in THF (130 mL) was added PhMgBr (1 M in THF, 11.9 mL, 11.9 mmol) dropwise at 0° C. The resulting mixture was kept stirring at 0° C. for 1 h. Then the reaction mixture was carefully quenched with saturated $NH_4Cl$ solution (20 mL) and diluted with water (100 mL). The aqueous phase was extracted with DCM (150 mL×2) and the organic phases were combined, washed with brine and dried over $Na_2SO_4$. The solvent was removed under reduced pressure and the residue was purified by flash chromatography eluting with MeOH in DCM (1% to 5% gradient) to yield [6-bromo-3-ethyl-7-methoxyimidazo[1,2-a]pyridin-2-yl]diphenylmethanol as yellow solid (1.4 g, 80%). LC/MS $[M+H]^+$ 437.1/439.1.

c) A mixture of [6-bromo-3-ethyl-7-methoxyimidazo[1,2-a]pyridin-2-yl]diphenylmethanol (100 mg, 0.22 mmol), $Zn(CN)_2$ (27 mg, 0.23 mmol) and $Pd(PPh_3)_4$ (53 mg, 0.046 mmol) in DMF (5 mL) was stirred for 2 h at 120° C. under nitrogen atmosphere. Then the reaction mixture was diluted with water (20 mL) and extracted with DCM (30 mL×3). The organic phases were combined, washed with brine and dried over $Na_2SO_4$. The solvent was removed under reduced pressure and the residue was purified by flash chromatography eluting with EtOAc in petroleum ether (20% to 80% gradient) to yield 3-ethyl-2-(hydroxydiphenylmethyl)-7-methoxyimidazo[1,2-a]pyridine-6-carbonitrile as yellow solid (50 mg, 57%). LC/MS $[M+H]^+$ 384.3.

d) [3-Ethyl-7-methoxy-6-(1H-1,2,3,4-tetrazol-5-yl)imidazo[1,2-a]pyridin-2-yl]diphenylmethanol was prepared from 3-ethyl-2-(hydroxydiphenylmethyl)-7-methoxyimidazo[1,2-a]pyridine-6-carbonitrile and azidotributylstannane using Method C. The final product was purified by prep-HPLC under the following conditions: column, XBridge Shield RP18 OBD Column, 30×150 mm, 5 µm; mobile phase, MeCN in water (with 10 mM $NH_4HCO_3$ and 0.1% $NH_3 \cdot H_2O$), 5% to 45% gradient in 8 min; detector, UV 254/220 nm to yield [3-Ethyl-7-methoxy-6-(1H-1,2,3,4-tetrazol-5-yl)imidazo[1,2-a]pyridin-2-yl]diphenylmethanol as a white solid (12.5 mg, 22.5%). LC/MS $[M+H]^+$ 427.0.

Example 2

[3-Ethyl-7-methoxy-6-(1H-tetrazol-5-yl)-imidazo[1,2-a]pyridin-2-yl]-bis-(2-fluoro-phenyl)-methanol

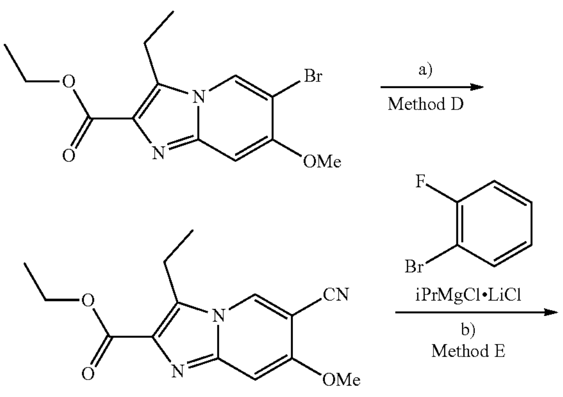

-continued

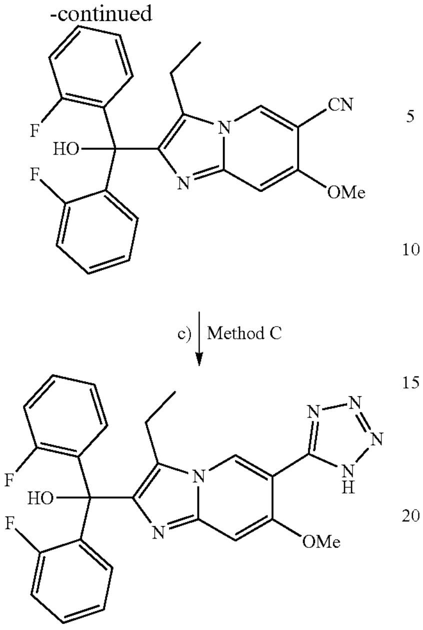

a) Method D: A mixture of ethyl 6-bromo-3-ethyl-7-methoxyimidazo[1,2-a]pyridine-2-carboxylate (1.5 g, 4.58 mmol), $Zn(CN)_2$ (0.3 g, 2.51 mmol), $Pd_2(dba)_3$ (1.2 g, 1.3 mmol) and XantPhos (0.7 g, 1.3 mmol) in DMF (30 mL) was stirred for 3 h at 90° C. under nitrogen atmosphere. Then the reaction mixture was diluted with water and extracted with $CH_2Cl_2$. The organic phases were combined, washed with brine and dried over $Na_2SO_4$. The solvent was removed under reduced pressure and the residue was purified by flash chromatography eluting with MeOH in DCM (1% to 7% gradient) to yield ethyl 6-cyano-3-ethyl-7-methoxyimidazo[1,2-a]pyridine-2-carboxylate as yellow solid (1.2 g, 92%). LC/MS $[M+H]^+$ 274.1.

b) Method E: To a solution of 1-bromo-2-fluorobenzene (2.37 g, 13.54 mmol) in THF (30 mL) was added iPrMgCl·LiCl (10.4 mL, 1.3 M in THF) dropwise at −15° C. The resulting mixture was stirred at −15° C. for 2 h after which a solution of ethyl 6-cyano-3-ethyl-7-methoxyimidazo[1,2-a]pyridine-2-carboxylate (1.2 g, 4.40 mmol) in THF (10 mL) was added slowly. The reaction mixture was kept stirring at −15° C. for additional 2 h. Then the reaction mixture was carefully quenched with saturated $NH_4Cl$ solution (20 mL) and diluted with water (30 mL). The resulting mixture was extracted with DCM (80 mL×3) and the organic phases were combined, washed with brine and dried over $Na_2SO_4$. The solvent was removed under reduced pressure and the residue was purified by flash chromatography eluting with MeOH in DCM (1% to 5% gradient) to yield 2-[bis(2-fluorophenyl)(hydroxy)methyl]-3-ethyl-7-methoxyimidazo[1,2-a]pyridine-6-carbonitrile as yellow solid (900 mg, 44%). LC/MS $[M+H]^+$ 420.1.

c) [3-Ethyl-7-methoxy-6-(1H-1,2,3,4-tetrazol-5-yl)imidazo[1,2-a]pyridin-2-yl]bis(2-fluorophenyl)methanol was prepared from 2-[bis(2-fluorophenyl)(hydroxy)methyl]-3-ethyl-7-methoxyimidazo[1,2-a]pyridine-6-carbonitrile and azidotributylstannane using Method C. The final product was purified by prep-HPLC under the following conditions: column, XBridge Shield RP18 OBD Column, 30×150 mm, 5 μm; mobile phase, MeCN in water (with 10 mM $NH_4HCO_3$ and 0.1% $NH_3 \cdot H_2O$), 15% to 45% gradient in 8 min; detector, UV 254/220 nm. [3-Ethyl-7-methoxy-6-(1H-1,2,3,4-tetrazol-5-yl)imidazo[1,2-a]pyridin-2-yl]bis(2-fluorophenyl)methanol was obtained as white solid (15 mg, 42%). LC/MS $[M+H]^+$ 463.0.

Example 3

[7-Chloro-3-ethyl-6-(1H-1,2,3,4-tetrazol-5-yl)imidazo[1,2-a]pyridin-2-yl](phenyl)(pyridin-2-yl)methanol

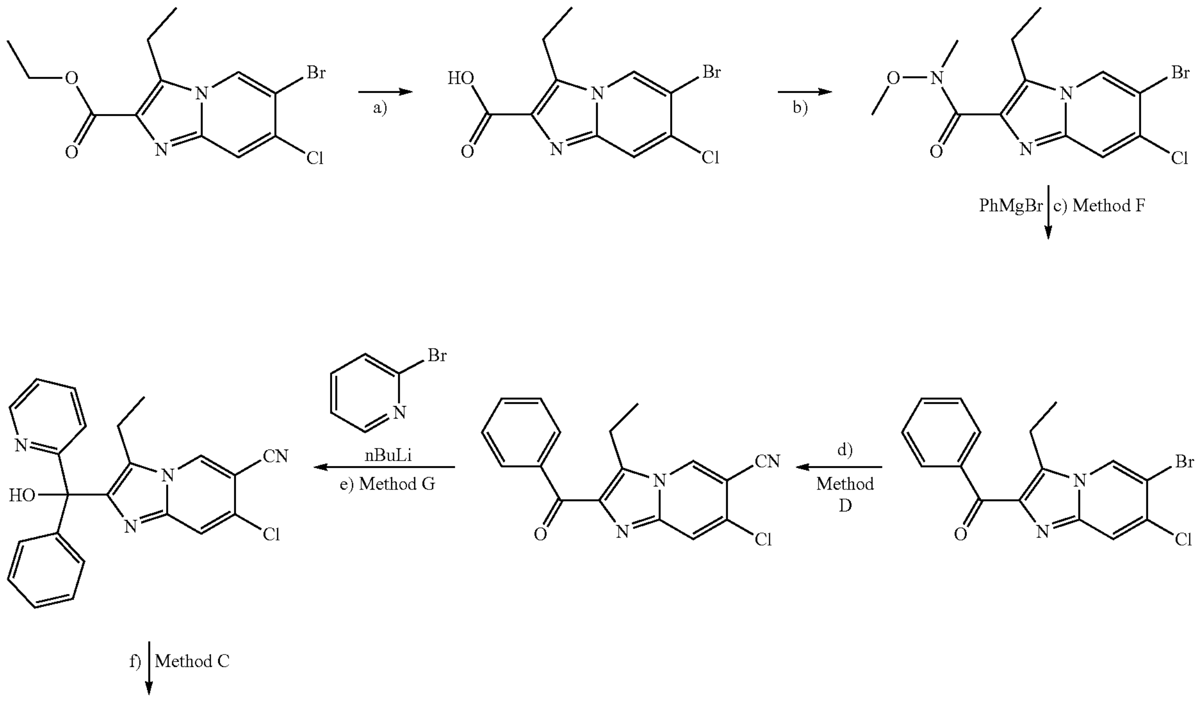

-continued

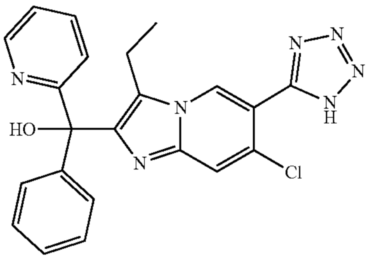

Ethyl 6-bromo-7-chloro-3-ethylimidazo[1,2-a]pyridine-2-carboxylate was prepared from 5-bromo-4-chloropyridin-2-amine using Method A.

a) To a solution of ethyl 6-bromo-7-chloro-3-ethylimidazo[1,2-a]pyridine-2-carboxylate (2.5 g, 7.54 mmol) in THF (50 mL) and $H_2O$ (10 mL) was added LiOH (632 mg, 26.4 mmol) in portions. The resulting mixture was stirred at room temperature for 16 h. Then the pH value of the reaction mixture was carefully adjusted to 5-6 with 6 M HCl aq. The organic solvent was removed under reduced pressure and the resulting solid was collected by filtration. The solid was washed with water and dried under high vacuum to yield 6-bromo-7-chloro-3-ethylimidazo[1,2-a]pyridine-2-carboxylic acid as yellow solid (2.1 g, 91%). LC/MS $[M+H]^+$ 302.8/304.8.

b) To a solution of 6-bromo-7-chloro-3-ethylimidazo[1,2-a]pyridine-2-carboxylic acid (2.1 g, 6.91 mmol) in $CH_2Cl_2$ (200 mL) was added N-(3-Dimethylaminopropyl)-N'-ethylcarbodiimide hydrochloride (2.65 g, 13.8 mmol), 1-hydroxybenzotriazole (1.87 g, 13.8 mmol), $NEt_3$ (2.8 g, 27.7 mmol), and methoxy(methyl)amine hydrochloride (2.02 g, 20.76 mmol). The reaction mixture was stirred at room temperature for 16 h. Then it was diluted with water and extracted with $CH_2Cl_2$. The combined organic phase was washed with brine and dried over $Na_2SO_4$. The solvent was removed under reduced pressure and the residue was purified by flash chromatography eluting with EtOAc in petroleum ether (5% to 50% gradient) to yield 6-bromo-7-chloro-3-ethyl-N-methoxy-N-methylimidazo[1,2-a]pyridine-2-carboxamide as yellow solid (1.5 g, 63%). LC/MS $[M+H]^+$ 345.8./347.9.

c) Method F: To a solution of 6-bromo-7-chloro-3-ethyl-N-methoxy-N-methylimidazo[1,2-a]pyridine-2-carboxamide (1.5 g, 4.33 mmol) in THF (200 mL) was added PhMgBr (5.8 mL, 1 M in THF) at −78° C. dropwise. The mixture was kept stirring at −78° C. for 2 h after which it was carefully quenched with saturated $NH_4Cl$ solution and diluted with water. The aqueous layer was extracted with $CH_2Cl_2$ and the combined organic phases were washed with brine and dried over $Na_2SO_4$. The solvent was removed under reduced pressure and the residue was purified by flash chromatography eluting with EtOAc in petroleum ether (10% to 50% gradient) to yield 2-benzoyl-6-bromo-7-chloro-3-ethylimidazo[1,2-a]pyridine as yellow solid (1.2 g, 72%). LC/MS $[M+H]^+$ 362.9./364.9 d) 2-benzoyl-7-chloro-3-ethylimidazo[1,2-a]pyridine-6-carbonitrile was prepared from 2-benzoyl-6-bromo-7-chloro-3-ethylimidazo[1,2-a]pyridine using Method D. LC/MS $[M+H]^+$ 310.0.

e) Method G: To a solution of 2-bromopyridine (893 mg, 5.65 mmol) in THF (100 mL) was added nBuLi (1.72 mL, 2.5 M in THF) at −78° C. dropwise. The resulting mixture was kept stirring at −78° C. for 1 h, followed by the slow addition of 2-benzoyl-7-chloro-3-ethylimidazo[1,2-a]pyridine-6-carbonitrile (700 mg, 2.26 mmol) in THF (20 mL). The mixture was kept stirring at −78° C. for additional 1 h after which it was carefully quenched with saturated $NH_4Cl$ solution and diluted with water. The aqueous layer was extracted with $CH_2Cl_2$ and the combined organic phases were washed with brine and dried over $Na_2SO_4$. The solvent was removed under reduced pressure and the residue was purified by flash chromatography eluting with MeOH in DCM (1% to 8% gradient) to yield 7-chloro-3-ethyl-2-[hydroxy(phenyl)(pyridin-2-yl)methyl]imidazo[1,2-a]pyridine-6-carbonitrile as yellow solid (500 mg, 53%). LC/MS $[M+H]^+$ 389.1.

f) [7-Chloro-3-ethyl-6-(1H-1,2,3,4-tetrazol-5-yl)imidazo[1,2-a]pyridin-2-yl](phenyl)(pyridin-2-yl)methanol was prepared from 7-chloro-3-ethyl-2-[hydroxy(phenyl)(pyridin-2-yl)methyl]imidazo[1,2-a]pyridine-6-carbonitrile and azidotributylstannane using Method C.

Example 4

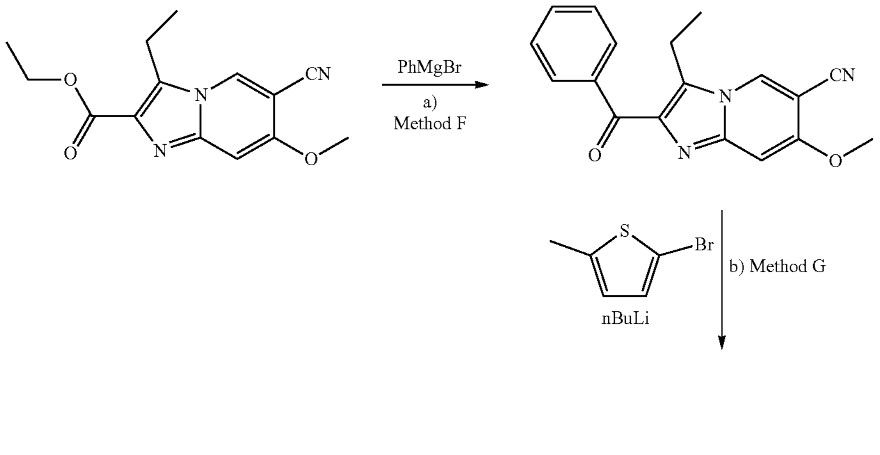

-continued

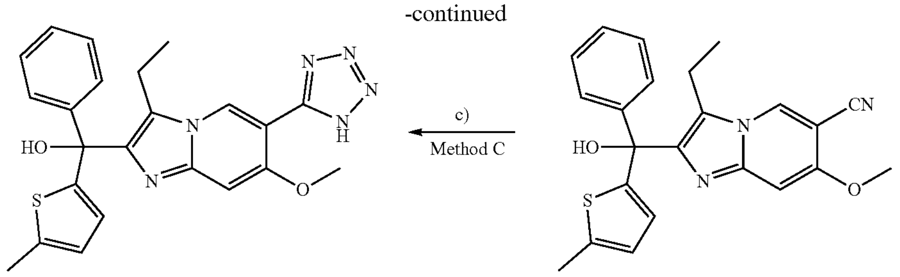

[3-ethyl-7-methoxy-6-(1H-1,2,3,4-tetrazol-5-yl)imidazo[1,2-a]pyridin-2-yl](phenyl)(pyridin-2-yl)methanol was prepared from ethyl 6-cyano-3-ethyl-7-methoxyimidazo[1,2-a]pyridine-2-carboxylate using Methods F, G and C.

Example 5

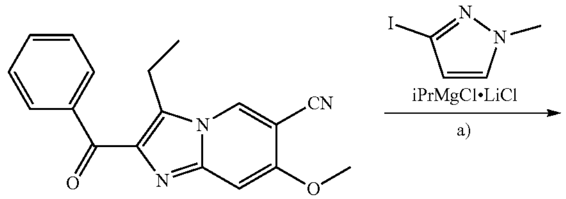

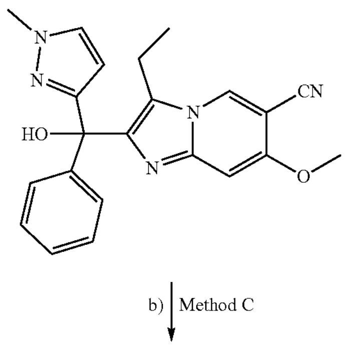

-continued

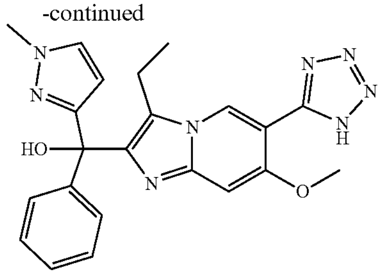

a) To a solution of 3-iodo-1-methyl-1H-pyrazole (3.96 g, 19.0 mmol) in THF (100 mL) was added dropwise iPrMgCl·LiCl (11.6 mL, 1.3 M in THF) at −15° C. The mixture was kept stirring at −15° C. for 1 h after which it was cooled down to −70° C. 2-Benzoyl-3-ethyl-7-methoxy-imidazo[1,2-a]pyridine-6-carbonitrile (2.00 g, 6.55 mmol) in THF (40 mL) was slowly added to the reaction mixture. The reaction was warmed up to 0° C. and stirred for 2 h. The reaction was carefully quenched with saturated $NH_4Cl$ solution and diluted with water. The aqeuous layer was extracted with $CH_2Cl_2$ and the combined organic phases were washed with brine and dried over $Na_2SO_4$. The solvent was removed under reduced pressure and the residue was purified by flash chromatography eluting with MeOH in $CH_2Cl_2$ (1% to 8% gradient) to yield 3-ethyl-2-[hydroxy(1-methyl-1H-pyrazol-3-yl)phenylmethyl]-7-methoxyimidazo[1,2-a]pyridine-6-carbonitrile as yellow solid (1.10 g, 40%). LC/MS $[M+H]^+$ 388.1.

b) [3-ethyl-7-methoxy-6-(1H-1,2,3,4-tetrazol-5-yl)imidazo[1,2-a]pyridin-2-yl](1-methyl-1H-pyrazol-3-yl)phenylmethanol was prepared from 3-ethyl-2-[hydroxy(1-methyl-1H-pyrazol-3-yl)phenylmethyl]-7-methoxyimidazo[1,2-a]pyridine-6-carbonitrile using Method C.

General Synthesis 2

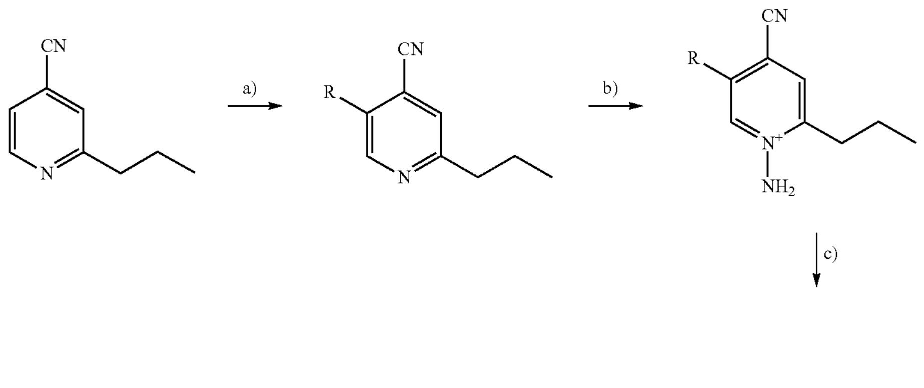

-continued

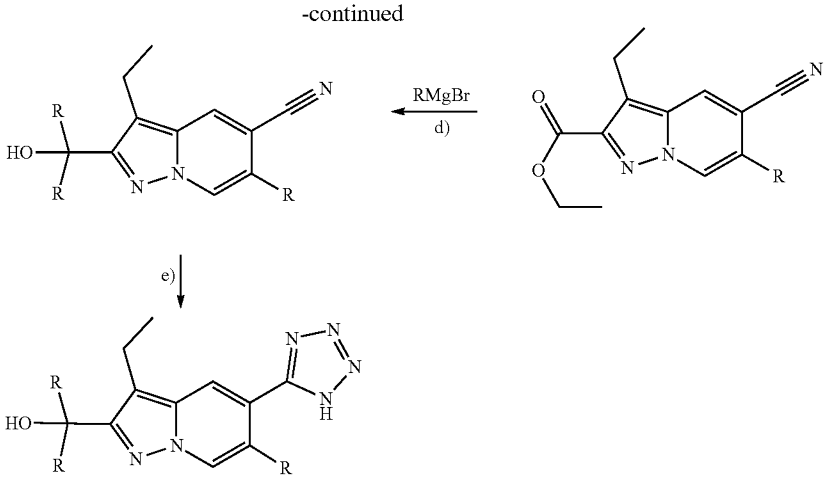

Example 6

[3-Ethyl-6-methoxy-5-(1H-tetrazol-5-yl)-pyrazolo[1,5-a]pyridin-2-yl]-diphenyl-methanol

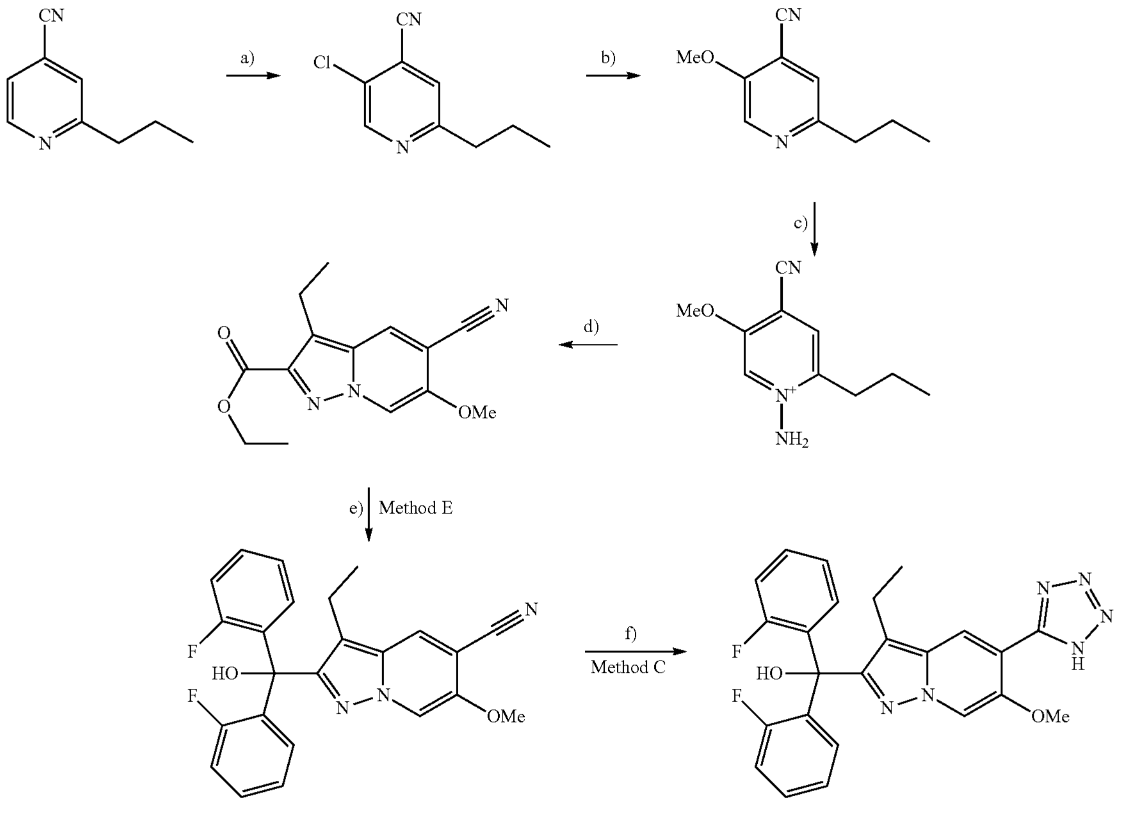

a) To a solution of 2,2,6,6-tetramethylpiperidine (15 g, 106.19 mmol) in THF (250 mL) was added nBuLi (42.5 mL, 2.5 M) at −30° C. dropwise. The resulting mixture was stirred at −30° C. for 30 min and then cooled to −78° C. A solution of 2-propylpyridine-4-carbonitrile (7.8 g, 53.36 mmol) in THF (20 mL) was added slowly to the mixture. The reaction mixture was stirred at −78° C. for 30 min after which hexachloroethane (25 g, 105.6 mmol) was added slowly. The reaction mixture was slowly warmed to room temperature and stirred at room temperature for 30 min. Then the reaction mixture was carefully quenched with saturated $NH_4Cl$ solution (100 mL) and diluted with water (300 mL). The resulting mixture was extracted with EtOAc (300 mL×3) and the organic phases were combined, washed with brine and dried over $Na_2SO_4$. The solvent was removed under reduced pressure and the residue was purified by flash chromatography eluting with EtOAc in petroleum ether (1% to 10% gradient) to yield 5-chloro-2-propylpyridine-4-carbonitrile as brow oil (1 g, 10.4%). LC/MS $[M+H]^+$ 181.1.

b) To a solution of 5-chloro-2-propylpyridine-4-carbonitrile (500 mg, 2.77 mmol) in DMSO (8 mL) was slowly added NaOMe solution (30% wt in MeOH, 1.35 g, 9.1 mmol). The resulting mixture was stirred at room temperature for 2 h. Then the reaction mixture was quenched with water (30 mL) and extracted with EtOAc (40 mL×3). The organic phases were combined, washed with brine and dried over $Na_2SO_4$. The solvent was removed under reduced pressure and the residue was purified by flash chromatography eluting with EtOAc in petroleum ether (5% to 50% gradient) to yield 5-methoxy-2-propylpyridine-4-carbonitrile as yellow oil (700 mg, 90%). LC/MS $[M+H]^+$ 177.1.

c) To a solution of 5-methoxy-2-propylpyridine-4-carbonitrile (650 mg, 3.69 mmol) in DCM (10 mL) was slowly added amino 2,4,6-trimethylbenzene-1-sulfonate (3.68 g, 17.08 mmol). The resulting mixture was stirred at room temperature for 2 h. The reaction mixture was concentrated under reduced pressure to yield 1-amino-4-cyano-5-methoxy-2-propylpyridin-1-ium 2,4,6-trimethylbenzene-1-sulfonate as white solid (700 mg, 98%) which was used in next step without further purification. LC/MS $[M]^+$192.1.

d) A mixture of 1-amino-4-cyano-5-methoxy-2-propylpyridin-1-ium 2,4,6-trimethylbenzene-1-sulfonate (2.8 g, 6.16 mmol) and ethyl oxalochloridate (4.0 g, 27.8 mmol) in pyridine (10 mL) was stirred at 100° C. for 2 h. Then the reaction mixture was diluted with water (30 mL) and extracted with EtOAc (40 mL×4). The organic phases were combined, washed with brine and dried over $Na_2SO_4$. The solvent was removed under reduced pressure and the residue was purified by flash chromatography eluting with EtOAc in petroleum ether (10% to 50% gradient) to yield ethyl 5-cyano-3-ethyl-6-methoxypyrazolo[1,5-a]pyridine-2-carboxylate as yellow oil (500 mg). LC/MS $[M+H]^+$ 274.0.

e) 2-[bis(2-fluorophenyl)(hydroxy)methyl]-3-ethyl-6-methoxypyrazolo[1,5-a]pyridine-5-carbonitrile was prepared from ethyl 5-cyano-3-ethyl-6-methoxypyrazolo[1,5-a]pyridine-2-carboxylate using Method E. LC/MS $[M-OH]^+$ 366.0.

f) Method C: A mixture of 2-[bis(2-fluorophenyl)(hydroxy)methyl]-3-ethyl-6-methoxypyrazolo[1,5-a]pyridine-5-carbonitrile (90 mg, 0.21 mmol) and azidotributylstannane (459.0 mg, 1.38 mmol) in toluene (3 mL) was stirred at 80° C. for 18 h. The reaction mixture was concentrated under reduced pressure and the residue was purified by prep-HPLC under the following conditions: column, Kinetex EVO C18 Column, 21.2×150 mm, 5 μm; mobile phase, MeCN in water (with 10 mM $NH_4HCO_3$ and 0.1% $NH_3 \cdot H_2O$), 19% to 31% gradient in 13 min; detector, UV 254/220 nm. [3-Ethyl-6-methoxy-5-(1H-1,2,3,4-tetrazol-5-yl)pyrazolo[1,5-a]pyridin-2-yl]bis(2-fluorophenyl)methanol was obtained as light yellow solid (9.1 mg, 9.2%). LC/MS $[M+H]^+$ 463.1.

Example 7

[3-Ethyl-6-methoxy-5-(1H-1,2,3,4-tetrazol-5-yl) pyrazolo[1,5-a]pyridin-2-yl]diphenylmethanol

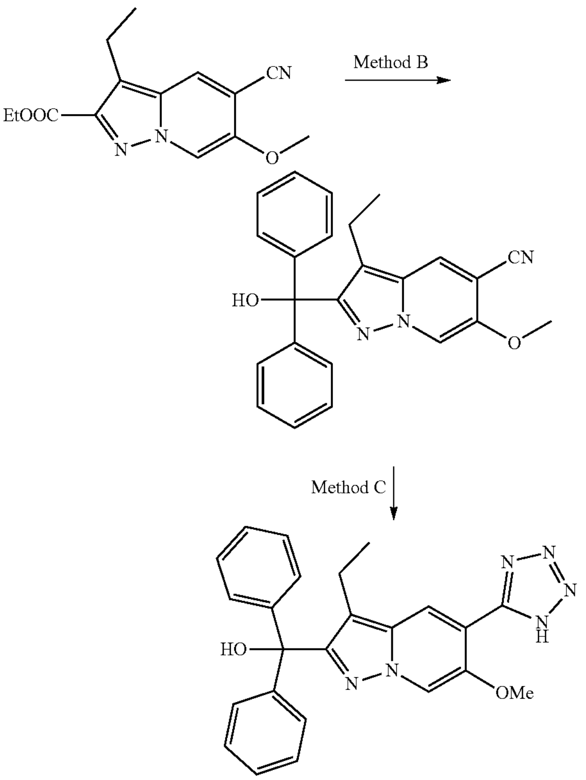

[3-Ethyl-6-methoxy-5-(1H-1,2,3,4-tetrazol-5-yl)pyrazolo[1,5-a]pyridin-2-yl]diphenylmethanol was prepared from ethyl 5-cyano-3-ethyl-6-methoxypyrazolo[1,5-a]pyridine-2-carboxylate, PhMgBr and azidotributylstannane using Method B and Method C. The final product was purified by prep-HPLC under the following conditions: column, XBridge Prep C18 OBD Column, 19×150 mm, 5 μm; mobile phase, MeCN in water (with 10 mM $NH_4HCO_3$ and 0.1% $NH_3 \cdot H_2O$), 30% to 45% gradient in 8 min; detector, UV 254/220 nm. [3-Ethyl-6-methoxy-5-(1H-1,2,3,4-tetrazol-5-yl)pyrazolo[1.5-a]pyridin-2-yl]diphenylmethanol was obtained as light yellow solid (34.9 mg, 16.7% for two steps). LC/MS $[M+H]^+$ 427.1.

Example 8

[3-Ethyl-6-fluoro-5-(1H-tetrazol-5-yl)-pyrazolo[1,5-a]pyridin-2-yl]-diphenyl-methanol

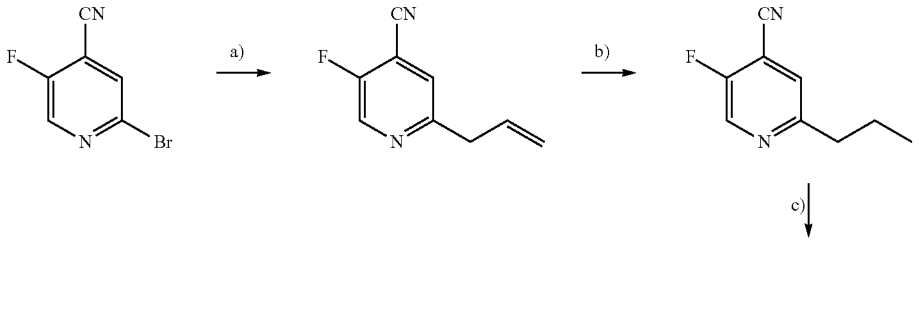

-continued

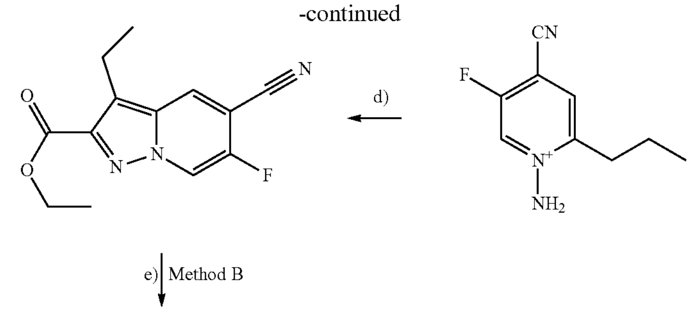

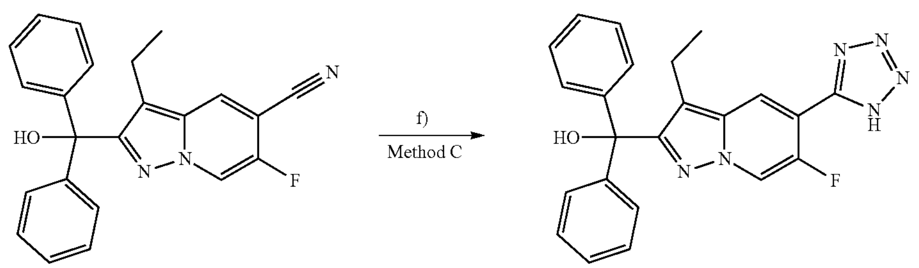

a) Into a flask under inert atmosphere was placed 2-bromo-5-fluoropyridine-4-carbonitrile (1.00 g, 4.73 mmol, 1.00 equiv, 95%), tributyl(prop-2-en-1-yl)stannane (1.80 g, 5.16 mmol, 1.10 equiv, 90%), Pd(amphos)$Cl_2$ (354 mg, 0.47 mmol, 0.10 equiv, 90%) in MeCN (50 mL). The reaction mixture was stirred for 24 h at 100° C. after which it was cooled down to room temperature and concentrated under vacuum. The residue was applied onto a silica gel column with ethyl acetate/petroleum ether (4:96), to yield 500 mg (46%) of 5-fluoro-2-(prop-2-en-1-yl)pyridine-4-carbonitrile as yellow oil (70% purity). LC/MS $[M+H]^+$ 163.0.

b) Into a flask under inert atmosphere was placed 5-fluoro-2-(prop-2-en-1-yl)pyridine-4-carbonitrile (490 mg, 2.12 mmol, 1.00 equiv, 70% purity) and Pd/C (50 mg, 0.42 mmol, 0.15 equiv, 90%) in EtOAC (6 mL). The reaction mixture was set under hydrogen atmosphere (8 mg, 3.77 mmol, 1.31 equiv.) and stirred for 1 h at room temperature. The solids were filtered out and the solution was concentrated under vacuum. The residue was applied onto a silica gel column (ethyl acetate/petroleum ether (1:100) to yield 300 mg (82%) of 5-fluoro-2-propylpyridine-4-carbonitrile as a yellow liquid. LC/MS $[M+H]^+$ 165.1.

c)-f) [3-Ethyl-6-fluoro-5-(1H-tetrazol-5-yl)-pyrazolo[1,5-a]pyridin-2-yl]-diphenyl-methanol was prepared using the same reaction sequence as for Example 6 ([3-Ethyl-6-methoxy-5-(1H-tetrazol-5-yl)-pyrazolo[1,5-a]pyridin-2-yl]-diphenyl-methanol, starting from 5-fluoro-2-propylpyridine-4-carbonitrile. $[M-OH]^+$397.1

General Scheme 3 and Example 9

Synthesis of 1-Ethyl-5-methoxy-6-(1H-tetrazol-5-yl)-1H-imidazo[4.5-b]pyridin-2-yl]-diphenyl-methanol

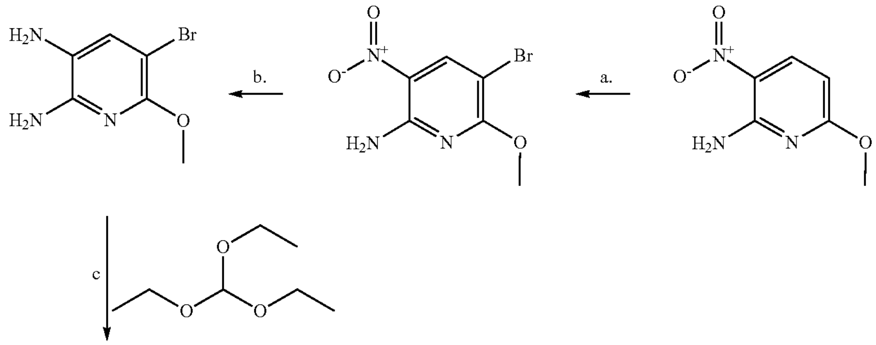

-continued

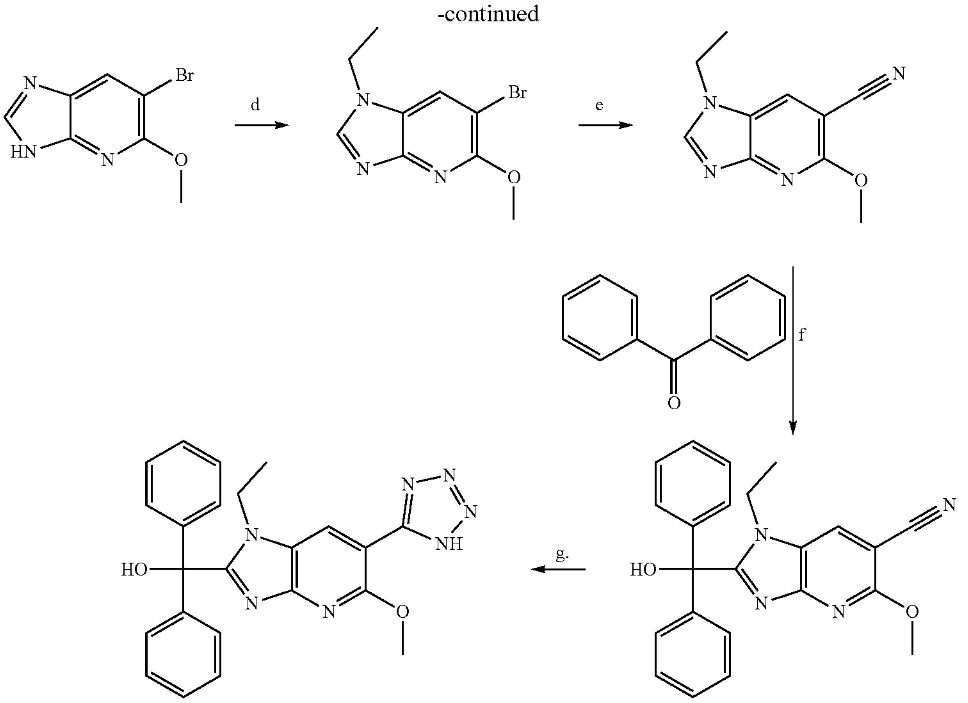

a. Synthesis of 5-bromo-6-methoxy-3-nitro-pyridin-2-ylamine

In a 1 L two-necked flask 6-methoxy-3-nitro-pyridin-2-ylamine (50 g, 286.75 mmol) was dissolved in dry N,N-dimethylformamide (500 ml). N-bromosuccinimide (56.40 g, 313.69 mmol) was added in portions over the time course of 20 min at 14-18° C. The reaction mixture was stirred for 1 hr at room temp. whereas complete conversion to the desired product was observed.

The reaction mixture was poured into 1.5 L of water and stirred for further 30 min at room temp. The solid was filtered off with suction and washed with water. The remaining residue was dried under vacuum at 50° C. overnight to yield pure 5-bromo-6-methoxy-3-nitro-pyridin-2-ylamine (69.76 g. 280.14 mmol). $[M+H]^+$=247.0/249.9 (single bromine isotope distribution).

b. Synthesis of 5-bromo-6-methoxy-pyridine-2,3-diamine and c. 6-Bromo-5-methoxy-3H-imidazo[4.5-b]pyridine 5-Bromo-6-methoxy-3-nitro-pyridin-2-ylamine (10 g, 40.32 mmol) was dissolved in tetrahydrofuran (100 ml). Subsequently, the reaction mixture was treated overnight (16 hours) with sponge nickel catalyst (3 g, pH neutral, THF) and hydrogen under standard pressure at room temp. After filtration and having rinsed the filter cake with additional tetrahydrofuran, a solution of 5-bromo-6-methoxy-pyridine-2,3-diamine (8.79 g, 40.3 mmol) in approx. 300 mL of THF was obtained and used in the next step without further purification. To the solution in a 1 L three-necked flask with condenser, triethyl orthoformate (219.75 ml) and formic acid (strength 98-100%, 3.84 ml, 100.78 mmol) were added. Then, the reaction mixture was heated at 90° C. under an argon atmosphere for 3 hours. For work-up, the reaction mixture was evaporated in vacuo. Subsequently, the residue was dissolved in methanol (approx. 150 ml), diluted with aqueous HCl solution (strength 2.0 M, approx. 500 ml) and demineralized water (approx. 300 ml) followed by extraction with ethyl acetate (twice, 300 ml each). The organic layer was discarded. The aqueous layer was cooled in an ice bath and neutralized with aqueous KOH solution (strength 47%, approx. 50 ml) under stirring during a time course of 30 min to obtain a solution of pH 6. The formed precipitate was filtered off with suction, washed twice with demineralized water (50 ml each), and dried in the vacuum drying cabinet (approx. 60 mbar at 65° C. for 63 hours) to yield 6-bromo-5-methoxy-3H-imidazo[4.5-b] pyridine as a solid (6.39 g, purity 97.9%, 27.44 mmol, yield 68.1%). A second crop of the title product was obtained by extracting the remaining aqueous layer with ethyl acetate (twice, 200 ml each). The combined organic layers were dried over sodium sulfate, filtered with suction, and evaporated in vacuo to yield 6-bromo-5-methoxy-3H-imidazo[4.5-b] pyridine (1.17 g, purity 83.9%, 4.30 mmol, yield 10.7%). $[M+H]^+$=228.0/230.0 (single bromine isotope distribution).

d. Synthesis of 6-bromo-1-ethyl-5-methoxy-1H-imidazo[4.5-b]pyridine

6-Bromo-5-methoxy-3H-imidazo[4.5-b]pyridine (11.50 g, 47.86 mmol) was suspended in a mixture of dry tetrahydrofuran (20.13 ml) and dry 1.4-dioxane (60.38 ml). The flask was rendered inert with argon and the suspension was cooled in an ice bath while being kept at 0-5° C. Subsequently, a sodium hydride suspension (strength 60% in paraffin oil, 2.39 g, 59.82 mmol) was added in portions (twice 1.20 g each, caution: hydrogen formation). After completed additions, the flask was again rendered inert with argon and the suspension was stirred at a temp. of 0-5° C. for 15 min. Then, iodoethane (4.54 ml, 55.04 mmol, stabilised with silver) was added dropwise within 5 minutes and stirring was continued for 30 min. The reaction mixture was allowed to warm up to room temp. while stirring was continued for 63 hours (approx. 50% conversion). A second crop of sodium hydride suspension (strength 60% in paraffin oil, 2.39 g, 59.82 mmol) was added in two portions (1.12 g each) and stirring was continued for 15 min, followed by the addition of iodoethane (4.54 ml, 55.04 mmol). After stirring at room temp. for 19 hours (approx. 32% of starting material remained), the procedure was repeated for a third time with sodium hydride suspension (strength 60% in paraffin oil, 4.31 g, 107.68 mmol) and iodoethane (8.48 ml, 102.89 mmol) whereas the suspension was diluted with additional dry tetrahydrofuran (20.13 ml). After warming up to room temp., stirring was continued for further 17 hours until the reaction was completed. For work-up, the reaction mixture was quenched under stirring using saturated aqueous ammonium chloride solution (approx. 20 ml), followed by dilution with demineralized water (approx. 300 ml), and ethyl acetate (approx. 500 ml). After being stirred for additional 30 min, the mixture was filtered and extracted twice with ethyl acetate (200 ml each). The combined organic layers were dried over sodium sulfate, filtered with suction, and evaporated to dryness. The obtained crude product was purified by flash chromatography on silica gel (330 g, solvent gradient dichloromethane/0-0.6 vol. % ethanol) to yield the title product 6-bromo-1-ethyl-5-methoxy-1H-imidazo[4.5-b]pyridine (7.95 g, purity 96.7%, 29.99 mmol, yield 62.7%, HPTLC Silica Gel 60 F254 with Rf 0.61 using solvent mixture dichloromethane—ethanol 10:1, vol./vol.) and byproduct 6-bromo-3-ethyl-5-methoxy-3Himidazo[4.5-b]pyridine (2.40 g, purity 94.7%, 8.88 mmol, yield 18.6%). $[M+H]^+$=256.0/258.0 (single bromine isotope distribution).

e. Synthesis of 1-Ethyl-5-methoxy-1H-imidazo[4.5-b]pyridine-6-carbonitrile

In a 200 ml glass autoclave (Büchi), 6-bromo-1-ethyl-5-methoxy-1H-imidazo[4.5-b]pyridine (11.83 g, 46.21 mmol), $K_4[Fe(CN)_6]$ (7.82 g, 18.51 mmol) and potassium acetate (570 mg, 5.81 mmol) were dissolved in dioxane (100 ml) and water (100 ml). Subsequently, the flask was degassed by repetitive cycles of vacuum and adding argon. Thereafter, a suspension of catalyst tBuBrettPhos Pd G3 (202 mg, 0.236 mmol) in dioxane (10 ml, oxygen-free; suspension treated in ultrasonic bath) was added to the reaction mixture. Then, the mixture was heated to 114° C. (oil bath) for 22 hours under stirring. For work-up, the yellowish mixture was diluted with demineralized water, ethyl acetate (200 ml each), and methanol (100 ml). The mixture was filtered through kieselguhr and the aqeuous layer was extracted three times with ethyl acetate (300 ml each) until no further product remained in the aqueous layer. The combined organic layers were dried over anhydrous sodium sulfate, filtered with suction and concentrated under reduced pressure to obtain 1-ethyl-5-methoxy-1H-imidazo[4.5-b]pyridine-6-carbonitrile (7.80 g, purity 92.0%, 35.49 mmol, yield 73.9%). $[M+H]^+$=203.

f. Synthesis of 1-ethyl-2-(hydroxy-diphenyl-methyl)-5-methoxy-1H-imidazo[4.5-b]pyridine-6-carbonitrile Under an argon atmosphere, 1-ethyl-5-methoxy-1H-imidazo[4.5-b]pyridine-6-carbonitrile (100 mg, 0.476 mmol) and benzophenone (109.48 mg, 0.595 mmol) were suspended in dry tetrahydrofuran (1.5 ml) and cooled to 0-5° C. in an ice bath. Subsequently, a lithium bis(trimethylsilyl) amide solution (1.0 M in THF, 571 µl, 0.571 mmol) was added dropwise within 2 minutes and the obtained solution was stirred further for 1 h. For work-up, the reaction mixture was diluted with saturated aqueous ammonium chloride solution (5 ml), followed by demineralized water (10 ml) and, subsequently, extracted three times with ethyl acetate (10 ml each). The combined organic layers were dried over sodium sulfate, filtered with suction, and evaporated to dryness. The remaining residue was purified by flash chromatography on silica gel (4g, solvent gradient dichloromethane/0-2 vol. % ethanol) to yield 1-ethyl-2-(hydroxy-diphenyl-methyl)-5-methoxy-1 Himidazo[4.5-b]pyridine-6-carbonitrile (166.4 mg, purity 97.1%, 0.42 mmol, yield 88.3%). $[M+H]^+$=385.1; HPTLC: dichloromethane/ethanol (vol./vol. 20:1/$R_f$ 0.68).

g. Synthesis of 1-ethyl-5-methoxy-6-(1H-tetrazol-5-yl)-1H-imidazo[4.5-b]pyridin-2-yl]-diphenyl-methanol Under an argon atmosphere, 1-ethyl-2-(hydroxy-diphenyl-methyl)-5-methoxy-1H-imidazo[4.5-b]pyridine-6-carbonitrile (66 mg, 0.167 mmol), anhydrous zinc chloride (625.5 mg, 4.59 mmol) and sodium azide (361.4 mg, 5.50 mmol, grade extra pure) were suspended in 1-propanol (9.8 ml). Subsequently, the reaction mixture was stirred at 100° C. for 10 hours. For work-up, the mixture was poured into demineralized water (50 ml) and stirred for 30 min. The obtained precipitate was filtered off with suction and rinsed three times with demineralized water (15 ml each). Subsequently, the precipitate was dissolved in a mixture of HCl (2.0 M, 30 ml) and demineralized water (20 ml) and extracted three times with ethyl acetate (50 ml each). The combined organic layers were dried over sodium sulfate, filtered with suction, and evaporated in vacuo. The crude product was purified by chromatography (pHPLC, solvent gradient: water+0.1 vol. % TFA/20-38 vol. % acetonitrile+0.1 vol. % TFA) to yield colorless [1-ethyl-5-methoxy-6-(1H-tetrazol-5-yl)-1H-imidazo[4.5-b]pyridin-2-yl]-diphenyl-methanol (EXAMPLE 9, 400 mg, purity 99.4%, 0.93 mmol, yield 81.1%). $[M+H]^+$=428.1; HPTLC: dichloromethane/ethanol 10:1 (vol./vol.) $R_f$ 0.49.

Reference Compound

Reference compound 3-Ethyl-2-[hydroxy(diphenyl) methyl]-N-[(2R)-2-hydroxypropyl]benzimidazole-5-carboxamide is available as described in WO 2015/175845 (Compound No. 79).

Table 1

Table 1 which is divided in Tables 1a, 1b, 1c, 1d, 1e, 1f, 1g, 1h, 1i and 1j shows exemplary compounds of the present invention.

Compounds of formula I-c which have been synthesized in accordance to General Synthesis 1 and in accordance with or similar to Examples 1 are shown below in Table 1a.

TABLE 1a

| Compound No. | Structure | Name |
| --- | --- | --- |
| 1 | 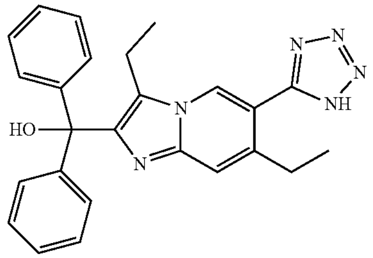 | [3,7-diethyl-6-(1 H-1,2,3,4-tetrazol-5-yl)imidazo[1,2-a]pyridin-2-yl]diphenylmethanol |
| | MW 424.5<br>MS $[M + H]^+$ 425.2 | $^1$H NMR (500 MHz, DMSO-d6) δ = 8.68 (s, 1H), 7.52 (s, 1H), 7.37-7.33 (m, 4H), 7.33-7.28 (m, 4H), 7.28-7.23 (m, 2H), 6.52-6.42 (m, 1H), 2.89 (q, J = 7.4 Hz, 2H), 2.81 (q, J = 7.4 Hz, 2H), 1.09 (t, J = 7.4 Hz, 3H), 0.91 (t, J = 7.4 Hz, 3H) ppm. |
| 2 | 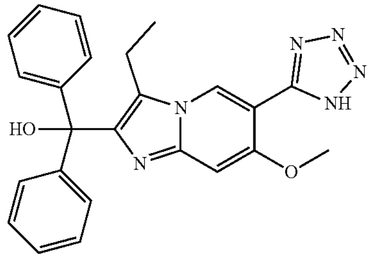 [SMILES: CCc1cc2nc(C(O)(c3ccccc3)c3ccccc3)c(CC)n2cc1-c1nnn[nH]1] | [3-Ethyl-7-methoxy-6-(1H-tetrazol-5-yl)-imidazo[1,2-a]pyridin-2-yl]-diphenyl-methanol |
| | MW 426.5<br>MS $[M + H]^+$ 427.0 | 1H NMR (700 MHz, DMSO-d6) δ 8.71-8.59 (m, 1H), 7.36-7.33 (m, 4H), 7.30-7.26 (m, 4H), 7.24-7.20 (m, 2H), 7.13-7.10 (m, 1H), 6.27-6.20 (m, 1H), 3.90 (s, 3H), 2.90-2.84 (m, 2H), 0.94-0.90 (m, 3H) ppm. |
| 3 | 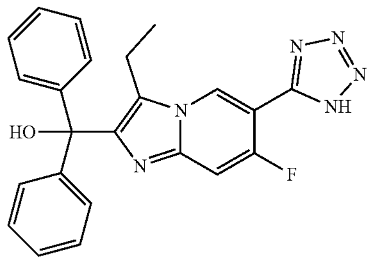 [SMILES: CCc1c(C(O)(c2ccccc2)c2ccccc2)nc2cc(F)c(-c3nnn[nH]3)cn12] | [3-Ethyl-7-fluoro-6-(1H-tetrazol-5-yl)-imidazo[1,2-a]pyridin-2-yl]-diphenyl-methanol |
| | MW 414.4<br>MS $[M + H]^+$415.1 | $^1$H NMR (300 MHz, $CD_3OD$, ppm) δ = 8.83 (d, J = 6.6 Hz, 1 H), 7.45-7.33 (m, 11 H), 2.78 (q, J = 7.5 Hz, 2 H), 1.00 (t, J = 7.5 Hz, 3 H). |

TABLE 1a-continued

| Compound No. | Structure | Name |
|---|---|---|
| 4 | 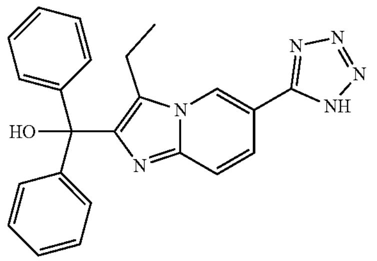 [SMILES: CCc1c(C(O)(c2ccccc2)c2ccccc2)nc2ccc(-c3nnn[nH]3)cn12] | [3-Ethyl-6-(1 H-tetrazol-5-yl)-imidazo[1,2-a]pyridin-2-yl]-diphenyl-methanol |
| | MW 396.5<br>MS $[M + H]^+$ 397.2 | $^1H$ NMR (400 MHz, DMSO-d6, ppm) δ = 8.83 (s, 1 H), 7.79 (dd, J = 9.3, 1.6 Hz, 1 H), 7.65 (dd, J = 9.3, 0.9 Hz, 1 H), 7.35-7.32 (m, 4 H), 7.29-7.22 (m, 6 H), 6.38 (s, 1 H), 2.91 (q, J = 7.4 Hz, 2 H), 0.96 (t, J = 7.4 Hz, 3 H). |

Compounds of formula I-c which have been synthesized in accordance to General Synthesis 1 and in accordance with or similar to Example 2 are shown below in Table 1b.

TABLE 1b

| Compound No. | Structure | Name |
|---|---|---|
| 5 | 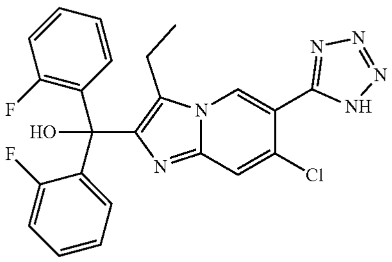 [SMILES: CCc1c(C(O)(c2ccccc2F)c2ccccc2F)nc2cc(Cl)c(-c3nnn[nH]3)cn12] | [7-Chloro-3-ethyl-6-(1H-tetrazol-5-yl)-imidazo[1,2-a]pyridin-2-yl]-bis-(2-fluoro-phenyl)-methanol |
| | MW 466.9<br>MS $[M + H]^+$ 467.1 | $^1H$ NMR (400 MHz, Methanol-d4, ppm) δ = 8.46 (s, 1 H), 7.68 (s, 1 H), 7.43-7.27 (m, 4 H), 7.21-7.05 (m, 4 H), 2.93 (q, J = 7.5 Hz, 2 H), 0.92 (t, J = 7.4 Hz, 3 H). |
| 6 | 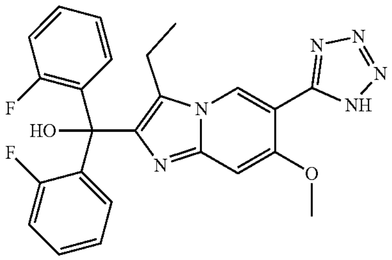 [SMILES: CCc1c(C(O)(c2ccccc2F)c2ccccc2F)nc2cc(OC)c(-c3nnn[nH]3)cn12] | [3-Ethyl-7-methoxy-6-(1H-tetrazol-5-yl)-imidazo[1,2-a]pyridin-2-yl]-bis-(2-fluoro-phenyl)-methanol |
| | MW 462.5<br>MS $[M + H]^+$ 463.0 | 1H NMR (700 MHz, DMSO-d6) δ 8.19-8.17 (m, 1H), 7.34-7.30 (m, 2H), 7.28-7.24 (m, 2H), 7.12 (td, J = 7.6, 1.2 Hz, 2H), 7.08-7.04 (m, 2H), 6.93 (s, 1H), 6.20 (s, 1H), 3.76 (s, 3H), 2.79 (q, J = 7.4 Hz, 2H), 0.86 (t, J = 7.4 Hz, 3H) ppm. |

Compounds of formula I-c which have been synthesized in accordance to General Synthesis 1 and in accordance with or similar to Example 3 are shown below in Table 1c.

TABLE 1c

| Compound No. | Structure | Name |
|---|---|---|
| 7 | 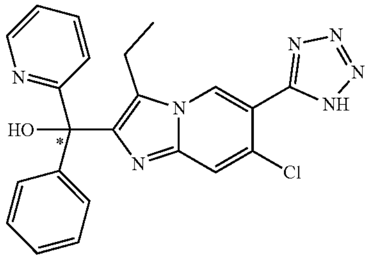 [SMILES: CCc1c(C(O)(c2ccccc2)c2ccccn2)nc2cc(Cl)c(-c3nnn[nH]3)cn12]<br>Isolated enantiomer<br>MW 431.9<br>MS [M + H]+ 432.1 | [7-chloro-3-ethyl-6-(1H-tetrazol-5-yl)imidazo[1,2-a]pyridin-2-yl]-phenyl-(2-pyridyl)methanol<br>$^1$H NMR (400 MHz, $CD_3OD$) δ = 8.65 (s, 1 H), 8.57 (d, J = 4.8 Hz, 1 H), 7.87-7.83 (m, 1 H), 7.79 (s, 1 H), 7.64 (d, J = 8.0 Hz, 1 H), 7.40-7.30 (m, 6 H), 2.85 (q, J = 7.2 Hz, 2 H), 1.01 (t, J = 7.2 Hz, 3 H) ppm.<br>Chiral HPLC: Column, YMC Cellulose-SC, 4.6 mm * 25 cm, 5 μm; mobile phase, n-heptane and EtOH (+1% DEA) 60:40, rt 8.04 min. |
| 8 | 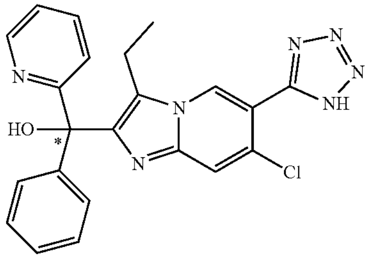 [SMILES: CCc1c(C(O)(c2ccccc2)c2ccccn2)nc2cc(Cl)c(-c3nnn[nH]3)cn12]<br>Isolated enantiomer<br>MW 431.9<br>MS [M + H]+ 432.1 | [7-chloro-3-ethyl-6-(1H-tetrazol-5-yl)imidazo[1,2-a]pyridin-2-yl]-phenyl-(2-pyridyl)methanol<br>$^1$H NMR (400 MHz, $CD_3OD$) δ = 8.67 (s, 1 H), 8.57 (d, J = 4.8 Hz, 1 H), 7.88-7.84 (m, 1 H), 7.80 (s, 1 H), 7.65 (d, J = 8.0 Hz, 1 H), 7.40-7.30 (m, 6 H), 2.85 (q, J = 7.2 Hz, 2 H), 1.01 (t, J = 7.2 Hz, 3 H) ppm.<br>Chiral HPLC: Column, YMC Cellulose-SC, 4.6 mm * 25 cm, 5 μm; mobile phase, n-heptane and EtOH (+1% DEA) 60:40, rt 6.51 min. |
| 9 | 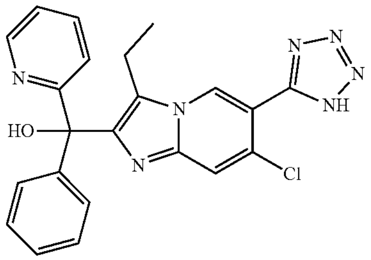 [SMILES: CCc1c(C(O)(c2ccccc2)c2ccccn2)nc2cc(Cl)c(-c3nnn[nH]3)cn12]<br>racemate<br>MW 430.9<br>MS [M + H]+ 431.1 | [7-Chloro-3-ethyl-6-(1H-tetrazol-5-yl)-imidazo[1,2-a]pyridin-2-yl]-diphenyl-methanol<br>1H NMR (400 MHz, Methanol-d4) δ 8.69 (s, 1H), 7.83 (s, 1H), 7.51-7.21 (m, 10H), 2.76 (q, J = 7.4 Hz, 2H), 0.95 (t, J = 7.5 Hz, 3H) ppm. |

Compounds of formula I-c which have been synthesized in accordance to General Synthesis 1 and in accordance with or similar to Example 4 are shown below in Table 1d.

TABLE 1d

| Compound No. | Structure | Name |
|---|---|---|
| 10 | 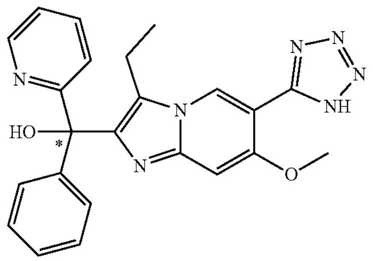 | [3-Ethyl-7-methoxy-6-(1H-tetrazol-5-yl)-imidazo[1,2-a]pyridin-2-yl]-phenyl-pyridin-2-yl-methanol |
| | Isolated enantiomer<br>MW 427.5<br>MS $[M + H]^+$ 428.1 | $^1H$ NMR (400 MHz, $CD_3OD$) δ = 9.28 (s, 1 H), 8.94 (d, J = 4.8 Hz, 1 H), 8.73-8.69 (m, 1 H), 8.25 (d, J = 8.0 Hz, 1 H), 8.19-8.16 (m, 1 H), 7.57-7.53 (m, 5 H), 7.49 (s, 1 H), 4.26 (s, 3 H), 2.73 (q, J = 7.6 Hz, 2 H), 1.13 (t, J = 7.6 Hz, 3 H) ppm.<br>Chiral HPLC: Column, CHIRALPAK IE, 4.6 mm * 25 cm 5 μm; mobile phase, MTBE and MeOH (1% DEA) 70:30, rt 6.29 min. |
| 11 | 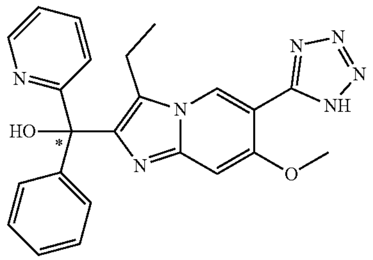 [SMILES: CCc1c(C(O)(c2ccccc2)c2ccccn2)nc2cc(OC)c(-c3nnn[nH]3)cn12] | [3-Ethyl-7-methoxy-6-(1H-tetrazol-5-yl)-imidazo[1,2-a]pyridin-2-yl]-phenyl-pyridin-2-yl-methanol |
| | Isolated enantiomer<br>MW 427.5<br>MS $[M + H]^+$ 428.1 | $^1H$ NMR (400 MHz, $CD_3OD$, ppm) δ = 9.27 (s, 1 H), 8.95 (d, J = 4.8 Hz, 1 H), 8.73-8.69 (m, 1 H), 8.26 (d, J = 8.0 Hz, 1 H), 8.19-8.16 (m, 1 H), 7.57-7.53 (m, 5 H), 7.50 (s, 1 H), 4.26 (s, 3 H), 2.73 (q, J = 7.6 Hz, 2 H), 1.13 (t, J = 7.6 Hz, 3 H).<br>Chiral HPLC: Column, CHIRALPAK IE, 4.6 mm * 25 cm, 5 μm; mobile phase, MTBE and MeOH (+1% DEA) 70:30, rt 7.63 min. |
| 12 | 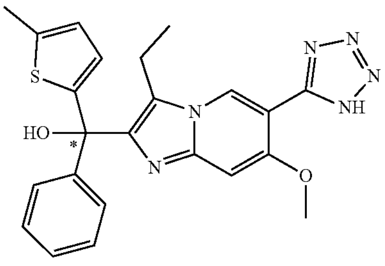 [SMILES: CCc1c(C(O)(c2ccccc2)c2ccc(C)s2)nc2cc(OC)c(-c3nnn[nH]3)cn12] | [3-Ethyl-7-methoxy-6-(1H-tetrazol-5-yl)-imidazo[1,2-a]pyridin-2-yl]-(5-methyl-thiophen-2-yl)-phenyl-methanol |
| | Isolated enantiomer<br>MW 446.5<br>MS $[M + H]^+$ 447.1 | 1H NMR (400 MHz, $CD_3OD$, ppm) δ = 8.77 (s, 1 H), 7.52-7.50 (m, 2 H), 7.42-7.39 (m, 3 H), 7.16 (s, 1 H), 6.70-6.68 (m, 2 H), 4.06 (s, 3 H), 2.70 (q, J = 7.6 Hz, 2 H), 2.48 (s, 3 H), 1.03 (t, J = 7.6 Hz, 3 H).<br>Chiral HPLC: Column, CHIRALPAK IC, 4.6 mm * 25 cm, 5 μm; mobile phase, n-heptane and EtOH (+1% DEA) 50:50, 11.64 min. |

TABLE 1d-continued

| Compound No. | Structure | Name |
| --- | --- | --- |
| 13 | 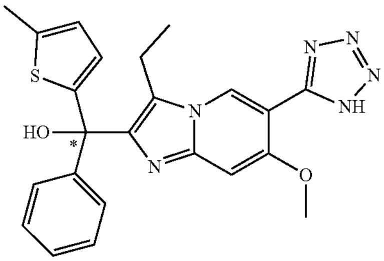 [SMILES: CCc1c(C(O)(c2ccccc2)c2ccc(C)s2)nc2cc(OC)c(-c3nnn[nH]3)cn12] | [3-Ethyl-7-methoxy-6-(1H-tetrazol-5-yl)-imidazo[1,2-a]pyridin-2-yl]-(5-methyl-thiophen-2-yl)-phenyl-methanol |
| | Isolated enantiomer<br>MW 446.5<br>MS $[M + H]^+$ 447.1 | 1H NMR (400 MHz, $CD_3OD$, ppm) δ = 8.73 (s, 1 H), 7.52-7.49 (m, 2 H), 7.42-7.39 (m, 3 H), 7.14 (s, 1 H), 6.70-6.67 (m, 2 H), 4.05 (s, 3 H), 2.70 (q, J = 7.6 Hz, 2 H), 2.48 (s, 3 H), 1.02 (t, J = 7.6 Hz, 3 H).<br>Chiral HPLC: Column, CHIRALPAK IC, 4.6 mm * 25 cm, 5 μm; mobile phase, n-heptane and EtOH (+1% DEA) 50:50, rt 14.63 min. |
| 14 | 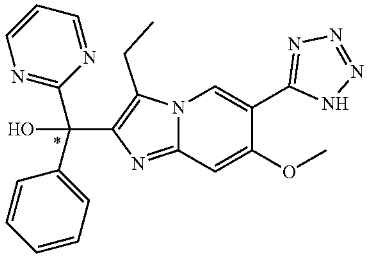 [SMILES: CCc1c(C(O)(c2ccccc2)c2ncccn2)nc2cc(OC)c(-c3nnn[nH]3)cn12] | [3-Ethyl-7-methoxy-6-(1H-tetrazol-5-yl)-imidazo[1,2-a]pyridin-2-yl]-phenyl-pyrimidin-2-yl-methanol |
| | Isolated enantiomer<br>MW 428.5<br>MS $[M + H]^+$ 429.1 | 1H NMR (400 MHz, $CD_3OD$, ppm) δ = 8.92-8.91 (m, 2 H), 8.79 (s, 1 H), 7.53-7.50 (m, 1 H), 7.45-7.37 (m, 5 H), 7.18 (s, 1 H), 4.06 (s, 3 H), 2.75 (q, J = 7.6 Hz, 2 H), 1.03 (t, J = 7.6 Hz, 3 H).<br>Chiral HPLC: column: Chiralpak IC, 2 × 25 cm, 5 μm; mobile phase, EtOH in Hexane and $CH_2Cl_2$ (1:1) with 10 mM $NH_3$ in MeOH, 50% isocratic in 17 min; rt 1.79 min. |
| 15 | 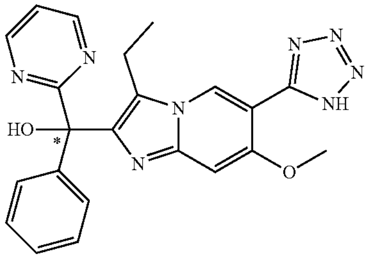 | [3-Ethyl-7-methoxy-6-(1H-tetrazol-5-yl)-imidazo[1,2-a]pyridin-2-yl]-phenyl-pyrimidin-2-yl-methanol |
| | Isolated enantiomer<br>MW 428.5<br>MS $[M + H]^+$ 429.1 | 1H NMR (400 MHz, $CD_3OD$, ppm) δ = 8.92-8.90 (m, 2 H), 8.78 (s, 1 H), 7.53-7.50 (m, 1 H), 7.45-7.37 (m, 5 H), 7.17 (s, 1 H), 4.06 (s, 3 H), 2.75 (q, J = 7.6 Hz, 2 H), 1.03 (t, J = 7.6 Hz, 3 H).<br>Chiral HPLC: column: Chiralpak IC, 2 × 25 cm, 5 μm; mobile phase, EtOH in Hexane and $CH_2Cl_2$ (1:1) with 10 mM $NH_3$ in MeOH, 50% isocratic in 17 min; rt 4.79 min. |

Compounds of formula I-c which have been synthesized in accordance to General Synthesis 1 and in accordance with or similar to Example 5 are shown below in Table 1e.

TABLE 1e

| Compound No. | Structure | Name |
|---|---|---|
| 16 | 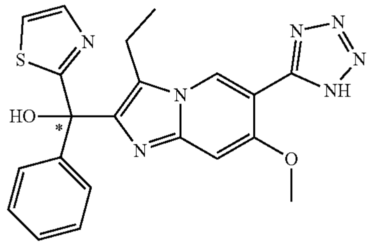 [SMILES: CCc1c(C(O)(c2ccccc2)c2nccs2)nc2cc(OC)c(-c3nnn[nH]3)cn12] | [3-ethyl-7-methoxy-6-(1 H-1 2,3,4-tetrazol-5-yl)imidazo[1,2-a]pyridin-2-yl](phenyl)(1,3-thiazol-2-yl)methanol |
| | racemate<br>MW 433.5<br>MS $[M + H]^+$ 434.1 | 1H NMR (500 MHz, DMSO-d6) δ 16.81-15.89 (m, 1H), 8.93-8.86 (m, 1H), 7.80 (d, J = 3.3 Hz, 1H), 7.73-7.69 (m, 1H), 7.55-7.50 (m, 2H), 7.57-7.24 (m, 1H), 7.37-7.27 (m, 3H), 7.22 (s, 1H), 4.00-3.97 (m, 3H), 2.76 (q, J = 7.7 Hz, 2H), 0.90 (t, J = 7.4 Hz, 3H). |
| 17 | 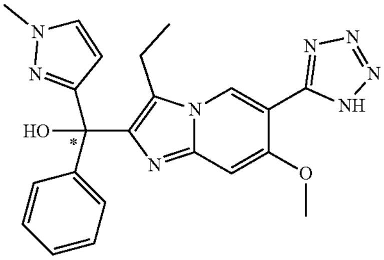 [SMILES: CCc1c(C(O)(c2ccccc2)c2ccn(C)n2)nc2cc(OC)c(-c3nnn[nH]3)cn12] | [3-Ethyl-7-methoxy-6-(1H-tetrazol-5-yl)-imidazo[1,2-a]pyridin-2-yl]-(1-methyl-1H-pyrazol-3-yl)-phenyl-methanol |
| | Isolated enantiomer<br>MW 430.5<br>MS $[M + H]^+$ 431.1 | 1H NMR (400 MHz, $CD_3OD$, ppm) δ = 8.74 (s, 1 H), 7.61 (d, J = 2.0 Hz, 1 H), 7.51-7.49 (m, 2 H), 7.40-7.33 (m, 3 H), 7.19 (s, 1 H), 6.25 (d, J = 2.4 Hz, 1 H), 4.03 (s, 3 H), 3.88 (s, 3 H), 2.69 (q, J = 7.6 Hz, 2 H), 1.00 (t, J = 7.6 Hz, 3 H).<br>Chiral HPLC: column: CHIRALPAK IE, 2 × 25 cm, 5 μm; mobile phase, MeOH in MTBE with 10 mM $NH_3$•MeOH, 25% isocratic in 20 min; rt 3.13 min. |
| 18 | 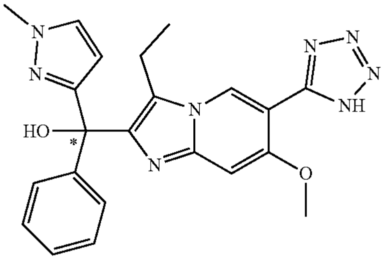 [SMILES: CCc1c(C(O)(c2ccccc2)c2ccn(C)n2)nc2cc(OC)c(-c3nnn[nH]3)cn12] | [3-Ethyl-7-methoxy-6-(1H-tetrazol-5-yl)-imidazo[1,2-a]pyridin-2-yl]-(1-methyl-1H-pyrazol-3-yl)-phenyl-methanol |
| | Isolated enantiomer<br>MW 430.5<br>MS $[M + H]^+$ 431.2 | 1H NMR (400 MHz, $CD_3OD$, ppm) δ = 8.69 (s, 1 H), 7.60 (d, J = 2.0 Hz, 1 H), 7.51-7.49 (m, 2 H), 7.40-7.33 (m, 3 H), 7.16 (s, 1 H), 6.23 (d, J = 2.0 Hz, 1 H), 4.01 (s, 3 H), 3.90 (s, 3 H), 2.69 (q, J = 7.6 Hz, 2 H),1.00 (t, J = 7.6 Hz, 3 H).<br>Chiral HPLC: column: CHIRALPAK IE, 2 × 25 cm, 5 μm; mobile phase, MeOH in MTBE with 10 mM $NH_3$•MeOH, 25% isocratic in 20 min; rt 3.97 min. |

Compounds of formula I-b which have been synthesized in accordance to General Synthesis 2 and in accordance with or similar to Example 6 are shown below in Table 1f.

TABLE 1f

| Compound No. | Structure | Name |
| --- | --- | --- |
| 19 | 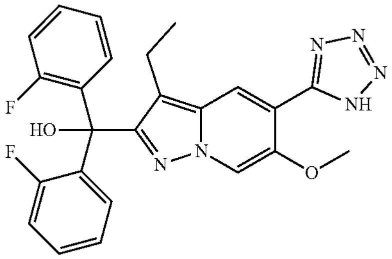 [SMILES: CCc1c(C(O)(c2ccccc2F)c2ccccc2F)nn2cc(OC)c(-c3nnn[nH]3)cc12] | [3-Ethyl-6-methoxy-5-(1H-tetrazol-5-yl)-pyrazolo[1,5-a]pyridin-2-yl]-bis-(2-fluoro-phenyl)-methanol |
| | MW 462.5<br>$[M + H]^+$ 463.1 | 1H NMR (400 MHz) δ 8.25 (d, J = 13.3 Hz, 2H), 7.48-7.27 (m, 4H), 7.19-6.98 (m, 4H), 3.95 (s, 3H), 2.71 (p, J = 7.5 Hz, 2H), 0.96 (t, J = 7.5 Hz, 3H) ppm. |
| 20 | 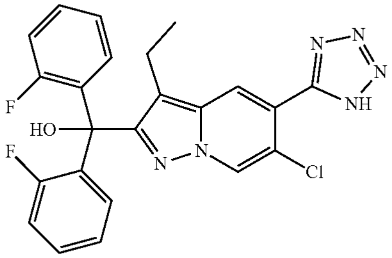 [SMILES: CCc1c(C(O)(c2ccccc2F)c2ccccc2F)nn2cc(Cl)c(-c3nnn[nH]3)cc12] | [6-Chloro-3-ethyl-5-(1H-tetrazol-5-yl)-pyrazolo[1,5-a]pyridin-2-yl]-bis-(2-fluoro-phenyl)-methanol |
| | MW 466.9<br>$[M + H]^+$ 467.0 | 1H NMR (400 MHz, Methanol-d4) δ 8.61 (d, J = 0.8 Hz, 1H), 7.87 (d, J = 0.8 Hz, 1H), 7.43-7.27 (m, 4H), 7.19-7.03 (m, 4H), 2.69 (q, J = 7.5 Hz, 2H), 0.93 (t, J = 7.5 Hz, 3H) ppm. |

Compounds of formula I-b which have been synthesized in accordance to General Synthesis 2 and in accordance with or similar to Example 7 are shown below in Table 1g.

TABLE 1g

| Compond No. | Structure | Name |
| --- | --- | --- |
| 21 | 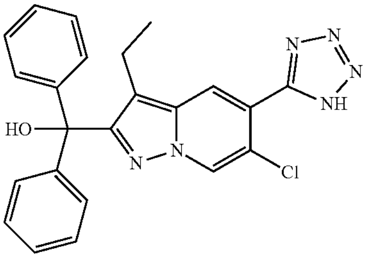 [SMILES: CCc1c(C(O)(c2ccccc2)c2ccccc2)nn2cc(Cl)c(-c3nnn[nH]3)cc12] | [6-Chloro-3-ethyl-5-(1H-tetrazol-5-yl)-pyrazolo[1,5-a]pyridin-2-yl]-diphenyl-methanol |
| | MW 430.9<br>$[M - OH]^+$ 413.1 | 1H NMR (400 MHz, Methanol-d4) δ 8.72 (d, J = 0.7 Hz, 1H), 8.02 (d, J = 0.7 Hz, 1H), 7.40-7.23 (m, 10H), 2.65 (q, J = 7.5 Hz, 2H), 0.91 (t, J = 7.5 Hz, 3H) ppm. |

TABLE 1g-continued

| Compound No. | Structure | Name |
|---|---|---|
| 22 | 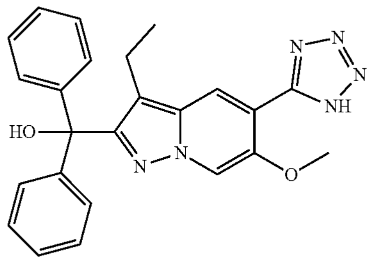 [SMILES: CCc1c(C(O)(c2ccccc2)c2ccccc2)nn2cc(OC)c(-c3nnn[nH]3)cc12]<br>MW 426.5<br>$[M + H]^+$ 427.1 | [3-Ethyl-6-methoxy-5-(1H-tetrazol-5-yl)-pyrazolo[1,5-a]pyridin-2-yl]-diphenyl-methanol<br>$^1H$ NMR (400 MHz, $CD_3OD$, ppm) δ = 8.28 (s, 1 H), 8.20 (s, 1 H), 7.37-7.25 (m, 10 H), 3.95 (s, 3 H), 2.62 (q, J = 7.6 Hz, 2 H), 0.92 (t, J = 7.6 Hz, 3 H) |

Compounds of formula I-b which have been synthesized in accordance to General Synthesis 2 and in accordance with or similar to Example 8 are shown below in Table 1i.

TABLE 1i

| Compound No. | Structure | Name |
|---|---|---|
| 23 | 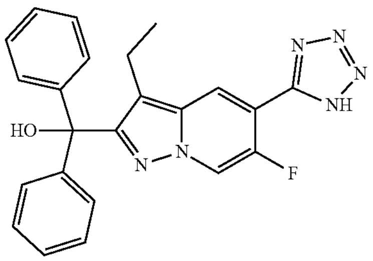 [SMILES: CCc1c(C(O)(c2ccccc2)c2ccccc2)nn2cc(F)c(-c3nnn[nH]3)cc12]<br>MW 414.4<br>$[M - OH]^+$ 397.1 | [3-Ethyl-6-fluoro-5-(1H-tetrazol-5-yl)-pyrazolo[1,5-a]pyridin-2-yl]-diphenyl-methanol<br>$^1H$ NMR (400 MHz, $CD_3OD$) δ = 8.56 (d, J = 5.8 Hz, 1 H), 8.11 (d, J = 7.2 Hz, 1 H), 7.37-7.25 (m, 10 H), 2.63 (q, J = 7.6 Hz, 2 H), 0.92 (t, J = 7.6 Hz, 3 H) ppm. |

Compounds of formula I-a which have been synthesized in accordance to General Synthesis 3 and in accordance with or similar to Example 9 are shown below in Table 1j.

TABLE 1j

| Compound No. | Structure | Name |
|---|---|---|
| 24 | 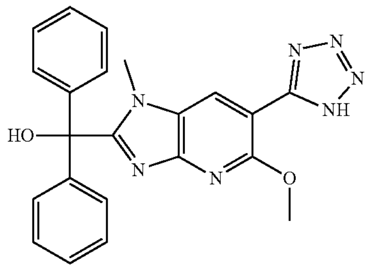 [SMILES: COc1nc2nc(C(O)(c3ccccc3)c3ccccc3)n(C)c2cc1-c1nnn[nH]1]<br>MW 413.4<br>$[M + H]^+$ 414.2 | [5-methoxy-1-methyl-6-(1H-1,2,3,4-tetrazol-5-yl)-1H-imidazo[4,5-b]pyridin-2-yl]diphenylmethanol<br>1H NMR (500 MHz, DMSO-d6) delta 16.14-15.98 (m, 1H), 8.71 (s, 1H), 7.38-7.33 (m, 4H), 7.33-7.28 (m, |

TABLE 1j-continued

| Compound No. | Structure | Name |
|---|---|---|
| | | 6H), 7.27 (s, 1H), 4.05 (s, 3H), 3.68 (s, 3H). |
| 25 | 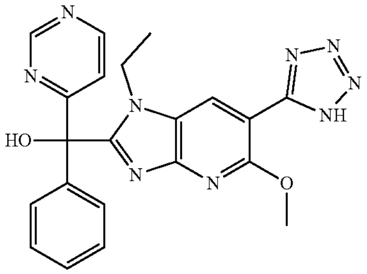 [SMILES: CCn1c(C(O)(c2ccccc2)c2ccncn2)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl](phenyl)(pyrimidin-4-yl)methanol |
| | Racemate MW 429.4 $[M + H]^+$ 430.2 | 1H NMR (700 MHz, DMSO-d6) δ 16.11-16.03 (m, 1H), 9.18-9.17 (m, 1H), 8.88-8.86 (m, 1H), 8.72-8.69 (m, 1H), 7.71-7.69 (m, 2H), 7.47-7.45 (m, 2H), 7.41-7.37 (m, 2H), 7.36-7.33 (m, 1H), 4.29-4.18 (m, 2H), 4.04 (s, 3H), 1.06 (t, J = 7.1 Hz, 3H). |
| 26 | 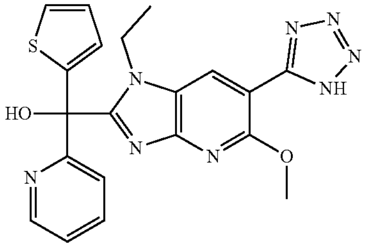 [SMILES: CCn1c(C(O)(c2ccccn2)c2cccs2)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl](pyridin-2-yl)(thiophen-2-yl)methanol |
| | Racemate MW 434.5 $[M + H]^+$ 435.5 | 1H NMR (500 MHz, DMSO-d6) δ 16.13-16.00 (m, 1H), 8.67 (s, 1H), 8.53-8.51 (m, 1H), 7.94-7.90 (m, 1H), 7.79 (s, 1H), 7.73 (dt, J = 8.0, 1.0 Hz, 1H), 7.51 (dd, J = 4.8, 1.6 Hz, 1H), 7.41-7.37 (m, 1H), 7.02-6.98 (m, 2H), 4.37-4.20 (m, 2H), 4.05 (s, 3H), 1.01 (t, J = 7.1 Hz, 3H) ppm. |
| 27 | 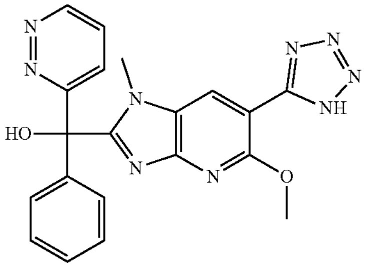 [SMILES: COc1nc2nc(C(O)(c3ccccc3)c3cccnn3)n(C)c2cc1-c1nnn[nH]1] | [1-ethyl-5-methoxy-6-(1H-1,2,3,4-tetrazol-5-yl)-1H-imidazo[4,5-b]pyridin-2-yl](phenyl)(pyridazin-3-yl)methanol |
| | Racemate MW 429.4 $[M + H]^+$ 430.2 | 1H NMR (500 MHz, DMSO-d6) δ 16.12-16.04 (m, 1H), 9.21 (dd, J = 4.9, 1.6 Hz, 1H), 8.71 (s, 1H), 7.85 (dd, J = 8.7, 1.6 Hz, 1H), 7.83 (s, 1H), 7.77 (dd, J = 8.7, 4.9 Hz, 1H), 7.44-7.32 (m, 5H), 4.33-4.19 (m, 2H), 4.03 (s, 3H), 1.07 (t, J = 7.1 Hz, 3H) ppm. |

TABLE 1j-continued

| Compound No. | Structure | Name |
|---|---|---|
| 28 | 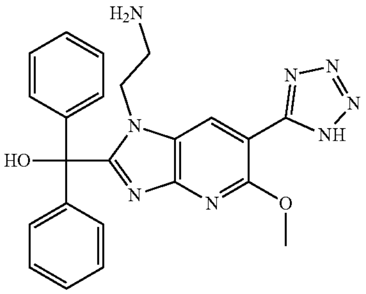 [SMILES: COc1nc2nc(C(O)(c3ccccc3)c3ccccc3)n(CCN)c2cc1-c1nnn[nH]1] | [1-(2-aminoethyl)-5-methoxy-6-(1H-1,2,3,4-tetrazol-5-yl)-1H-imidazo[4,5-b]pyridin-2-yl]diphenylmethanol |
| | Racemate<br>MW 442.5<br>$[M + H]^+$ 443.2 | 1H NMR (500 MHz, DMSO-d6) δ 8.43 (s, 1H), 8.15 (s, 1H), 8.83-7.45 (m, 2H), 7.38-7.28 (m, 10H), 4.32 (t, J = 7.3 Hz, 2H), 3.89 (s, 3H), 2.93 (t, J = 7.2 Hz, 2H). |
| 29 | 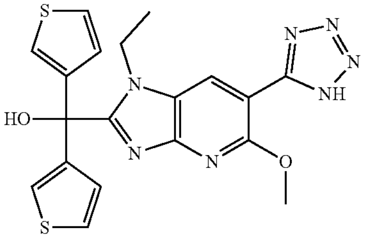 [SMILES: CCn1c(C(O)(c2ccsc2)c2ccsc2)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl]bis(thiophen-3-yl)methanol |
| | Racemate<br>MW 439.5<br>$[M + H]^+$ 440.1 | 1H NMR (500 MHz, DMSO-d6) δ 16.11-16.02 (m, 1H), 8.65 (s, 1H), 7.49 (dd, J = 5.1, 3.0 Hz, 2H), 7.26 (dd, J = 3.0, 1.3 Hz, 2H), 7.24 (s, 1H), 7.08 (dd, J = 5.1, 1.4 Hz, 2H), 4.42 (q, J = 7.1 Hz, 2H), 4.05 (s, 3H), 1.03 (t, J = 7.1 Hz, 3H). |
| 30 | 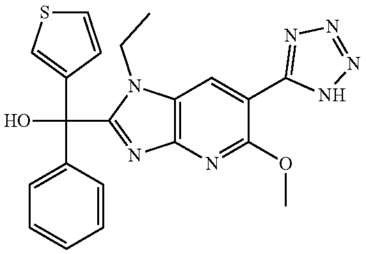 [SMILES: CCn1c(C(O)(c2ccccc2)c2ccsc2)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl](phenyl)(thiophen-3-yl)methanol |
| | Racemate<br>MW 433.5<br>$[M + H]^+$ 434.1 | 1H NMR (500 MHz, DMSO-d6) δ 16.11-16.03 (m, 1H), 8.65 (s, 1H), 7.49 (dd, J = 5.0, 3.0 Hz, 1H), 7.39-7.34 (m, 4H), 7.34-7.29 (m, 1H), 7.28 (s, 1H), 7.15 (dd, J = 3.1, 1.3 Hz, 1H), 7.13 (dd, J = 5.0, 1.3 Hz, 1H), 4.43-4.26 (m, 2H), 4.05 (s, 3H), 1.01 (t, J = 7.1 Hz, 3H). |

TABLE 1j-continued

| Compound No. | Structure | Name |
|---|---|---|
| 31 | 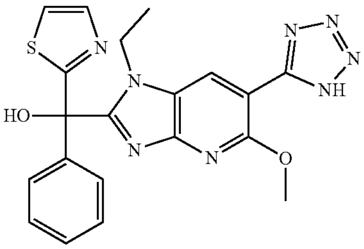 [SMILES: CCn1c(C(O)(c2ccccc2)c2nccs2)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl](phenyl)(1,3-thiazol-2-yl)methanol |
| | Racemate<br>MW 434.5<br>$[M + Na]^+$ 457.0 | 1H NMR (500 MHz, DMSO-d6) δ 16.30-15.81 (m, 1H), 8.69 (s, 1H), 8.14-8.02 (m, 1H), 7.79 (d, J = 3.2 Hz, 1H), 7.78 (d, J = 3.2 Hz, 1H), 7.55-7.51 (m, 2H), 7.41-7.32 (m, 3H), 4.30 (q, J = 7.2 Hz, 2H), 4.05 (s, 3H), 0.98 (t, J = 7.1 Hz, 3H). |
| 32 | 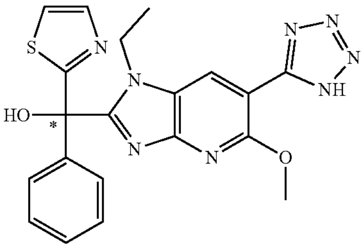 [SMILES: CCn1c(C(O)(c2ccccc2)c2nccs2)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl](phenyl)(1,3-thiazol-2-yl)methanol |
| | Isolated enantiomer<br>MW 434.5<br>$[M + H]^+$ 435.4 | 1H NMR (500 MHz, DMSO-d6) δ 16.33-15.86 (m, 1H), 8.69 (s, 1H), 8.09 (s, 1H), 7.79 (d, J = 3.2 Hz, 1H), 7.78 (d, J = 3.2 Hz, 1H), 7.55-7.52 (m, 2H), 7.41-7.32 (m, 3H), 4.30 (q, J = 7.2 Hz, 2H), 4.05 (s, 3H), 0.98 (t, J = 7.1 Hz, 3H).<br>Chiral SFC: ChiracelOJ-H; solvents: $CO_2$, 30% iPrOH + 0.5% diethylamine + 0.5% HCOOH; rt 2.33 min. |
| 33 | 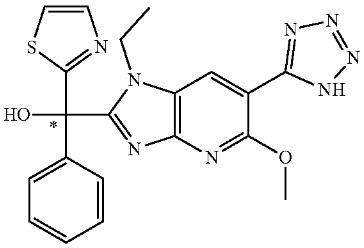 [SMILES: CCn1c(C(O)(c2ccccc2)c2nccs2)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl](phenyl)(1,3-thiazol-2-yl)methanol |
| | Isolated enantiomer<br>MW 434.5<br>$[M + H]^+$ 435.3 | 1H NMR (500 MHz, DMSO-d6) δ 16.33-15.86 (m, 1H), 8.69 (s, 1H), 8.09 (s, 1H), 7.79 (d, J = 3.2 Hz, 1H), 7.78 (d, J = 3.2 Hz, 1H), 7.55-7.52 (m, 2H), 7.41-7.32 (m, 3H), 4.30 (q, J = 7.2 Hz, 2H), 4.05 (s, 3H), 0.98 (t, J = 7.1 Hz, 3H).<br>Chiral SFC: ChiracelOJ-H; solvents: $CO_2$, 30% iPrOH + 0.5% diethylamine + 0.5% HCOOH; rt 4.48 min. |

TABLE 1j-continued

| Compound No. | Structure | Name |
| --- | --- | --- |
| 34 | 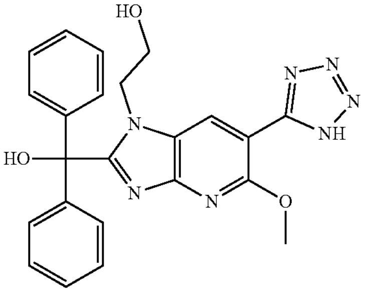 [SMILES: COc1nc2nc(C(O)(c3ccccc3)c3ccccc3)n(CCO)c2cc1-c1nnn[nH]1] | 2-[2-(hydroxy-diphenylmethyl)-5-methoxy-6-(1H-1,2,3,4-tetrazol-5-yl)-1H-imidazo[4,5-b]pyridin-1-yl]ethan-1-ol |
| | MW 443.2<br>$[M + H]^+$ 444.1 | 1H NMR (500 MHz, DMSO-d6) δ 16.63-15.25 (m, 1H), 8.78 (s, 1H), 7.38-7.28 (m, 10H), 4.29 (t, J = 5.6 Hz, 2H), 4.05 (s, 3H), 3.52 (t, J = 5.6 Hz, 2H). |
| 35 | 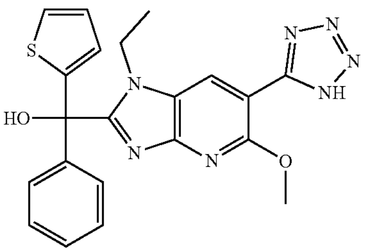 [SMILES: CCn1c(C(O)(c2ccccc2)c2cccs2)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl](phenyl)(thiophen-2-yl)methanol |
| | Racemate<br>MW 433.5<br>$[M+H]^+$ 434.1 | 1H NMR (500 MHz, DMSO-d6) δ 16.51-15.55 (m, 1H), 8.67 (s, 1H), 7.70-7.60 (m, 1H), 7.51 (dd, J = 5.1, 1.3 Hz, 1H), 7.43-7.35 (m, 4H), 7.34-7.30 (m, 1H), 6.99 (dd, J = 5.1, 3.6 Hz, 1H), 6.93 (dd, J = 3.6, 1.3 Hz, 1H), 4.44-4.36 (m, 1H), 4.35-4.26 (m, 1H), 4.07 (s, 3H), 1.01 (t, J = 7.1 Hz, 3H). |
| 36 | 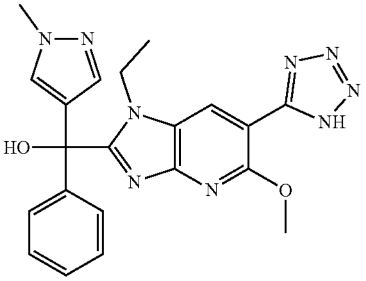 [SMILES: CCn1c(C(O)(c2ccccc2)c2cnn(C)c2)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl](1-methyl-1H-pyrazol-4-yl)phenylmethanol |
| | Racemate<br>MW 431.5<br>$[M + H]^+$ 432.2 | 1H NMR (700 MHz, DMSO-d6) δ 16.46-15.72 (m, 1H), 8.65 (s, 1H), 7.50 (s, 1H), 7.40-7.34 (m, 4H), 7.31-7.27 (m, 2H), 7.16-7.04 (m, 1H), 4.44-4.38 (m, 1H), 4.29-4.22 (m, 1H), 4.07 (s, 3H), 3.81 (s, 3H), 0.96 (t, J = 7.1 Hz, 3H). |

TABLE 1j-continued

| Compound No. | Structure | Name |
|---|---|---|
| 37 | 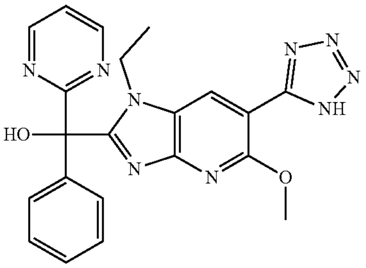 [SMILES: CCn1c(C(O)(c2ccccc2)c2ncccn2)nc2nc(OC)c(-c3nnn[nH]3)cc21]<br>Racemate<br>MW 429.4<br>$[M + H]^+$ 430.2 | [1-ethyl-5-methoxy-6-(1H-1,2,3,4-tetrazol-5-yl)-1H-imidazo[4,5-b]pyridin-2-yl](phenyl)(pyrimidin-2-yl)methanol<br>1H NMR (500 MHz, DMSO-d6) δ 16.08-16.01 (m, 1H), 8.88 (d, J = 4.9 Hz, 2H), 8.68 (s, 1H), 7.52 (t, J = 4.9 Hz, 1H), 7.49-7.45 (m, 2H), 7.38-7.33 (m, 2H), 7.33-7.29 (m, 1H), 7.28-7.24 (m, 1H), 4.27-4.16 (m, 2H), 4.02 (s, 3H), 1.08 (t, J = 7.1 Hz, 3H). |
| 38 | 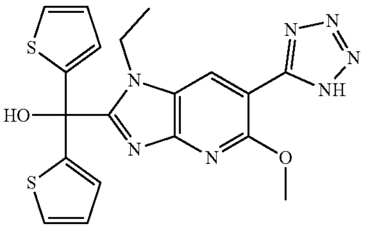 [SMILES: CCn1c(C(O)(c2cccs2)c2cccs2)nc2nc(OC)c(-c3nnn[nH]3)cc21]<br>MW 439.5<br>$[M + H]^+$ 440.1 | [1-ethyl-5-methoxy-6-(1H-1,2,3,4-tetrazol-5-yl)-1H-imidazo[4,5-b]pyridin-2-yl]bis(thiophen-2-yl)methanol<br>1H NMR (700 MHz, DMSO-d6) δ 16.15-16.05 (m, 1H), 8.70 (s, 1H), 7.95 (s, 1H), 7.53 (dd, J = 5.0, 1.3 Hz, 2H), 7.00 (dd, J = 5.0, 3.6 Hz, 2H), 6.97 (dd, J = 3.7, 1.3 Hz, 2H), 4.47 (q, J = 7.1 Hz, 2H), 4.06 (s, 3H), 1.09 (t, J = 7.1 Hz, 3H). |
| 39 | 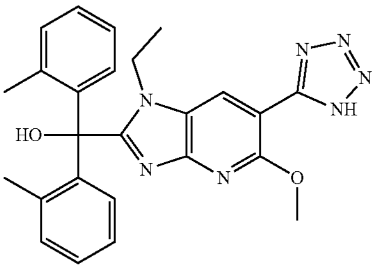 [SMILES: CCn1c(C(O)(c2ccccc2C)c2ccccc2C)nc2nc(OC)c(-c3nnn[nH]3)cc21]<br>MW 455.5<br>$[M + H]^+$ 456.2 | [1-ethyl-5-methoxy-6-(1H-1,2,3,4-tetrazol-5-yl)-1H-imidazo[4,5-b]pyridin-2-yl]bis(2-methylphenyl)methanol<br>1H NMR (500 MHz, DMSO-d6) δ 16.11-16.01 (m, 1H), 8.66 (s, 1H), 7.29-7.25 (m, 2H), 7.23-7.21 (m, 2H), 7.18-7.13 (m, 2H), 7.02-6.98 (m, 2H), 6.88 (s, 1H), 4.29 (q, J = 7.1 Hz, 2H), 4.03 (s, 3H), 2.03 (s, 6H), 1.04 (t, J = 7.1 Hz, 3H). |

TABLE 1j-continued

| Compound No. | Structure | Name |
|---|---|---|
| 40 | 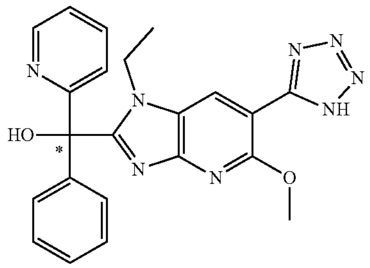 [SMILES: CCn1c(C(O)(c2ccccc2)c2ccccn2)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl](phenyl)(pyridin-2-yl)methanol |
| | Isolated enantiomer<br>MW 428.5<br>$[M + H]^+$ 429.1 | 1H NMR (700 MHz, DMSO-d6) δ 8.55-8.53 (m, 1H), 8.18 (s, 1H), 7.86 (td, J = 7.7, 1.8 Hz, 1H), 7.57-7.55 (m, 1H), 7.44-7.42 (m, 2H), 7.41 (s, 1H), 7.38-7.34 (m, 3H), 7.31-7.28 (m, 1H), 4.15 (q, J = 7.2 Hz, 2H), 3.86 (s, 3H), 1.03 (t, J = 7.2 Hz, 3H).<br>Chiral SFC: Chiralpak AZ-H solvents: $CO_2$, 25% iPrOH + 0.5% diethylamine; rt 10.63 min. |
| 41 | 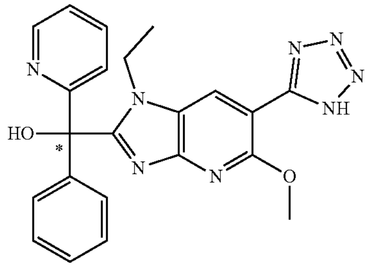 [SMILES: CCn1c(C(O)(c2ccccc2)c2ccccn2)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl](phenyl)(pyridin-2-yl)methanol |
| | Isolated enantiomer<br>MW 428.5<br>$[M + H]^+$ 429.2 | 1H NMR (500 MHz, DMSO-d6) δ 8.55-8.53 (m, 1H), 8.19 (s, 1H), 7.88-7.83 (m, 1H), 7.57-7.55 (m, 1H), 7.45-7.41 (m, 2H), 7.39-7.33 (m, 4H), 7.32-7.27 (m, 1H), 4.15 (q, J = 7.1 Hz, 2H), 3.87 (s, 3H), 1.04 (t, J = 7.1 Hz, 3H).<br>Chiral SFC: Chiralpak AZ-H solvents: $CO_2$, 25% iPrOH + 0.5% diethylamine; rt 18.58 min. |
| 42 | 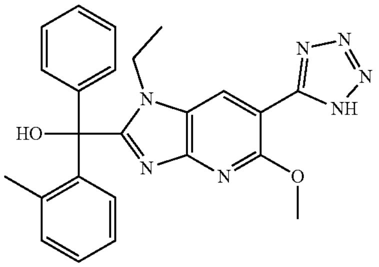 [SMILES: CCn1c(C(O)(c2ccccc2)c2ccccc2C)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl](2-methylphenyl)phenylmethanol |
| | Racemate<br>MW 441.5<br>$[M + H]^+$ 442.1 | 1H NMR (500 MHz, DMSO-d6) δ 16.94-15.08 (m, 1H), 8.67 (s, 1H), 7.41-7.31 (m, 5H), 7.27-7.13 (m, 3H), 7.12-7.08 (m, 1H), 6.75-6.72 (m, 1H), 4.40-4.33 (m, 2H), 4.04 (s, 3H), 2.07 (s, 3H), 1.10 (t, J = 7.1 Hz, 3H). |

TABLE 1j-continued

| Compound No. | Structure | Name |
|---|---|---|
| 43 | 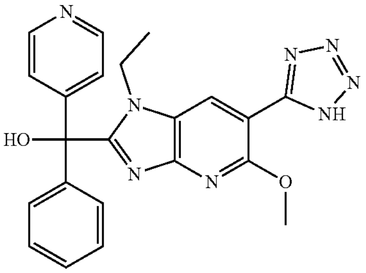 [SMILES: CCn1c(C(O)(c2ccccc2)c2ccncc2)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl](phenyl)(pyridin-4-yl)methanol |
| | Racemate<br>MW 428.5<br>[M + H]$^+$ 429.1 | 1H NMR (500 MHz, DMSO-d6) δ 8.85-8.81 (m, 2H), 8.75 (s, 1H), 8.10-8.03 (m, 1H), 7.98-7.94 (m, 2H), 7.45-7.33 (m, 5H), 4.41-4.17 (m, 2H), 4.04 (s, 3H), 1.11 (t, J = 7.1 Hz, 3H). |
| 44 | 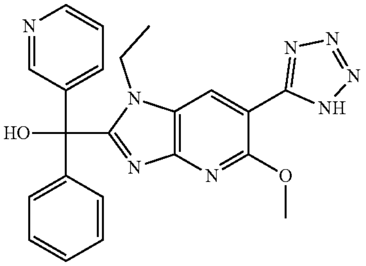 [SMILES: CCn1c(C(O)(c2ccccc2)c2cccnc2)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl](phenyl)(pyridin-3-yl)methanol |
| | Racemate<br>MW 428.5<br>[M + H]$^+$ 429.2 | 1H NMR (400 MHz, DMSO-d6) δ 16.36-15.87 (m, 1H), 8.70 (s, 1H), 8.57-8.55 (m, 1H), 8.50 (dd, J = 4.8, 1.6 Hz, 1H), 7.74-7.70 (m, 1H), 7.54 (s, 1H), 7.43-7.30 (m, 6H), 4.44-4.23 (m, 2H), 4.05 (s, 3H), 1.07 (t, J = 7.1 Hz, 3H). |
| 45 | 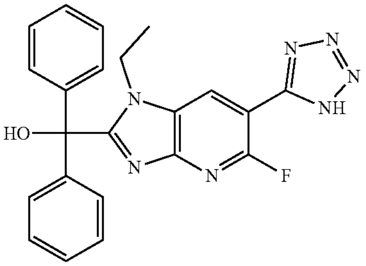 [SMILES: CCn1c(C(O)(c2ccccc2)c2ccccc2)nc2nc(F)c(-c3nnn[nH]3)cc21] | [1-ethyl-5-fluoro-6-(1H-1,2,3,4-tetrazol-5-yl)-1H-imidazo[4,5-b]pyridin-2-yl]diphenylmethanol |
| | MW 415.4<br>[M + H]$^+$ 416.1 | 1H NMR (500 MHz, DMSO-d6) δ 17.18-16.44 (m, 1H), 8.79 (d, J = 8.5 Hz, 1H), 7.41-7.28 (m, 11H), 4.37 (q, J = 7.1 Hz, 2H), 1.08 (t, J = 7.1 Hz, 3H). |
| 46 | 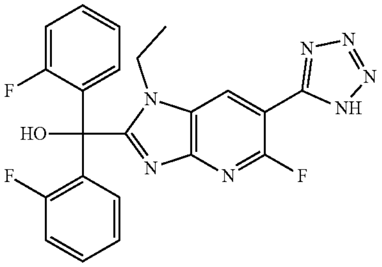 [SMILES: CCn1c(C(O)(c2ccccc2F)c2ccccc2F)nc2nc(F)c(-c3nnn[nH]3)cc21] | [1-ethyl-5-fluoro-6-(1H-1,2,3,4-tetrazol-5-yl)-1H-imidazo[4,5-b]pyridin-2-yl]bis(2-fluorophenyl)methanol |
| | MW 451.4<br>[M + H]$^+$ 452.1 | 1H NMR (700 MHz, DMSO-d6) δ 8.70-8.64 (m, 1H), 7.49-7.47 (m, 1H), |

TABLE 1j-continued

| Compound No. | Structure | Name |
|---|---|---|
| | | 7.42-7.38 (m, 2H), 7.36-7.32 (m, 2H), 7.23-7.19 (m, 2H), 7.15-7.10 (m, 2H), 4.31 (q, J = 7.4 Hz, 2H), 1.09 (t, J = 7.4 Hz, 3H). |
| 47 | 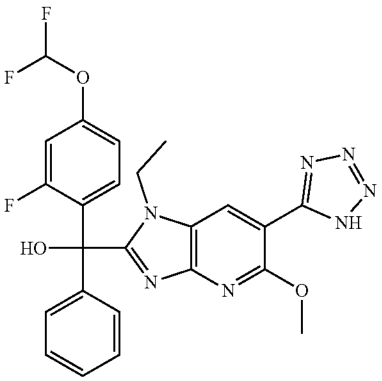 [SMILES: CCn1c(C(O)(c2ccccc2)c2ccc(OC(F)F)cc2F)nc2nc(OC)c(-c3nnn[nH]3)cc21] | [4-(difluoromethoxy)-2-fluorophenyl][1-ethyl-5-methoxy-6-(1H-1,2,3,4-tetrazol-5-yl)-1H-imidazo[4,5-b]pyridin-2-yl]phenylmethanol |
| | Racemate<br>MW511.5<br>$[M + H]^+$ 512.2 | 1H NMR (500 MHz, DMSO-d6) δ 16.40-15.76 (m, 1H), 8.69 (s, 1H), 7.43-7.28 (m, 6H), 7.32 (t, J = 73.6 Hz, 1H), 7.12 (dd, J = 11.8, 2.5 Hz, 1H), 7.06 (t, J = 8.7 Hz, 1H), 7.00 (dd, J = 8.7, 2.5 Hz, 1H), 4.44-4.24 (m, 2H), 4.05 (s, 3H), 1.07 (t, J = 7.1 Hz, 3H). |
| 48 | 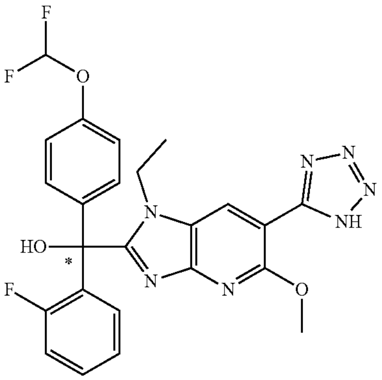 [SMILES: CCn1c(C(O)(c2ccc(OC(F)F)cc2)c2ccccc2F)nc2nc(OC)c(-c3nnn[nH]3)cc21] | [4-(difluoromethoxy)-2-fluorophenyl][1-ethyl-5-methoxy-6-(1H-1,2,3,4-tetrazol-5-yl)-1H-imidazo[4,5-b]pyridin-2-yl]phenylmethanol |
| | Isolated enantiomer<br>MW 511.5<br>$[M+H]^+$ 512.2 | 1H NMR (500 MHz, DMSO-d6) δ 8.14 (s, 1H), 7.45-7.38 (m, 3H), 7.32 (s, 1H), 7.24-7.13 (m, 5H), 7.25 (t, J = 74.1 Hz, 1H), 4.25-4.19 (m, 2H), 3.85 (s, 3H), 1.07 (t, J = 7.1 Hz, 3H). chiral SFC: column: Lux Cellulose-2; eluent: $CO_2$:methanol + 0.5% DEA (75:25); wave length: 220 nm; flow: 5mL/min; rt 9.33 min. |

TABLE 1j-continued

| Compound No. | Structure | Name |
|---|---|---|
| 49 | 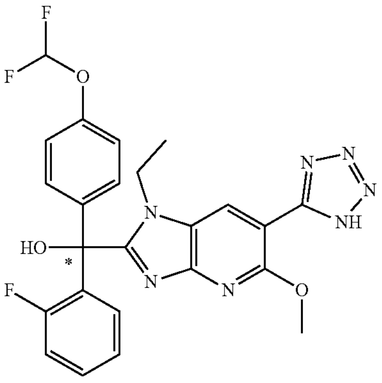 [SMILES: CCn1c(C(O)(c2ccc(OC(F)F)cc2)c2ccccc2F)nc2nc(OC)c(-c3nnn[nH]3)cc21] | [4-(difluoromethoxy)-2-fluorophenyl][1-ethyl-5-methoxy-6-(1H-1,2,3,4-tetrazol-5-yl)-1H-imidazo[4,5-b]pyridin-2-yl]phenylmethanol |
| | Isolated enantiomer<br>MW 511.5<br>$[M + H]^+$ 512.2 | 1H NMR (700 MHz, DMSO-d6) δ 8.14 (s, 1H), 7.44-7.39 (m, 3H), 7.33 (s, 1H), 7.25 (t, J = 74.2 Hz, 1H), 7.24-7.14 (m, 5H), 4.25-4.19 (m, 2H), 3.85 (s, 3H), 1.07 (t, J = 7.1 Hz, 3H). chiral SFC: column: Lux Cellulose-2; eluent: $CO_2$:methanol + 0.5% DEA (75:25); wave length: 220 nm; flow: 5mL/min; rt 6.42 min. |
| 50 | 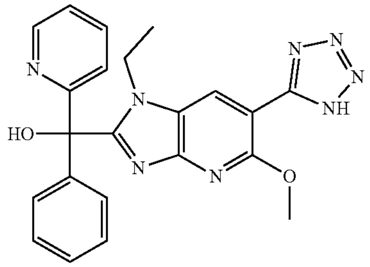 [SMILES: CCn1c(C(O)(c2ccccc2)c2ccccn2)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl](phenyl)(pyridin-2-yl)methanol |
| | Racemate<br>MW 428.5<br>$[M + H]^+$ 429.2 | 1H NMR (500 MHz, DMSO-d6) δ 16.06 (s, 1H), 8.68 (s, 1H), 8.55-8.52 (m, 1H), 7.89-7.85 (m, 1H), 7.59-7.56 (m, 1H), 7.49 (s, 1H), 7.46-7.42 (m, 2H), 7.39-7.28 (m, 4H), 4.29-4.17 (m, 2H), 4.03 (s, 3H), 1.06 (t, J = 7.1 Hz, 3H). |
| 51 | 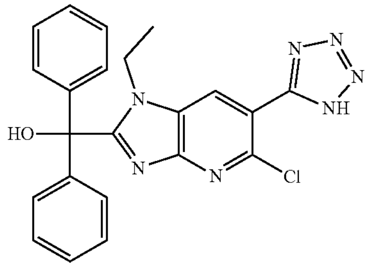 [SMILES: CCn1c(C(O)(c2ccccc2)c2ccccc2)nc2nc(Cl)c(-c3nnn[nH]3)cc21] | [5-chloro-1-ethyl-6-(1H-1,2,3,4-tetrazol-5-yl)-1H-imidazo[4,5-b]pyridin-2-yl]diphenylmethanol |
| | MW 431.9<br>$[M + H]^+$ 432.1 | 1H NMR (700 MHz, DMSO-d6) δ 17.54-16.28 (m, 1H), 8.56 (s, 1H), 7.47-7.41 (m, 1H), 7.39-7.30 (m, 10H), 4.31 (q, J = 7.1 Hz, 2H), 1.05 (t, J = 7.1 Hz, 3H). |

TABLE 1j-continued

| Compound No. | Structure | Name |
|---|---|---|
| 52 | 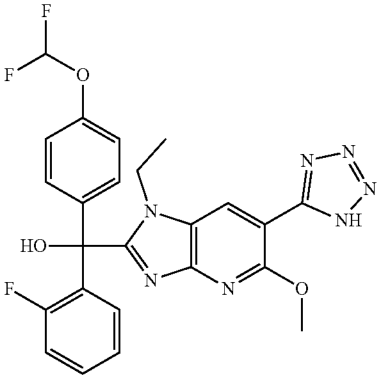 [SMILES: CCn1c(C(O)(c2ccc(OC(F)F)cc2)c2ccccc2F)nc2nc(OC)c(-c3nnn[nH]3)cc21] Racemate MW 511.5 [M + H]+ 512.2 | [4-(difluoromethoxy)phenyl][1-ethyl-5-methoxy-6-(1H-1,2,3,4-tetrazol-5-yl)-1H-imidazo[4,5-b]pyridin-2-yl](2-fluorophenyl)methanol<br>1H NMR (700 MHz, DMSO-d6) δ 16.32-15.81 (m, 1H), 8.69 (s, 1H), 7.47-7.41 (m, 4H), 7.26 (t, J = 74.0 Hz, 1H), 7.22-7.16 (m, 5H), 4.38-4.29 (m, 2H), 4.04 (s, 3H), 1.10 (t, J = 7.1 Hz, 3H). |
| 53 | 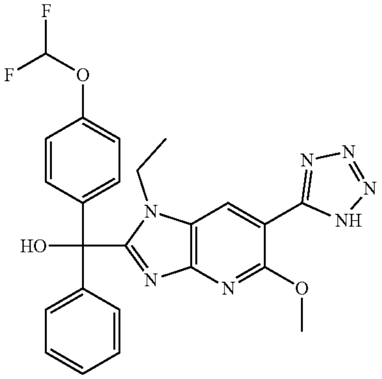 [SMILES: CCn1c(C(O)(c2ccccc2)c2ccc(OC(F)F)cc2)nc2nc(OC)c(-c3nnn[nH]3)cc21] Racemate MW 493.5 [M + H]+ 494.2 | [4-(difluoromethoxy)phenyl][1-ethyl-5-methoxy-6-(1H-1,2,3,4-tetrazol-5-yl)-1H-imidazo[4,5-b]pyridin-2-yl]phenylmethanol<br>1H NMR (700 MHz, DMSO-d6) δ 16.43-15.75 (m, 1H), 8.69 (s, 1H), 7.41-7.35 (m, 5H), 7.33-7.29 (m, 3H), 7.24 (t, J = 74.1 Hz, 1H), 7.17-7.15 (m, 2H), 4.37-4.26 (m, 2H), 4.04 (s, 3H), 1.07 (t, J = 7.1 Hz, 3H). |
| 54 | 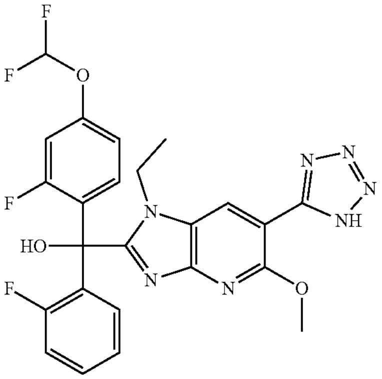 [SMILES: CCn1c(C(O)(c2ccccc2F)c2ccc(OC(F)F)cc2F)nc2nc(OC)c(-c3nnn[nH]3)cc21] Racemate MW 529.5 [M + H]+ 530.1 | [4-(difluoromethoxy)-2-fluorophenyl][1-ethyl-5-methoxy-6-(1H-1,2,3,4-tetrazol-5-yl)-1H-imidazo[4,5-b]pyridin-2-yl](2-fluorophenyl)methanol<br>1H NMR (700 MHz, DMSO-d6) δ 16.17-15.99 (m, 1H), 8.71 (s, 1H), 7.52 (s, 1H), 7.47-7.43 (m, 1H), 7.41-7.35 (m, 2H), 7.34 (t, J = 73.6 Hz, 1H), 7.27-7.25 (m, 1H), 7.18-7.15 (m, 1H), 7.10 (dd, J = 11.8, 2.6 Hz, |

TABLE 1j-continued

| Compound No. | Structure | Name |
|---|---|---|
| | | 1H), 7.06 (dd, J = 8.6, 2.6 Hz, 1H), 4.38-4.28 (m, 2H), 4.04 (s, 3H), 1.14 (t, J = 7.2 Hz, 3H). |
| 55 | 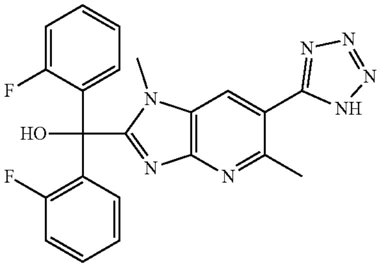 [SMILES: Cc1nc2nc(C(O)(c3ccccc3F)c3ccccc3F)n(C)c2cc1-c1nnn[nH]1] | [1,5-dimethy-6-(1H-1,2,3,4-tetrazol-5-yl)-1H-imidazo[4,5-b]pyridin-2-yl]bis(2-fluorophenyl)methanol |
| | MW 433.4<br>$[M + H]^+$ 434.1 | 1H NMR (400 MHz, DMSO-d6) δ 17.06-16.43 (m, 1H), 8.35 (s, 1H), 7.46-7.35 (m, 5H), 7.26-7.20 (m, 2H), 7.18-7.11 (m, 2H), 3.72 (s, 3H), 2.70 (s, 3H). |
| 56 | 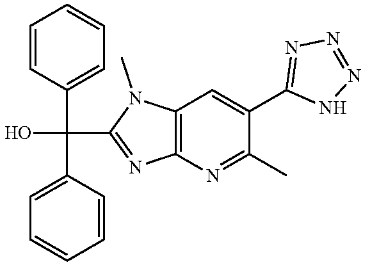 [SMILES: Cc1nc2nc(C(O)(c3ccccc3)c3ccccc3)n(C)c2cc1-c1nnn[nH]1] | [1,5-dimethyl-6-(1H-1,2,3,4-tetrazol-5-yl)-1H-imidazo[4,5-b]pyridin-2-yl]diphenylmethanol |
| | MW 397.4<br>$[M + H]^+$ 398.2 | 1H NMR (700 MHz, DMSO-d6) δ 17.11-16.36 (m, 1H), 8.33 (s, 1H), 7.37-7.28 (m, 11H), 3.63 (s, 3H), 2.71 (s, 3H). |
| 57 | 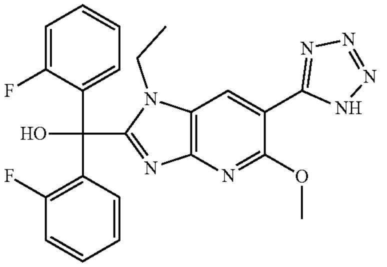 [SMILES: CCn1c(C(O)(c2ccccc2F)c2ccccc2F)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl]bis(2-fluorophenyl)methanol |
| | MW 463.4<br>$[M + H]^+$ 464.1 | 1H NMR (700 MHz, DMSO-d6) δ 16.25-15.89 (m, 1H), 8.65 (s, 1H), 7.46-7.41 (m, 3H), 7.39-7.33 (m, 2H), 7.27-7.21 (m, 2H), 7.19-7.13 (m, 2H), 4.33 (q, J = 7.1 Hz, 2H), 4.02 (s, 3H), 1.11 (t, J = 7.1 Hz, 3H). |

TABLE 1j-continued

| Compound No. | Structure | Name |
|---|---|---|
| 58 | 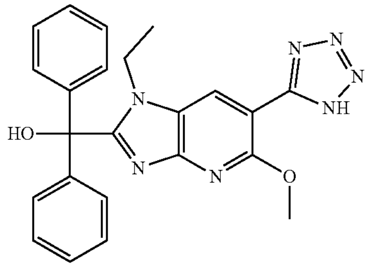 [SMILES: CCn1c(C(O)(c2ccccc2)c2ccccc2)nc2nc(OC)c(-c3nnn[nH]3)cc21] | [1-ethyl-5-methoxy-6-(1H-1,2,3,4-tetrazol-5-yl)-1H-imidazo[4,5-b]pyridin-2-yl]diphenylmethanol |
| | MW 427.5<br>[M +H]$^+$ 428.1 | 1H NMR (500 MHz, DMSO-d6) δ 16.18-15.97 (m, 1H), 8.67 (s, 1H), 7.38-7.28 (m, 11H), 4.33 (q, J = 7.1 Hz, 2H), 4.04 (s, 3H), 1.06 (t, J = 7.1 Hz, 3H). |
| 59 | 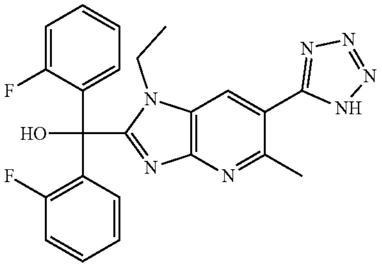 [SMILES: CCn1c(C(O)(c2ccccc2F)c2ccccc2F)nc2nc(C)c(-c3nnn[nH]3)cc21] | [1-ethyl-5-methyl-6-(1H-1,2,3,4-tetrazol-5-yl)-1H-imidazo[4,5-b]pyridin-2-yl]bis(2-fluorophenyl)methanol |
| | MW 447.4<br>[M + H]$^+$ 448.1 | 1H NMR (700 MHz, DMSO-d6) δ 16.92-16.65 (m, 1H), 8.34 (s, 1H), 7.48 (s, 1H), 7.46-7.42 (m, 2H), 7.39-7.35 (m, 2H), 7.26-7.23 (m, 2H), 7.18-7.14 (m, 2H), 4.28 (q, J = 7.1 Hz, 2H), 2.70 (s, 3H), 1.12 (t, J = 7.1 Hz, 3H). |
| 60 | 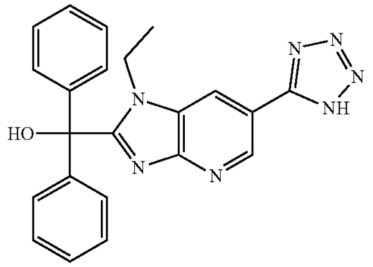 [SMILES: CCn1c(C(O)(c2ccccc2)c2ccccc2)nc2ncc(-c3nnn[nH]3)cc21] | [1-ethyl-6-(1H-1,2,3,4-tetrazol-5-yl)-1H-imidazo[4,5-b]pyridin-2-yl]diphenylmethanol |
| | MW 397.4<br>[M + H]$^+$ 398.1 | 1H NMR (700 MHz, DMSO-d6) δ 17.27-16.76 (m, 1H), 9.04 (d, J = 1.9 Hz, 1H), 8.58 (d, J = 2.0 Hz, 1H), 7.39-7.30 (m, 11H), 4.33 (q, J = 7.2 Hz, 2H), 1.09 (t, J = 7.1 Hz, 3H). |
| 61 | 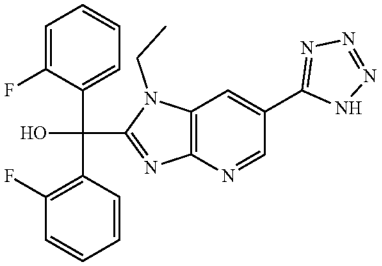 [SMILES: CCn1c(C(O)(c2ccccc2F)c2ccccc2F)nc2ncc(-c3nnn[nH]3)cc21] | [1-ethyl-6-(1H-1,2,3,4-tetrazol-5-yl)-1H-imidazo[4,5-b]pyridin-2-yl]bis(2-fluorophenyl)methanol |
| | MW 433.4<br>[M + H]$^+$ 434.1 | 1H NMR (700 MHz, DMSO-d6) δ 17.16-16.83 (m, 1H), 9.04 (d, J = 2.0 Hz, 1H), 8.61 (d, J = 2.1 Hz, 1H), 7.53 |

TABLE 1j-continued

| Compound No. | Structure | Name |
|---|---|---|
| | | (s, 1H), 7.47-7.43 (m, 2H), 7.41-7.37 (m, 2H), 7.27-7.24 (m, 2H), 7.19-7.14 (m, 2H), 4.35 (q, J = 7.2 Hz, 2H), 1.15 (t, J = 7.2 Hz, 3H). |
| 62 | 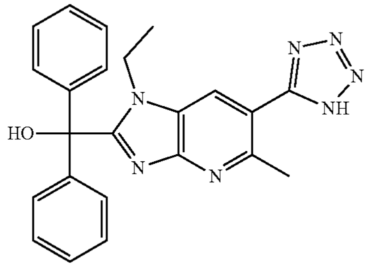 [SMILES: CCn1c(C(O)(c2ccccc2)c2ccccc2)nc2nc(C)c(-c3nnn[nH]3)cc21] | [1-ethyl-5-methyl-6-(1H-1,2,3,4-tetrazol-5-yl)-1H-imidazo[4,5-b]pyridin-2-yl]diphenylmethanol |
| | MW 411.5 [M + H]$^+$ 412.1 | 1H NMR (700 MHz, DMSO-d6) δ 16.96-16.66 (m, 1H), 8.31 (s, 1H), 7.38-7.29 (m, 11H), 4.26 (q, J = 7.1 Hz, 2H), 2.71 (s, 3H), 1.06 (t, J = 7.1 Hz, 3H). |
| 63 | 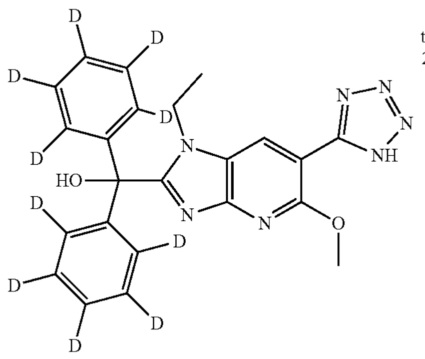 | [1-ethyl-5-methoxy-6-(1H-1,2,3,4-tetrazol-5-yl)-1H-imidazo[4,5-b]pyridin-2-yl]bis[(2,3,4,5,6-$^2$H5)phenyl]methanol |
| | MW 437.5 [M + H]$^+$ 438.3 | 1H NMR (500 MHz, DMSO-d6) δ 16.12-15.98 (m, 1H), 8.67 (s, 1H), 7.28 (s, 1H), 4.33 (q, J = 7.1 Hz, 2H), 4.04 (s, 3H), 1.05 (t, J = 7.1 Hz, 3H). |

Biological Activity

Biochemical Activity ACSS2 Assay (IC50 ACSS2 Biochemical)

The biochemical activity assay for ACSS2 is based on the detection of released AMP by AMP-Glo™ Assay kit (Promega, Madison). The assay is run in three steps: the enzymatic reaction in which human rec ACSS2 activates acetate with ATP and Coenzyme A as cosubstrates to acetyl-CoA thereby releasing AMP and the detection reaction of AMP by AMP Glo assay in which after the destruction of the residual ATP with AMP Glo reagent 1 produced AMP is converted to ATP that is measured in a luciferase assay system (detection reagent). The ACSS2 activity correlates with the detected luminescence signal.

The assay was performed in Perkin Elmer 384 well white Proxiplates in a total volume of 8 µl.

1 nM (fc)C-term myc tagged ACSS2 (human, recombinant, Origene, Rockville, US) and a mixture of 100 µM (fc) ATP, 100 µM (fc) Coenzyme A and 500 µM (fc) sodium acetate were incubated in a total volume of 5 µl (50 mM Hepes, 1 mM Mg-chloride, 150 mM NaCl, 1 mM DTT, 0.01% (w/v) BSA, 0.3% DMSO, pH 7.5) in the absence or presence of the test compound (10 dilution concentrations, start conc 30 µM) for 180 min at 37° C. The reaction was stopped and residual ATP destroyed by the addition of 1 µl AMP Glo reagent solution (Promega, Madison, US). After 1h incubation at room temperature 2 µl of AMP Glo detection reagent was added and the assay was incubated for 0.75 hr at room temperature. The luminescence signal was measured with an Envision multimode reader (Perkin Elmer LAS Germany GmbH) at 700 nm in luminescence mode. The full value used was the inhibitor-free reaction. The pharmacological zero value was generated by addition of ACSS2 inhibitor (Ac-CoA Synthase Inhibitor—CAS 508186-14-9-Calbiochem) in a final concentration of 5 µM. The inhibitory values (IC50) were determined using the program Assay Analyzer® from GeneData.

Experimental data of the compounds shown in Table 1 in the $IC_{50}$ ACSS2 biochemical assay are shown in Table 2 below and classified in the following groups:

| | |
|---|---|
| Group A | $IC_{50}$ is in the range of 0.01 nM to <1 nM |
| Group B | $IC_{50}$ is in the range of 1 nM to <10 nM |
| Group C | $IC_{50}$ is in the range of 10 nM to <100 nM |
| Group D | $IC_{50}$ is in the range of 100 nM to <10000 nM |

Cellular Assay of $^{14}C$ Acetate Incorporation into Fatty Acids ($IC_{50}$ ACSS2 Cellular Lipids)

This protocol describes a cellular assay capable to quantify endogenous fatty acid synthesis activity in the human HCT-15 cancer cell line following the incorporation of extracellularly administered radiolabeled $^{14}C$ acetate with a scintillation proximity based read out on extracted fatty acids.

HCT-15 cells were grown in RPMI 1640 (Gibco) supplemented with 2 mM glutamine, 1 mM sodium pyruvate 10 mM HEPES and 10% FCS (heat-inactivated) passaged every 2-3 days to remain a subconfluent, vital culture. A working cell bank was prepared with each aliquot containing $1\times10^7$ viable cells. After thawing, these cells are dilute immediately 1:20 in pre-warmed (37° C.) culture medium. Cells are collected by centrifugation at 200×g for 5 min, and the supernatant is replaced by 30 mL of fresh culture medium per aliquot to obtain a cell suspension containing 350000 cells/ml. From this cell suspension 100 μL are dispersed into each well of a collagen coated 96 well plate, (black, clear bottom, PS, F-bottom, Greiner) and culture for 24 h (37° C., 5% CO2). After incubation the culture medium is removed and the wells are washed once with 100 μL PBS++(supplemented with $Mg^{2+}/Ca^{2+}$, Gibco) and 50 μL assay medium (RPMI 1640+10 mM HEPES) are added to each well. Compounds serial dilutions are prepared from 10 mM stock solutions in DMSO using a fixed dilution factor (usually 1:3). After preparation of the dilution series in DMSO, the individual dilutions are further diluted in the assay medium. This working dilution is prepared such, that the concentration is 7× of the final concentration in the assay. The maximal DMSO concentration in the final assay is 0.1%.

To each well 10 μL compound working dilution or DMSO blank are added and the cells are cultured for 2 h (37° C., 5% $CO_2$). Then 10 μL AlamarBlue reagent (Invitrogen) containing 14 μCi/mL 14C-acetate (Perkin Elmer) are added to each well (70 μl total volume) and cells are again cultured for 2 h. Cell viability is verified by measuring the AlamarBlue fluorescence (Tecan Safire, ex: 544 nm/em: 590 nm). After incubation the culture medium is removed and the wells are carefully washed once with cold 100 μL PBS++. For cell lysis and fatty acid recovery 50 μl 0.1 M NaOH and 0.1% Triton-X100 are added per well. The plate is sealed with PlateLoc (clear peelable heat seal, Agilent) and incubate at 70° C. for 16-24 h. After cooling to room temperature, the plates are centrifuged for 1 min at 1000 rpm and the plate seals are removed. For acidification 150 μL 0.1 M HCl are added to each well, mixed and 150 μL of the mixture are transferred into a 96 well FlashPlate (Perkin Elmer). The plates are sealed with TopSeal-A (Perkin Elmer). To allow for the fatty acid binding to the well surfaces the plates are incubate for 4 h at 70° C. After cooling to room temperature, the plates are centrifuged for 1 min at 1000 rpm and stored for 0.5-2h at room temperature in the dark. Radioactivity from $^{14}C$ incorporation into fatty acids in the wells is measured as CPM count in a MicroBeta scintillation counter (Perkin Elmer).

Experimental data of the compounds shown in Table 1 in the $IC_{50}$ ACSS2 cellular lipids assay are shown in Table 2 below and classified in the following groups:

| | |
|---|---|
| Group A | $IC_{50}$ is in the range of 0.01 nM to <1 nM |
| Group B | $IC_{50}$ is in the range of 1 nM to <10 nM |

-continued

| | |
|---|---|
| Group C | $IC_{50}$ is in the range of 10 nM to <100 nM |
| Group D | $IC_{50}$ is in the range of 100 nM to <10000 nM |

Cellular Assay of $^{14}C$ Acetate Incorporation into Histones (IC50 ACSS2 Cellular Histone)

This protocol describes a cellular assay capable to quantify endogenous histone acetylation activity in the human HCT-15 cancer cell line following the incorporation of extracellularly administered radiolabeled $^{14}C$ acetate with a scintillation based read out on acid extracted histones.

HCT-15 cells are trypsinized, washed and suspended in DMEM culture medium supplemented with penicillin/streptomycin (100 U/mL), sodium pyruvate (1 mM), and 10% FBS Compounds serial dilutions are prepared in 96-well V-bottom microplate from 10 mM stock solutions in DMSO. From these dilutions 0.5 μl are transferred to a fresh plate including pure DMSO as negative control. The dilutions are prepared such, that the final concentration in the assay is 1/400 of the concentration in the serial dilution. The final DMSO concentration in the assay is 0.25%.

The cell suspension is seeded at densities of $2\times10^5$ cells per 170 μl into individual wells of a 96 well plate each containing 0.5 μl aliquots of compound serial dilutions and are kept for 1 h in a cell incubator. To each well 30 μL of a mixture containing 0.5 mCi/mL of $^{14}C$-acetate with full medium are added. Then, the wells are incubated for 3 hrs in the cell incubator.

Further steps of the procedure should be conducted on ice or instrumentations precooled to 4° C. Cells are sedimented in the 96-well V-bottom microplate by centrifugation (Eppendorf 5804 R) at 1200 rpm for 5 min. The supernatant is removed and the cells are washed twice with 200 μL of PBS-NaB (5 mM sodium butyrate) buffer by iterative resuspension and centrifugation. Finally, the cells are resuspended in 50 μL of TEB (PBS-NaB+0.5% Triton X-100) and left on ice for 10 minutes. After centrifugation at 2300 rpm for 10 minutes at 4° C. the supernatant is removed, the remaining pellet is suspended in 50 μL of 0.2M HCl and incubated over night at 4° C. After incubation the well plate is shaken for 2 minutes in a MTP plate shaker set to 1200 rpm and then centrifuged at 3700 rpm for 10 mins. The lysate is carefully aspirated (~43 μL) and transferred into a white MTP plate (Greiner bio-one 65509). 90 μL of Ultima Gold XR scintillation cocktail are added and the plates are sealed with a transparent cover tape before mixing vigorously using plate shaker set to 1200 rpm. Radioactivity from $^{14}C$ incorporation in the wells is measured as CPM count in a MicroBeta Trilux luminescence counter.

Experimental data of the compounds shown in Table 1 in the $IC_{50}$ ACSS2 cellular histone assay are shown in Table 2 below and classified in the following groups:

| | |
|---|---|
| Group A | $IC_{50}$ is in the range of 0.01 nM to <1 nM |
| Group B | $IC_{50}$ is in the range of 1 nM to <10 nM |
| Group C | $IC_{50}$ is in the range of 10 nM to <100 nM |
| Group D | $IC_{50}$ is in the range of 100 nM to <10000 nM |

Micronucleus Assay (MNT)

The in vitro MNT assay is performed in CHO-K1 cells due to their stable and well-characterized karyotype, high sensitivity and suitability for a high content imaging approach. They have a basal spontaneous micronucleus frequency of 3-4%.

24 hrs after plating CHO-K1 cells are treated with test compounds for 24 hrs (in duplicates; fixed concentration ranges from 0.2 μM to 100 μM in 2-fold dilution steps). After a medium change cells are incubated for 24 hrs with Cytochalasin B to block cytokinesis and are then fixed and nuclei/micronuclei visualized with a DNA stain. Images are acquired with the Molecular Devices high content imagers IXU or IXM and are analyzed with the dedicated MetaXpress software micronucleus module. Criteria for scoring of micronuclei (MN) are the following:

- diameter of the MN should be less than ⅓ of the main nucleus
- MN should be separated from or marginally overlap with main nucleus (=no blebs)
- MN should have similar staining as the main nucleus At least 1000 binucleated cells are evaluated per treatment replicate. Mitomycin C is used as reference stimulator of micronucleus formation. Cytotoxicity is evaluated in parallel and defined by comparing total nuclei count in compound-treated samples to neutral control samples treated with vehicle only (1% DMSO) (100% cytotoxicity means all cells are dead or lost).

A test compound is regarded as POSITIVE if generation of micronuclei and exhibition of less than 60% cytotoxicity at the same concentration can be observed. (A data value is considered as positive if it contains more micronuclei than the mean of the neutral controls plus 3× standard deviation.) A compound is reported as NEGATIVE if no generation of micronuclei at concentrations exhibiting less than 60% cytotoxicity can be observed and at least one tested concentration gives more than 60% cytotoxicity.

A compound is reported as PN (putative negative) if not generating micronuclei and exhibiting less than 60% cytotoxicity at any tested concentration.

A compound is reported as ND (not determinable) at a certain concentration—independent of generating micronuclei or not—if it exhibits more than 60% cytotoxicity at this concentration.

Compounds are scored only in the soluble concentration range.

Experimental data of the compounds shown in Table 1 in the MNT assay are shown in Table 2 below and classified in the following groups:

| | |
|---|---|
| Group A | negative, putative negative (micronuclei detected beyond threshold of 60% cyctotoxicity) |
| Group B | positive |

CYP-Induction Assay in HepaRG Cells with the QuantiGene Plex 2.0 Reagent System (Branched DNA-Assay) from Affymetrix (Thermo Scientific) (CYP3A4 Induction)

The QuantiGene Plex 2.0 assay combines branched DNA (bDNA) signal amplification and multi-analyte profiling beads (xMAP®) technologies to enable the detection and quantitation of multiple RNA targets simultaneously. The xMAP system combines a flow cytometer, fluorescent-dyed microspheres (beads), lasers and digital signal processing to allow multiplexing of up to 100 unique assays within a single sample.

The assay was performed using the Luminex 200 analyzer and a 7-plex QuantiGene Plex 2.0 assay with the following analytes: CYP1A2 (NM_000761), CYP2B6 (NM_000767), CYP2C19 (NM_000769), CYP2C9 (NM_000771), CYP3A4 (NM_017460), HPRT1 (NM_000194) and TFRC (NM003234).

Human HepaRG cells (Thermo Scientific) were thawed and seeded with a density of 0.72E6 cells/ml in a collagen precoated 96-well plate. After an adaption phase of 3 days in first Williams E medium (Gibco+thawing supplement, Thermo Scientific) the medium was changed to second Williams E medium (Gibco+tox supplement, Thermo Scientific). Daily treatment with test substances at 4 concentrations, started between day 3-10 of culturing, was performed with an incubation time of 48 hrs. After 48 hrs the cells were lysed with 100 μl/well (Lysis mixture, Affymetrix diluted 1:2 with Williams E medium, Gibco and addition of 5 μl proteinase K/ml of the mixture, Affymetrix). The QuantiGene Plex 2.0 assay utilizes fluorescent capture beads to trap specific RNA molecules. In order to hybridize and span contiguous sequences of the target RNA, the probe set containing 3 types of synthetic probes (Capture Extenders, Label Extenders, and Blockers) was incubated with samples and beads at 600 rpm at 54° C. for 16-20 h. Signal amplification was mediated by DNA amplification molecules that hybridize to the tails of the label extenders (incubation of the over-night hybridized beads with pre-amplifier and amplifier reagent for 1 h at 50° C. each, washing steps in between). Each amplification unit contains multiple hybridization sites for biotinylated label probes (incubation with label probe reagent for 1 h at 50° C., washing step in between) that bind Streptavidin-conjugated R-Phycoerythrin (SAPE, last incubation step for 30 min at room temp.). After the SAPE incubation, a last washing step with SAPE buffer was performed (120 μl left in wells). The resulting fluorescence signal associated with individual capture beads was detected on a Luminex 200 flow cytometer (parameters: volume 100 μl, timeout 45 sec., DD-gate 5,000-25,000, bead events 50). Signals were reported as median fluorescence intensity (MFI) and were proportional to the number of target RNA molecules present in the sample.

For analysis of results, calculation of mean values of 3 technical replicates as well as the standard deviations (% SD up to 30% acceptable) were carried out. The mean value of the blank was subtracted from the mean value of the sample. As the genes HPRT1 and TFRC are housekeeping genes, they are used to normalize sample mean values [(Sample Mean−Blank)/Housekeeper (Mean−Blank)=normalized value (HPRT1 or TFRC)]. Calculation of the fold-change was performed by dividing normalized sample values by the normalized mean values of the DMSO controls [(Sample Mean−Blank)/Housekeeper (Mean−Blank)=fc; (DMSO Mean−Blank)/Housekeeper (Mean−Blank)].

Experimental data of the compounds shown in Table 1 in the CYP3A4 assay are shown in Table 2 below and given in μM (significant induction above 20% threshold; in parentheses: lowest concentration causing at least 2-fold induction):

TABLE 2

| Compound No. | $IC_{50}$ biochemical | $IC_{50}$ cellular lipids | $IC_{50}$ cellular Histone | MNT | CYP3A4 |
|---|---|---|---|---|---|
| 1 | B | | | | |
| 2 | B | B | B | A | 2.3 (5) |
| 3 | B | C | D | A | |
| 4 | C | C | D | A | 2.2 (50) |
| 5 | B | C | D | A | |
| 6 | B | B | B | A | |
| 7 | C | | | A | |
| 8 | B | | D | A | |
| 9 | B | B | D | A | No induction |

TABLE 2-continued

| Compound No. | $IC_{50}$ biochemical | $IC_{50}$ cellular lipids | $IC_{50}$ cellular Histone | MNT | CYP3A4 |
|---|---|---|---|---|---|
| 10 | C | | D | A | |
| 11 | B | B | C | A | |
| 12 | A | | A | | |
| 13 | C | | C | | |
| 14 | C | | D | | |
| 15 | D | | | | |
| 16 | A | | C | | |
| 17 | D | | | | |
| 18 | C | | | | |
| 19 | B | B | C | A | |
| 20 | B | | C | A | |
| 21 | B | B | C | A | 2.6 (50) |
| 22 | B | B | B | A | |
| 23 | C | | C | A | |
| 24 | A | | | | |
| 25 | B | | B | | |
| 26 | C | | B | A | |
| 27 | B | | B | A | |
| 28 | C | | D | | |
| 29 | B | | C | A | |
| 30 | B | | C | A | |
| 31 | B | A | B | | |
| 32 | A | | | A | No induction |
| 33 | C | | C | A | |
| 34 | B | C | D | A | |
| 35 | B | A | B | A | |
| 36 | C | | D | A | |
| 37 | B | B | B | A | |
| 38 | B | C | D | A | |
| 39 | C | | C | | |
| 40 | B | B | A | A | 6.8 (5) |
| 41 | C | | B | | |
| 42 | B | | B | A | |
| 43 | C | | D | | |
| 44 | C | | D | | |
| 45 | C | B | D | | |
| 46 | C | | C | A | |
| 47 | B | | B | A | |
| 48 | B | | B | | |
| 49 | C | | C | | |
| 50 | B | A | A | A | |
| 51 | B | C | C | A | 3.1 (50) |
| 52 | B | | B | A | |
| 53 | B | | C | | |
| 54 | B | | B | | |
| 55 | A | | C | A | |
| 56 | B | C | D | | |
| 57 | A | A | B | A | |
| 58 | A | A | A | A | 3.8 (50) |
| 59 | B | C | D | A | 13.4 (5) |
| 60 | C | D | D | A | |
| 61 | C | | D | A | |
| 62 | B | D | D | A | |
| 63 | A | | B | | |
| Reference Compound | D | B | A | B | 4.1 (0.15) |

The following examples relate to medicaments:

Example A: Injection Vials

A solution of 100 g of an active ingredient of the formula I-a, I-b or I-c and 5 g of disodium hydrogen phosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B: Suppositories

A mixture of 20 g of an active ingredient of the formula I-a, I-b or I-c with 100 g of soya lecithin and 1400 g of cocoa butter is melted, poured into moulds and allowed to cool. Each suppository contains 20 mg of active ingredient.

Example C: Solution

A solution is prepared from 1 g of an active ingredient of the formula I-a, I-b or I-c, 9.38 g of $NaH_2PO_4 \cdot 2H_2O$, 28.48 g of $Na_2HPO_4 \cdot 12H_2O$ and 0.1 g of benzalkonium chloride in 940 mL of bidistilled water. The pH is adjusted to 6.8, and the solution is made up to 1 l and sterilised by irradiation. This solution can be used in the form of eye drops.

Example D: Ointment 500 mg of an active ingredient of the formula I-a, I-b or I-c are mixed with 99.5 g of Vaseline under aseptic conditions.

Example E: Tablets

A mixture of 1 kg of active ingredient of the formula I-a, I-b or I-c, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F: Dragees

Tablets are pressed analogously to Example E and subsequently coated in a conventional manner with a coating of sucrose, potato starch, talc, tragacanth and dye.

Example G: Capsules 2 kg of active ingredient of the formula I-a, I-b or I-c are introduced into hard gelatine capsules in a conventional manner in such a way that each capsule contains 20 mg of the active ingredient.

Example H: Ampoules

A solution of 1 kg of active ingredient of the formula I-a, I-b or I-c in 60 l of bidistilled water is sterile filtered, transferred into ampoules, lyophilised under sterile conditions and sealed under sterile conditions. Each ampoule contains 10 mg of active ingredient.

The invention claimed is:

1. A compound of formula (I-a), formula (I-b), or formula (I-c):

(I-a)

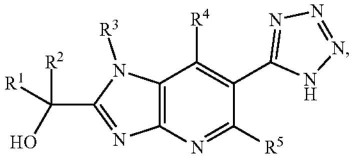

(I-b)

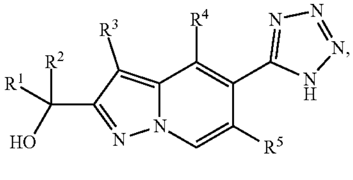

or

-continued

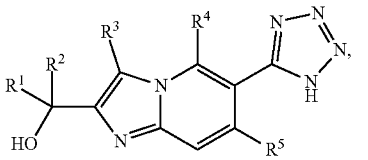

(I-c)

or a pharmaceutically acceptable salt, deuteroisotope, stereoisomer, or tautomer thereof, wherein:

$R^1$ is $Ar^A$ or $Hetar^A$;

$Ar^A$ is a monocyclic or bicyclic aryl;

wherein the monocyclic or bicyclic aryl contains 5, 6, 7, 8, 9, 10, or 11 ring carbon atoms; and wherein the monocyclic or bicyclic aryl is optionally substituted with one or more substituents independently selected from the group consisting of $R^{A1}$, $R^{A2}$, $R^{A3}$, $R^{A4}$, and $R^{A5}$;

$Hetar^A$ is a monocyclic or bicyclic heteroaryl;

wherein the monocyclic or bicyclic heteroaryl contains 5, 6, 7, 8, 9, 10, or 11 ring atoms;

wherein the monocyclic or bicyclic heteroaryl contains ring carbon atoms and 1, 2, 3, 4, or 5 ring heteroatoms independently selected from the group consisting of N, O, and S; and wherein the monocyclic or bicyclic heteroaryl is optionally substituted with one or more substituents independently selected from the group consisting of $R^{A1}$, $R^{A2}$, $R^{A3}$, $R^{A4}$, and $R^{A5}$;

$R^2$ is $Ar^B$ or $Hetar^B$;

$Ar^B$ is a monocyclic or bicyclic aryl;

wherein the monocyclic or bicyclic aryl contains 5, 6, 7, 8, 9, 10, or 11 ring carbon atoms; and wherein the monocyclic or bicyclic aryl is optionally substituted with one or more substituents independently selected from the group consisting of $R^{B1}$, $R^{B2}$, $R^{B3}$, $R^{B4}$, and $R^{B5}$;

$Hetar^B$ is a monocyclic or bicyclic heteroaryl;

wherein the monocyclic or bicyclic heteroaryl contains 5, 6, 7, 8, 9, 10, or 11 ring atoms;

wherein the monocyclic or bicyclic heteroaryl contains ring carbon atoms and 1, 2, 3, 4, or 5 ring heteroatoms independently selected from the group consisting of N, O, and S; and wherein the monocyclic or bicyclic heteroaryl is optionally substituted with one or more substituents independently selected from the group consisting of $R^{B1}$, $R^{B2}$, $R^{B3}$, $R^{B4}$, and $R^{B5}$;

each $R^{A1}$ is independently H, D, F, Cl, Br, I, $C_{1-6}$ aliphatic, or $OC_{1-6}$ aliphatic;

each $R^{A2}$ is independently H, D, F, Cl, Br, I, $C_{1-6}$ aliphatic, or $OC_{1-6}$ aliphatic;

each $R^{A3}$ is independently H, D, F, Cl, Br, I, $C_{1-6}$ aliphatic, or $OC_{1-6}$ aliphatic;

each $R^{A4}$ is independently H, D, F, Cl, Br, I, $C_{1-6}$ aliphatic, or $OC_{1-6}$ aliphatic;

each $R^{A5}$ is independently H, D, F, Cl, Br, I, $C_{1-6}$ aliphatic, or $OC_{1-6}$ aliphatic;

each $R^{B1}$ is independently H, D, F, Cl, Br, I, $C_{1-6}$ aliphatic, or $OC_{1-6}$ aliphatic;

each $R^{B2}$ is independently H, D, F, Cl, Br, I, $C_{1-6}$ aliphatic, or $OC_{1-6}$ aliphatic;

each $R^{B3}$ is independently H, D, F, Cl, Br, I, $C_{1-6}$ aliphatic, or $OC_{1-6}$ aliphatic;

each $R^{B4}$ is independently H, D, F, Cl, Br, I, $C_{1-6}$ aliphatic, or $OC_{1-6}$ aliphatic;

each $R^{B5}$ is independently H, D, F, Cl, Br, I, $C_{1-6}$ aliphatic, or $OC_{1-6}$ aliphatic;

$R^3$ is $C_{1-6}$ aliphatic or $OC_{1-6}$ aliphatic, wherein the $C_{1-6}$ aliphatic or $OC_{1-6}$ aliphatic is optionally substituted with one or more substituents independently selected from the group consisting of $NH_2$ and OH;

$R^4$ is H, D, $C_{1-6}$ aliphatic, or $OC_{1-6}$ aliphatic; and $R^5$ is H, D, F, Cl, Br, I, $C_{1-6}$ aliphatic, or $OC_{1-6}$ aliphatic.

2. The compound according to claim 1, or a pharmaceutically acceptable salt, deuteroisotope, stereoisomer, or tautomer thereof, wherein $R^1$ and $R^2$ are identical.

3. The compound according to claim 1, or a pharmaceutically acceptable salt, deuteroisotope, stereoisomer, or tautomer thereof, wherein $R^1$ and $R^2$ are different.

4. The compound according to claim 1, or a pharmaceutically acceptable salt, deuteroisotope, stereoisomer, or tautomer thereof, wherein:

$Ar^A$ is phenyl, wherein the phenyl is optionally substituted with one or two substituents independently selected from the group consisting of $R^{A1}$ and $R^{A2}$;

$Hetar^A$ is a monocyclic heteroaryl;

wherein the monocyclic heteroaryl contains 5 or 6 ring atoms;

wherein the monocyclic heteroaryl contains ring carbon atoms and 1 or 2 ring heteroatoms independently selected from the group consisting of N, O, and S; and wherein the monocyclic heteroaryl is optionally substituted with one or more substituents independently selected from the group consisting of $R^{A1}$ and $R^{A2}$;

$Ar^B$ is phenyl, wherein the phenyl is optionally substituted with one or two substituents independently selected from the group consisting of $R^{B1}$ and $R^{B2}$; and $Hetar^B$ is a monocyclic heteroaryl;

wherein the monocyclic heteroaryl contains 5 or 6 ring atoms;

wherein the monocyclic heteroaryl contains ring carbon atoms and 1 or 2 ring heteroatoms independently selected from the group consisting of N, O, and S; and wherein the monocyclic heteroaryl is optionally substituted with one or more substituents independently selected from the group consisting of $R^{B1}$ and $R^{B2}$.

5. The compound according to claim 4, or a pharmaceutically acceptable salt, deuteroisotope, stereoisomer, or tautomer thereof, wherein:

each $R^{A1}$ is independently H, F, Cl, $C_{1-4}$ aliphatic, or $OC_{1-4}$ aliphatic;

each $R^{A2}$ is independently H, F, Cl, $C_{1-4}$ aliphatic, or $OC_{1-4}$ aliphatic;

each $R^{B1}$ is independently H, F, Cl, $C_{1-4}$ aliphatic, or $OC_{1-4}$ aliphatic; and each $R^{B2}$ is independently H, F, Cl, $C_{1-4}$ aliphatic, or $OC_{1-4}$ aliphatic.

6. The compound according to claim 1, or a pharmaceutically acceptable salt, deuteroisotope, stereoisomer, or tautomer thereof, wherein:

$R^3$ is $C_{1-4}$ alkyl, wherein the $C_{1-4}$ alkyl is optionally substituted with one or more substituents independently selected from the group consisting of $NH_2$ and OH;

$R^4$ is H; and $R^5$ is H, F, Cl, $C_{1-4}$ alkyl, or $OC_{1-4}$ alkyl.

7. The compound according to claim 1, or a pharmaceutically acceptable salt, deuteroisotope, stereoisomer, or tautomer thereof, wherein:

$Ar^A$ is phenyl, deuterophenyl, fluorophenyl, or methylphenyl;

$Hetar^A$ is thiophen-2-yl, thiophen-3-yl, methylthiophenyl, methylpyrazolyl, thiazolyl, pyridin-2-yl, pyridin-3-yl, pyridin-4-yl, pyridazinyl, or pyrimidinyl;

$Ar^B$ is phenyl, deuterophenyl, fluorophenyl, or methylphenyl;

$Hetar^B$ is thiophen-2-yl, thiophen-3-yl, methylthiophenyl, methylpyrazolyl, thiazolyl, pyridin-2-yl, pyridin-3-yl, pyridin-4-yl, pyridazinyl, or pyrimidinyl;

$R^3$ is $CH_3$, $CH_2CH_3$, $CH_2CH_2NH_2$, or $CH_2CH_2OH$;

$R^4$ is H; and $R^5$ is H, F, Cl, $CH_3$, $CH_2CH_3$, or $OCH_3$.

8. The compound according to claim 7, or a pharmaceutically acceptable salt, deuteroisotope, stereoisomer, or tautomer thereof, wherein:

$Ar^A$ is 2,3,4,5,6-pentadeuterophenyl, 2-fluorophenyl, or 2-methylphenyl;

$Hetar^A$ is thiophen-2-yl, 1-methylpyrazol-3-yl, 1-methylpyrazol-4-yl, 1,3-thiazol-2-yl, pyridazin-3-yl, pyrimidin-2-yl, or pyrimidin-4-yl;

$Ar^B$ is 2,3,4,5,6-pentadeuterophenyl, 2-fluorophenyl, or 2-methylphenyl; and $Hetar^B$ is is thiophen-2-yl, 1-methylpyrazol-3-yl, 1-methylpyrazol-4-yl, 1,3-thiazol-2-yl, pyridazin-3-yl, pyrimidin-2-yl, or pyrimidin-4-yl.

9. A medicament comprising a compound according to claim 1, or a pharmaceutically acceptable salt, deuteroisotope, stereoisomer, or tautomer thereof.

10. A pharmaceutical composition comprising a pharmaceutically acceptable carrier and an effective amount of a compound according to claim 1, or a pharmaceutically acceptable salt, deuteroisotope, stereoisomer, or tautomer thereof.

11. The pharmaceutical composition according to claim 10, wherein the pharmaceutical composition further comprises a second active ingredient.

12. A kit comprising separate packs of (a) an effective amount of a compound according to claim 1, or a pharmaceutically acceptable salt, deuteroisotope, stereoisomer, or tautomer thereof; and (b) a second active ingredient.

13. A method for inhibiting acetyl Co-A synthetase 2 (ACSS2) activity in a subject, wherein the method comprises administering to the subject in need thereof an effective amount of a compound according to claim 1, or a pharmaceutically acceptable salt, deuteroisotope, stereoisomer, or tautomer thereof.

14. The method according to claim 13, wherein the subject has a medical disease or disorder selected from the group consisting of an addiction, an anxiety disorder, bipolar disorder, cancer, depression, an inflammatory disease, an impulse control disorder, a lipid metabolism disorder, a neurogenerative disease, a phobia, post-traumatic stress disorder (PTSD), schizophrenia, and a viral infection.

15. The method according to claim 14, wherein the addiction is a behavioral addiction.

16. The method according to claim 14, wherein the anxiety disorder is panic disorder.

17. The method according to claim 14, wherein the impulse control disorder is obsessive-compulsive disorder or Tourette's syndrome.

18. The method according to claim 14, wherein the inflammatory disease is selected from the group consisting of idiopathic pulmonary fibrosis, muscular dystrophy, rheumatoid arthritis, systemic sclerosis, and ulcerative colitis.

19. The method according to claim 14, wherein the lipid metabolism disorder is fatty liver disease.

20. The method according to claim 19, wherein the fatty liver disease is non-alcoholic fatty liver disease (NAFLD).

21. The method according to claim 13, wherein the subject has a medical disease or disorder selected from the group consisting of an addiction, Crohn's disease, Huntington's disease, non-alcoholic steatohepatitis, a tumor, and a viral infection caused by cytomegalovirus (CMV).

22. The method according to claim 21, wherein the addiction is selected from the group consisting of an addiction to alcohol, an addiction to an amphetamine, an addiction to an anxiolytic, an addiction to cannabis, an addiction to cocaine, an addiction to a hallucinogen, an addiction to a hypnotic, an addiction to an inhalant, an addiction to an opioid, an addiction to a sedative, and an addiction to tobacco.

23. The method according to claim 22, wherein the addiction to a hallucinogen is an addiction to phencyclidine (PCP).

24. A process for manufacturing a compound of formula (I-a), formula (I-b), or formula (I-c) according to claim 1:

(I-a)

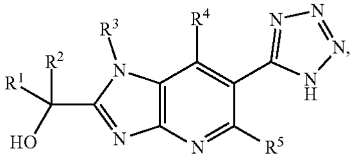

, (I-b)

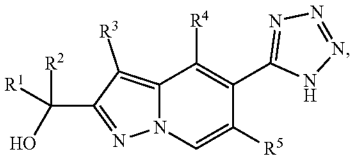

, or (I-c)

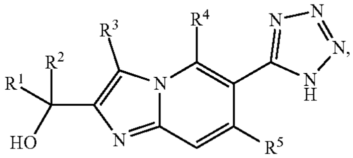

, or a deuteroisotope or tautomer thereof, wherein:

$R^1$ is $Ar^A$ or $Hetar^A$;

$Ar^A$ is a monocyclic or bicyclic aryl;

wherein the monocyclic or bicyclic aryl contains 5, 6, 7, 8, 9, 10, or 11 ring carbon atoms; and wherein the monocyclic or bicyclic aryl is optionally substituted with one or more substituents independently selected from the group consisting of $R^{A1}$, $R^{A2}$, $R^{A3}$, $R^{A4}$, and $R^{A5}$;

$Hetar^A$ is a monocyclic or bicyclic heteroaryl;

wherein the monocyclic or bicyclic heteroaryl contains 5, 6, 7, 8, 9, 10, or 11 ring atoms;

wherein the monocyclic or bicyclic heteroaryl contains ring carbon atoms and 1, 2, 3, 4, or 5 ring heteroatoms independently selected from the group consisting of N, O, and S; and wherein the monocyclic or bicyclic heteroaryl is optionally substituted with one or more substituents independently selected from the group consisting of $R^{A1}$, $R^{A2}$, $R^{A3}$, $R^{A4}$, and $R^{A5}$;

$R^2$ is $Ar^B$ or $Hetar^B$;

$Ar^B$ is a monocyclic or bicyclic aryl;

wherein the monocyclic or bicyclic aryl contains 5, 6, 7, 8, 9, 10, or 11 ring carbon atoms; and wherein the monocyclic or bicyclic aryl is optionally substituted with one or more substituents independently selected from the group consisting of $R^{B1}$, $R^{B2}$, $R^{B3}$, $R^{B4}$, and $R^{B5}$;

$Hetar^B$ is a monocyclic or bicyclic heteroaryl;

wherein the monocyclic or bicyclic heteroaryl contains 5, 6, 7, 8, 9, 10, or 11 ring atoms;

wherein the monocyclic or bicyclic heteroaryl contains ring carbon atoms and 1, 2, 3, 4, or 5 ring heteroatoms independently selected from the group consisting of N, O, and S; and wherein the monocyclic or bicyclic heteroaryl is optionally substituted with one or more substituents independently selected from the group consisting of $R^{B1}$, $R^{B2}$, $R^{B3}$, $R^{B4}$, and $R^{B5}$;

each $R^{A1}$ is independently H, D, F, Cl, Br, I, $C_{1-6}$ aliphatic, or $OC_{1-6}$ aliphatic;

each $R^{A2}$ is independently H, D, F, Cl, Br, I, $C_{1-6}$ aliphatic, or $OC_{1-6}$ aliphatic;

each $R^{A3}$ is independently H, D, F, Cl, Br, I, $C_{1-6}$ aliphatic, or $OC_{1-6}$ aliphatic;

each $R^{A4}$ is independently H, D, F, Cl, Br, I, $C_{1-6}$ aliphatic, or $OC_{1-6}$ aliphatic;

each $R^{A5}$ is independently H, D, F, Cl, Br, I, $C_{1-6}$ aliphatic, or $OC_{1-6}$ aliphatic;

each $R^{B1}$ is independently H, D, F, Cl, Br, I, $C_{1-6}$ aliphatic, or $OC_{1-6}$ aliphatic;

each $R^{B2}$ is independently H, D, F, Cl, Br, I, $C_{1-6}$ aliphatic, or $OC_{1-6}$ aliphatic;

each $R^{B3}$ is independently H, D, F, Cl, Br, I, $C_{1-6}$ aliphatic, or $OC_{1-6}$ aliphatic;

each $R^{B4}$ is independently H, D, F, Cl, Br, I, $C_{1-6}$ aliphatic, or $OC_{1-6}$ aliphatic;

each $R^{B5}$ is independently H, D, F, Cl, Br, I, $C_{1-6}$ aliphatic, or $OC_{1-6}$ aliphatic;

$R^3$ is $C_{1-6}$ aliphatic or $OC_{1-6}$ aliphatic, wherein the $C_{1-6}$ aliphatic or $OC_{1-6}$ aliphatic is optionally substituted with one or more substituents independently selected from the group consisting of $NH_2$ and OH;

$R^4$ is H, D, $C_{1-6}$ aliphatic, or $OC_{1-6}$ aliphatic; and $R^5$ is H, D, F, Cl, Br, I, $C_{1-6}$ aliphatic, or $OC_{1-6}$ aliphatic;

wherein the process comprises the following step:

(a) cyclizing a carbonitrile of formula (II-a):

(II-a)

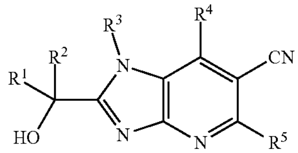

wherein:

$R^1$ is $Ar^A$ or $Hetar^A$;

$Ar^A$ is a monocyclic or bicyclic aryl;

wherein the monocyclic or bicyclic aryl contains 5, 6, 7, 8, 9, 10, or 11 ring carbon atoms; and wherein the monocyclic or bicyclic aryl is optionally substituted with one or more substituents independently selected from the group consisting of $R^{A1}$, $R^{A2}$, $R^{A3}$, $R^{A4}$, and $R^{A5}$;

$Hetar^A$ is a monocyclic or bicyclic heteroaryl;

wherein the monocyclic or bicyclic heteroaryl contains 5, 6, 7, 8, 9, 10, or 11 ring atoms;

wherein the monocyclic or bicyclic heteroaryl contains ring carbon atoms and 1, 2, 3, 4, or 5 ring heteroatoms independently selected from the group consisting of N, O, and S; and wherein the monocyclic or bicyclic heteroaryl is optionally substituted with one or more substituents independently selected from the group consisting of $R^{A1}$, $R^{A2}$, $R^{A3}$, $R^{A4}$, and $R^{A5}$;

$R^2$ is $Ar^B$ or $Hetar^B$;

$Ar^B$ is a monocyclic or bicyclic aryl;

wherein the monocyclic or bicyclic aryl contains 5, 6, 7, 8, 9, 10, or 11 ring carbon atoms; and wherein the monocyclic or bicyclic aryl is optionally substituted with one or more substituents independently selected from the group consisting of $R^{B1}$, $R^{B2}$, $R^{B3}$, $R^{B4}$, and $R^{B5}$;

$Hetar^B$ is a monocyclic or bicyclic heteroaryl;

wherein the monocyclic or bicyclic heteroaryl contains 5, 6, 7, 8, 9, 10, or 11 ring atoms;

wherein the monocyclic or bicyclic heteroaryl contains ring carbon atoms and 1, 2, 3, 4, or 5 ring heteroatoms independently selected from the group consisting of N, O, and S; and wherein the monocyclic or bicyclic heteroaryl is optionally substituted with one or more substituents independently selected from the group consisting of $R^{B1}$, $R^{B2}$, $R^{B3}$, $R^{B4}$, and $R^{B5}$;

each $R^{A1}$ is independently H, D, F, Cl, Br, I, $C_{1-6}$ aliphatic, or $OC_{1-6}$ aliphatic;

each $R^{A2}$ is independently H, D, F, Cl, Br, I, $C_{1-6}$ aliphatic, or $OC_{1-6}$ aliphatic;

each $R^{A3}$ is independently H, D, F, Cl, Br, I, $C_{1-6}$ aliphatic, or $OC_{1-6}$ aliphatic;

each $R^{A4}$ is independently H, D, F, Cl, Br, I, $C_{1-6}$ aliphatic, or $OC_{1-6}$ aliphatic;

each $R^{A5}$ is independently H, D, F, Cl, Br, I, $C_{1-6}$ aliphatic, or $OC_{1-6}$ aliphatic;

each $R^{B1}$ is independently H, D, F, Cl, Br, I, $C_{1-6}$ aliphatic, or $OC_{1-6}$ aliphatic;

each $R^{B2}$ is independently H, D, F, Cl, Br, I, $C_{1-6}$ aliphatic, or $OC_{1-6}$ aliphatic;

each $R^{B3}$ is independently H, D, F, Cl, Br, I, $C_{1-6}$ aliphatic, or $OC_{1-6}$ aliphatic;

each $R^{B4}$ is independently H, D, F, Cl, Br, I, $C_{1-6}$ aliphatic, or $OC_{1-6}$ aliphatic;

each $R^{B5}$ is independently H, D, F, Cl, Br, I, $C_{1-6}$ aliphatic, or $OC_{1-6}$ aliphatic;

$R^3$ is $C_{1-6}$ aliphatic or $OC_{1-6}$ aliphatic;

$R^4$ is H, D, $C_{1-6}$ aliphatic, or $OC_{1-6}$ aliphatic; and $R^5$ is H, D, F, Cl, Br, I, $C_{1-6}$ aliphatic, or $OC_{1-6}$ aliphatic;

with sodium azide, optionally in the presence of zinc chloride, to yield the compound of formula (I-a) above; or (b) cyclizing a carbonitrile of formula (II-b):

(II-b)

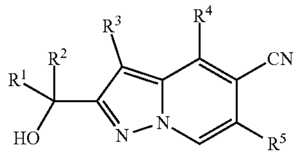

wherein:

$R^1$ is $Ar^A$ or $Hetar^A$;

$Ar^A$ is a monocyclic or bicyclic aryl;

wherein the monocyclic or bicyclic aryl contains 5, 6, 7, 8, 9, 10, or 11 ring carbon atoms; and wherein the monocyclic or bicyclic aryl is optionally substituted with one or more substituents independently selected from the group consisting of $R^{A1}$, $R^{A2}$, $R^{A3}$, $R^{A4}$, and $R^{A5}$;

$Hetar^A$ is a monocyclic or bicyclic heteroaryl;

wherein the monocyclic or bicyclic heteroaryl contains 5, 6, 7, 8, 9, 10, or 11 ring atoms;

wherein the monocyclic or bicyclic heteroaryl contains ring carbon atoms and 1, 2, 3, 4, or 5 ring heteroatoms independently selected from the group consisting of N, O, and S; and wherein the monocyclic or bicyclic heteroaryl is optionally substituted with one or more substituents independently selected from the group consisting of $R^{A1}$, $R^{A2}$, $R^{A3}$, $R^{A4}$, and $R^{A5}$;

$R^2$ is $Ar^B$ or $Hetar^B$;

$Ar^B$ is a monocyclic or bicyclic aryl;

wherein the monocyclic or bicyclic aryl contains 5, 6, 7, 8, 9, 10, or 11 ring carbon atoms; and wherein the monocyclic or bicyclic aryl is optionally substituted with one or more substituents independently selected from the group consisting of $R^{B1}$, $R^{B2}$, $R^{B3}$, $R^{B4}$, and $R^{B5}$;

$Hetar^B$ is a monocyclic or bicyclic heteroaryl;

wherein the monocyclic or bicyclic heteroaryl contains 5, 6, 7, 8, 9, 10, or 11 ring atoms;

wherein the monocyclic or bicyclic heteroaryl contains ring carbon atoms and 1, 2, 3, 4, or 5 ring heteroatoms independently selected from the group consisting of N, O, and S; and wherein the monocyclic or bicyclic heteroaryl is optionally substituted with one or more substituents independently selected from the group consisting of $R^{B1}$, $R^{B2}$, $R^{B3}$, $R^{B4}$, and $R^{B5}$;

each $R^{A1}$ is independently H, D, F, Cl, Br, I, $C_{1-6}$ aliphatic, or $OC_{1-6}$ aliphatic;

each $R^{A2}$ is independently H, D, F, Cl, Br, I, $C_{1-6}$ aliphatic, or $OC_{1-6}$ aliphatic;

each $R^{A3}$ is independently H, D, F, Cl, Br, I, $C_{1-6}$ aliphatic, or $OC_{1-6}$ aliphatic;

each $R^{A4}$ is independently H, D, F, Cl, Br, I, $C_{1-6}$ aliphatic, or $OC_{1-6}$ aliphatic;

each $R^{A5}$ is independently H, D, F, Cl, Br, I, $C_{1-6}$ aliphatic, or $OC_{1-6}$ aliphatic;

each $R^{B1}$ is independently H, D, F, Cl, Br, I, $C_{1-6}$ aliphatic, or $OC_{1-6}$ aliphatic;

each $R^{B2}$ is independently H, D, F, Cl, Br, I, $C_{1-6}$ aliphatic, or $OC_{1-6}$ aliphatic;

each $R^{B3}$ is independently H, D, F, Cl, Br, I, $C_{1-6}$ aliphatic, or $OC_{1-6}$ aliphatic;

each $R^{B4}$ is independently H, D, F, Cl, Br, I, $C_{1-6}$ aliphatic, or $OC_{1-6}$ aliphatic;

each $R^{B5}$ is independently H, D, F, Cl, Br, I, $C_{1-6}$ aliphatic, or $OC_{1-6}$ aliphatic;

$R^3$ is $C_{1-6}$ aliphatic or $OC_{1-6}$ aliphatic;

$R^4$ is H, D, $C_{1-6}$ aliphatic, or $OC_{1-6}$ aliphatic; and $R^5$ is H, D, F, Cl, Br, I, $C_{1-6}$ aliphatic, or $OC_{1-6}$ aliphatic;

with sodium azide, optionally in the presence of zinc chloride, to yield the compound of formula (I-b) above; or (c) cyclizing a carbonitrile of formula (II-c):

(II-c)

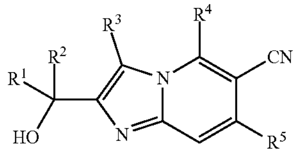

wherein:

$R^1$ is $Ar^A$ or $Hetar^A$;

$Ar^A$ is a monocyclic or bicyclic aryl;

wherein the monocyclic or bicyclic aryl contains 5, 6, 7, 8, 9, 10, or 11 ring carbon atoms; and wherein the monocyclic or bicyclic aryl is optionally substituted with one or more substituents independently selected from the group consisting of $R^{A1}$, $R^{A2}$, $R^{A3}$, $R^{A4}$, and $R^{A5}$;

$Hetar^A$ is a monocyclic or bicyclic heteroaryl;

wherein the monocyclic or bicyclic heteroaryl contains 5, 6, 7, 8, 9, 10, or 11 ring atoms;

wherein the monocyclic or bicyclic heteroaryl contains ring carbon atoms and 1, 2, 3, 4, or 5 ring heteroatoms independently selected from the group consisting of N, O, and S; and wherein the monocyclic or bicyclic heteroaryl is optionally substituted with one or more substituents independently selected from the group consisting of $R^{A1}$, $R^{A2}$, $R^{A3}$, $R^{A4}$, and $R^{A5}$;

$R^2$ is $Ar^B$ or $Hetar^B$;

$Ar^B$ is a monocyclic or bicyclic aryl;

wherein the monocyclic or bicyclic aryl contains 5, 6, 7, 8, 9, 10, or 11 ring carbon atoms; and wherein the monocyclic or bicyclic aryl is optionally substituted with one or more substituents independently selected from the group consisting of $R^{B1}$, $R^{B2}$, $R^{B3}$, $R^{B4}$, and $R^{B5}$;

$Hetar^B$ is a monocyclic or bicyclic heteroaryl;

wherein the monocyclic or bicyclic heteroaryl contains 5, 6, 7, 8, 9, 10, or 11 ring atoms;

wherein the monocyclic or bicyclic heteroaryl contains ring carbon atoms and 1, 2, 3, 4, or 5 ring heteroatoms independently selected from the group consisting of N, O, and S; and wherein the monocyclic or bicyclic heteroaryl is optionally substituted with one or more substituents independently selected from the group consisting of $R^{B1}$, $R^{B2}$, $R^{B3}$, $R^{B4}$, and $R^{B5}$;

each $R^{A1}$ is independently H, D, F, Cl, Br, I, $C_{1-6}$ aliphatic, or $OC_{1-6}$ aliphatic;

each $R^{A2}$ is independently H, D, F, Cl, Br, I, $C_{1-6}$ aliphatic, or $OC_{1-6}$ aliphatic;

each $R^{A3}$ is independently H, D, F, Cl, Br, I, $C_{1-6}$ aliphatic, or $OC_{1-6}$ aliphatic;

each $R^{A4}$ is independently H, D, F, Cl, Br, I, $C_{1-6}$ aliphatic, or $OC_{1-6}$ aliphatic;
each $R^{A5}$ is independently H, D, F, Cl, Br, I, $C_{1-6}$ aliphatic, or $OC_{1-6}$ aliphatic;
each $R^{B1}$ is independently H, D, F, Cl, Br, I, $C_{1-6}$ aliphatic, or $OC_{1-6}$ aliphatic;
each $R^{B2}$ is independently H, D, F, Cl, Br, I, $C_{1-6}$ aliphatic, or $OC_{1-6}$ aliphatic;
each $R^{B3}$ is independently H, D, F, Cl, Br, I, $C_{1-6}$ aliphatic, or $OC_{1-6}$ aliphatic;
each $R^{B4}$ is independently H, D, F, Cl, Br, I, $C_{1-6}$ aliphatic, or $OC_{1-6}$ aliphatic;
each $R^{B5}$ is independently H, D, F, Cl, Br, I, $C_{1-6}$ aliphatic, or $OC_{1-6}$ aliphatic;
$R^3$ is $C_{1-6}$ aliphatic or $OC_{1-6}$ aliphatic;
$R^4$ is H, D, $C_{1-6}$ aliphatic, or $OC_{1-6}$ aliphatic; and
$R^5$ is H, D, F, Cl, Br, I, $C_{1-6}$ aliphatic, or $OC_{1-6}$ aliphatic;

with sodium azide, optionally in the presence of zinc chloride, to yield the compound of formula (I-c) above.

25. A compound of formula (II-a), formula (II-b), or formula (II-c):

(II-a)

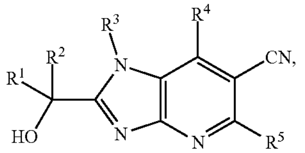

(II-b)

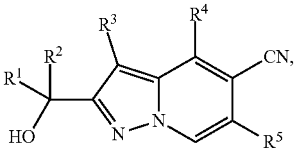

(II-c)

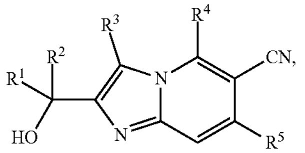

or a pharmaceutically acceptable salt, deuteroisotope, stereoisomer, or tautomer thereof, wherein:
$R^1$ is $Ar^A$ or $Hetar^A$;
$Ar^A$ is a monocyclic or bicyclic aryl;
wherein the monocyclic or bicyclic aryl contains 5, 6, 7, 8, 9, 10, or 11 ring carbon atoms; and
wherein the monocyclic or bicyclic aryl is optionally substituted with one or more substituents independently selected from the group consisting of $R^{A1}$, $R^{A2}$, $R^{A3}$, $R^{A4}$, and $R^{A5}$;
$Hetar^A$ is a monocyclic or bicyclic heteroaryl;
wherein the monocyclic or bicyclic heteroaryl contains 5, 6, 7, 8, 9, 10, or 11 ring atoms;
wherein the monocyclic or bicyclic heteroaryl contains ring carbon atoms and 1, 2, 3, 4, or 5 ring heteroatoms independently selected from the group consisting of N, O, and S; and
wherein the monocyclic or bicyclic heteroaryl is optionally substituted with one or more substituents independently selected from the group consisting of $R^{A1}$, $R^{A2}$, $R^{A3}$, $R^{A4}$, and $R^{A5}$;
$R^2$ is $Ar^B$ or $Hetar^B$;
$Ar^B$ is a monocyclic or bicyclic aryl;
wherein the monocyclic or bicyclic aryl contains 5, 6, 7, 8, 9, 10, or 11 ring carbon atoms; and
wherein the monocyclic or bicyclic aryl is optionally substituted with one or more substituents independently selected from the group consisting of $R^{B1}$, $R^{B2}$, $R^{B3}$, $R^{B4}$, and $R^{B5}$;
$Hetar^B$ is a monocyclic or bicyclic heteroaryl;
wherein the monocyclic or bicyclic heteroaryl contains 5, 6, 7, 8, 9, 10, or 11 ring atoms;
wherein the monocyclic or bicyclic heteroaryl contains ring carbon atoms and 1, 2, 3, 4, or 5 ring heteroatoms independently selected from the group consisting of N, O, and S; and
wherein the monocyclic or bicyclic heteroaryl is optionally substituted with one or more substituents independently selected from the group consisting of $R^{B1}$, $R^{B2}$, $R^{B3}$, $R^{B4}$, and $R^{B5}$;
each $R^{A1}$ is independently H, D, F, Cl, Br, I, $C_{1-6}$ aliphatic, or $OC_{1-6}$ aliphatic;
each $R^{A2}$ is independently H, D, F, Cl, Br, I, $C_{1-6}$ aliphatic, or $OC_{1-6}$ aliphatic;
each $R^{A3}$ is independently H, D, F, Cl, Br, I, $C_{1-6}$ aliphatic, or $OC_{1-6}$ aliphatic;
each $R^{A4}$ is independently H, D, F, Cl, Br, I, $C_{1-6}$ aliphatic, or $OC_{1-6}$ aliphatic;
each $R^{A5}$ is independently H, D, F, Cl, Br, I, $C_{1-6}$ aliphatic, or $OC_{1-6}$ aliphatic;
each $R^{B1}$ is independently H, D, F, Cl, Br, I, $C_{1-6}$ aliphatic, or $OC_{1-6}$ aliphatic;
each $R^{B2}$ is independently H, D, F, Cl, Br, I, $C_{1-6}$ aliphatic, or $OC_{1-6}$ aliphatic;
each $R^{B3}$ is independently H, D, F, Cl, Br, I, $C_{1-6}$ aliphatic, or $OC_{1-6}$ aliphatic;
each $R^{B4}$ is independently H, D, F, Cl, Br, I, $C_{1-6}$ aliphatic, or $OC_{1-6}$ aliphatic;
each $R^{B5}$ is independently H, D, F, Cl, Br, I, $C_{1-6}$ aliphatic, or $OC_{1-6}$ aliphatic;
$R^3$ is $C_{1-6}$ aliphatic or $OC_{1-6}$ aliphatic, wherein the $C_{1-6}$ aliphatic or $OC_{1-6}$ aliphatic is optionally substituted with one or more substituents independently selected from the group consisting of $NH_2$ and OH;
$R^4$ is H, D, $C_{1-6}$ aliphatic, or $OC_{1-6}$ aliphatic; and
$R^5$ is H, D, F, Cl, Br, I, $C_{1-6}$ aliphatic, or $OC_{1-6}$ aliphatic.

26. A compound selected from the group consisting of:

1

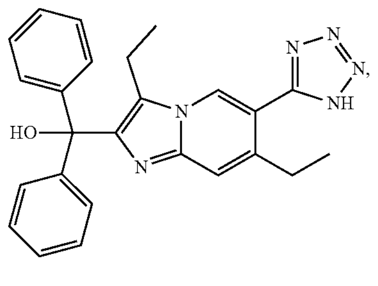

-continued
2
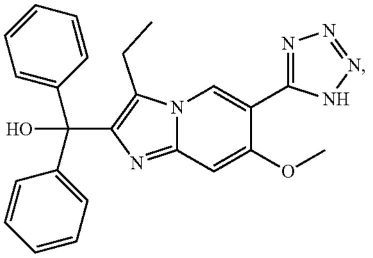
3
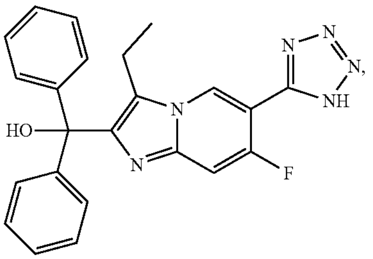
4
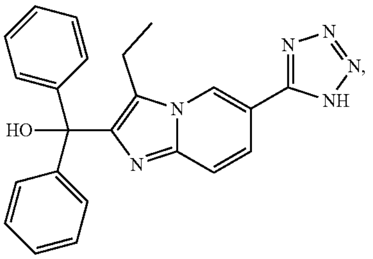
5
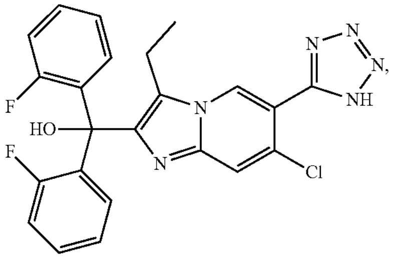
6
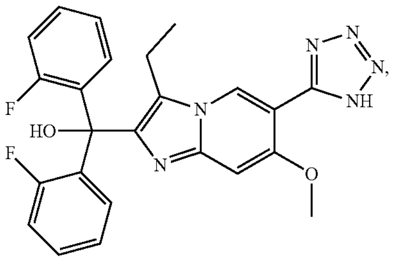
7
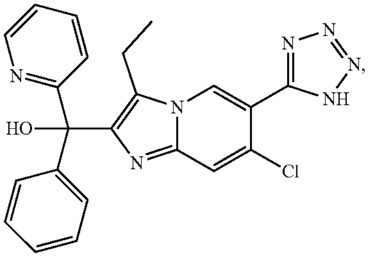
-continued
8
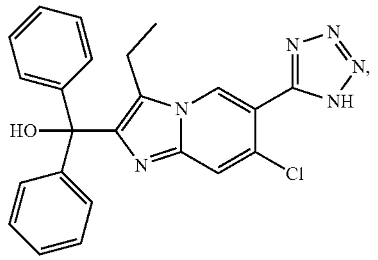
9
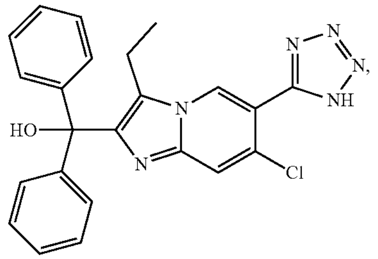
10
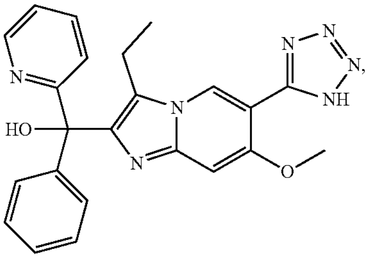
11
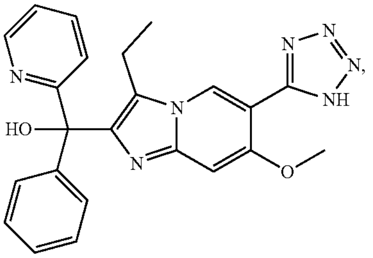
12
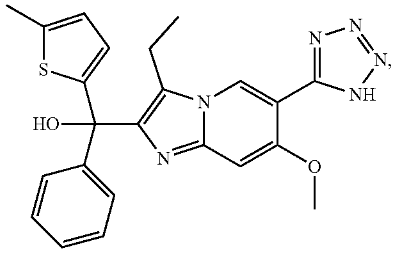
13
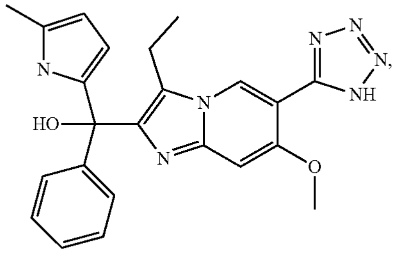

-continued
14
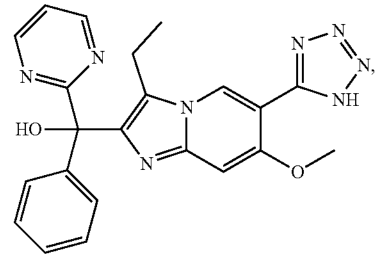
15
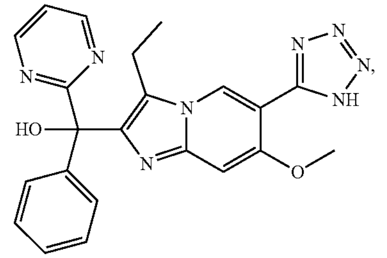
16
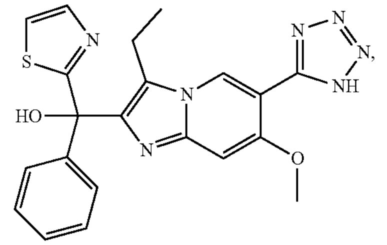
17
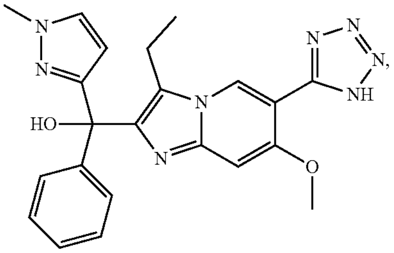
18
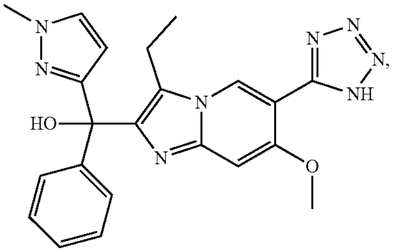
19
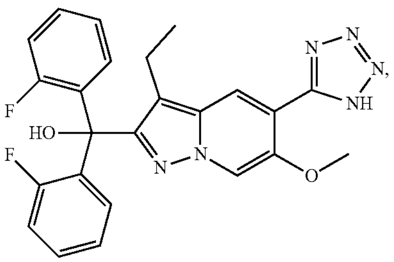
-continued
20
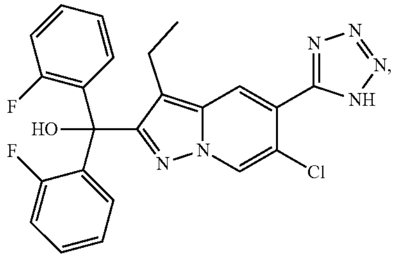
21
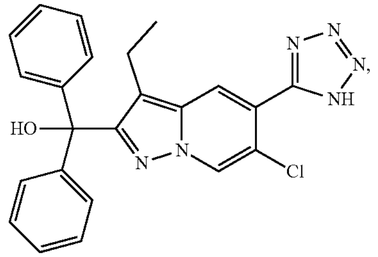
22
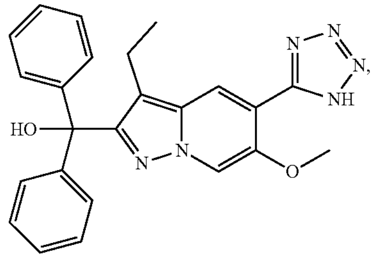
23
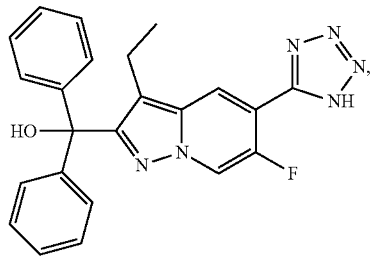
24
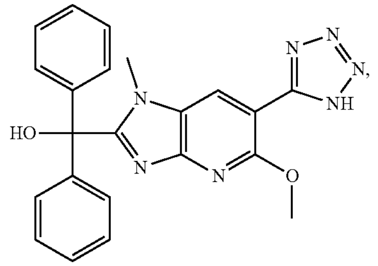
25
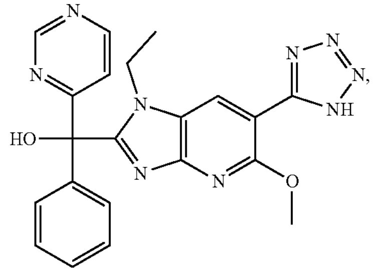

-continued
26
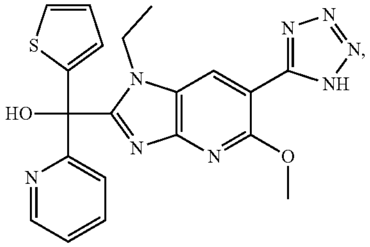
27
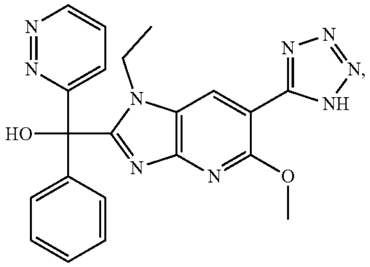
28
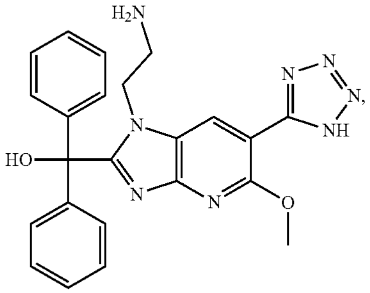
29
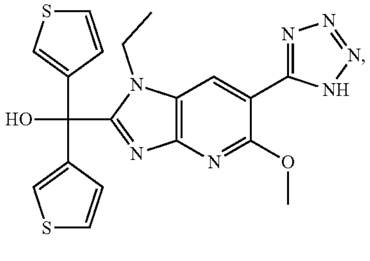
30
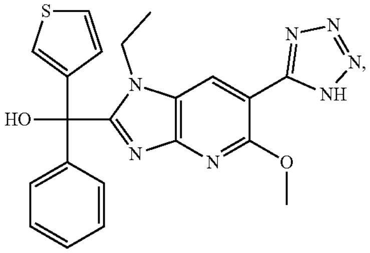
-continued
31
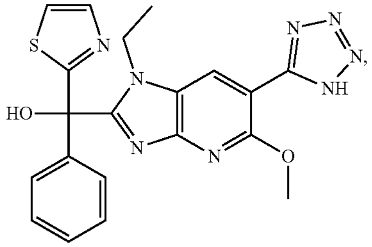
32
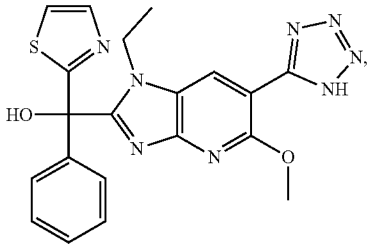
33
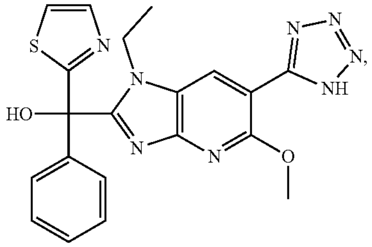
34
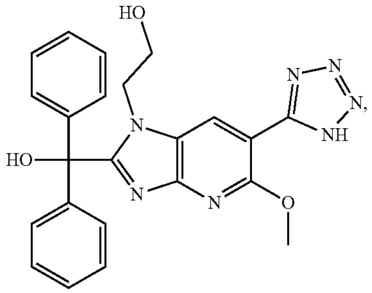
35
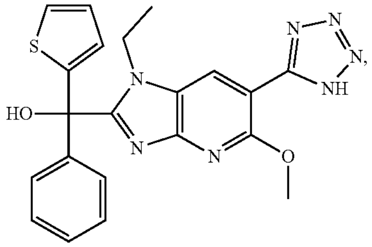
36
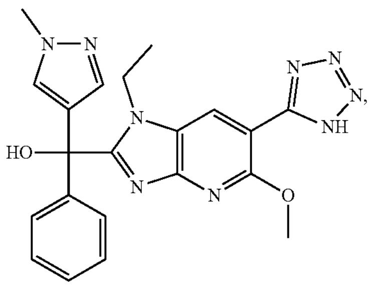

-continued
37
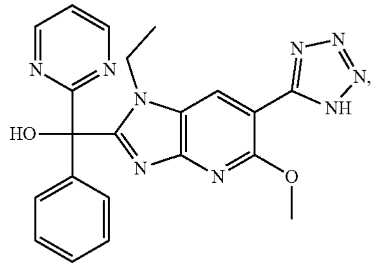
38
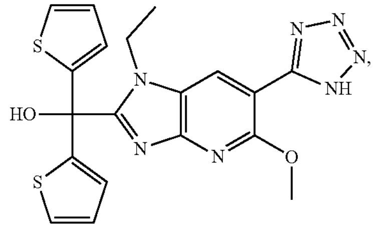
39
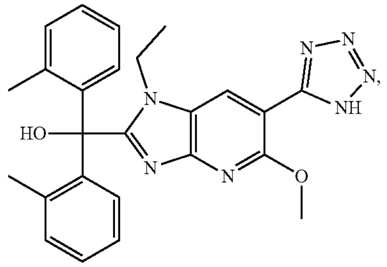
40
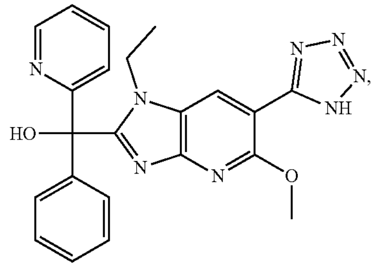
41
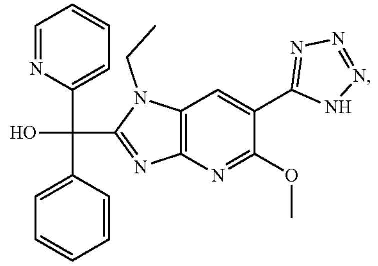
42
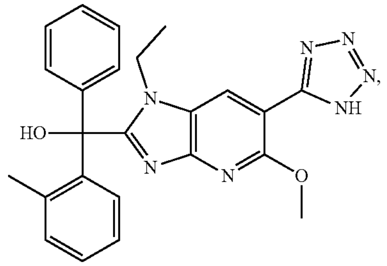
-continued
43
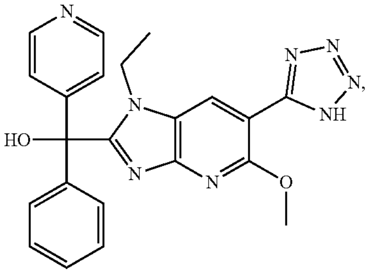
44
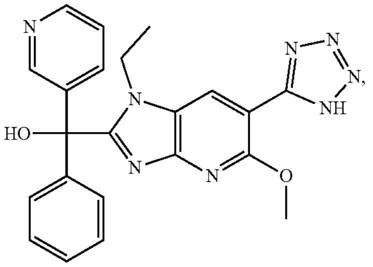
45
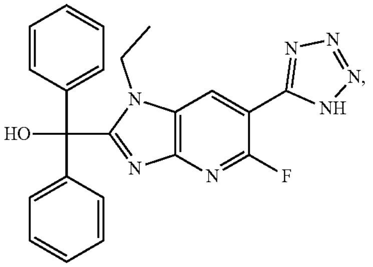
46
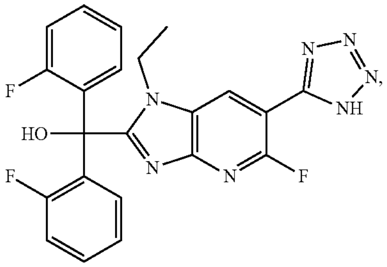
47
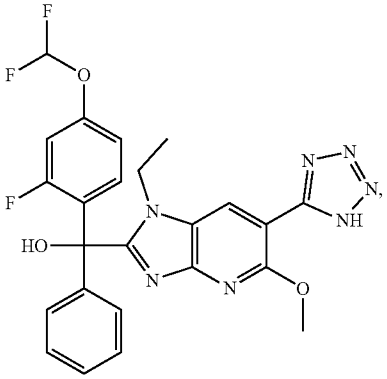

-continued
48
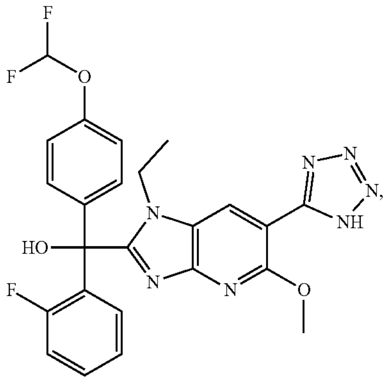
49
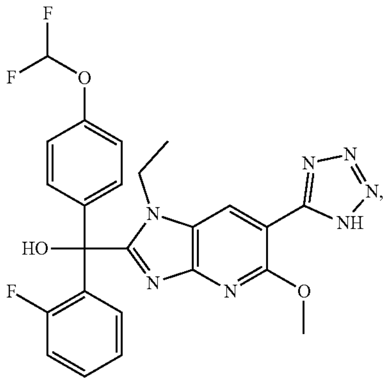
50
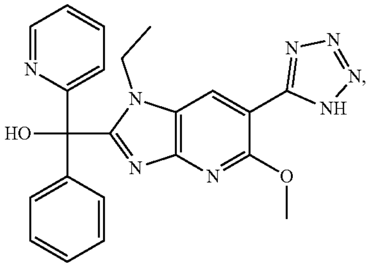
51
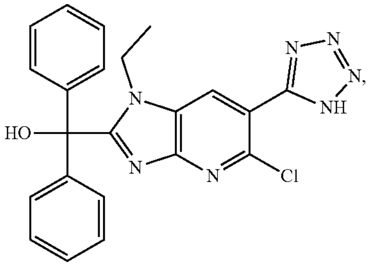
-continued
52
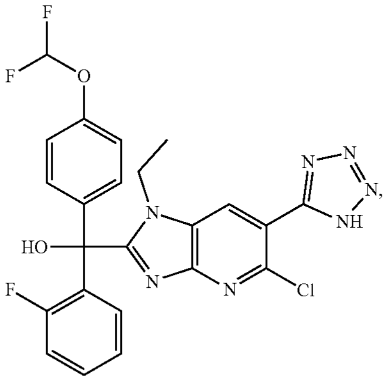
53
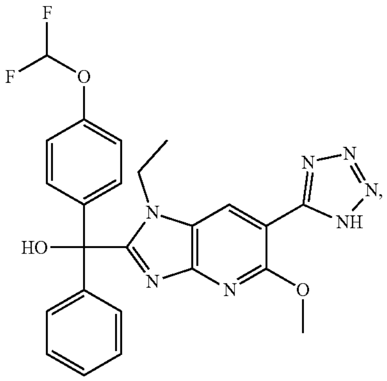
54
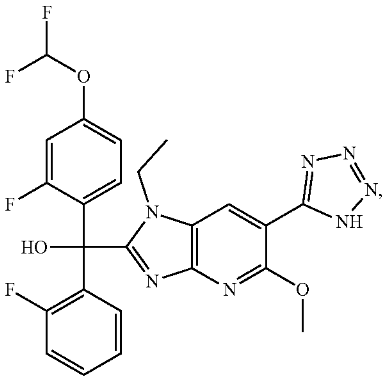
55
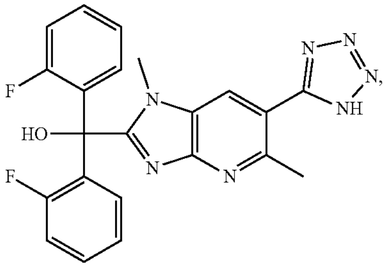

-continued
56
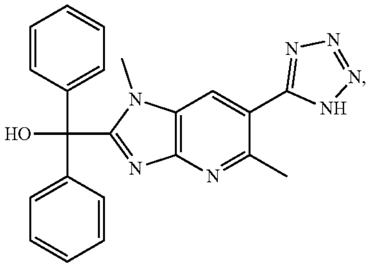
57
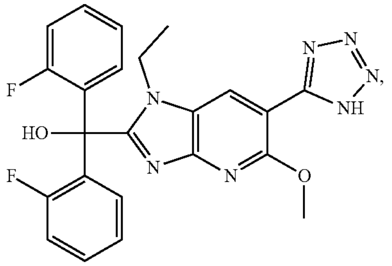
58
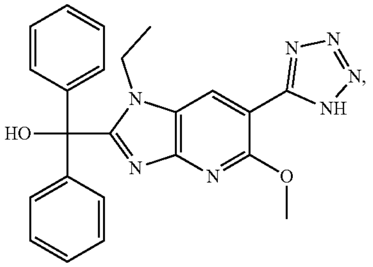
59
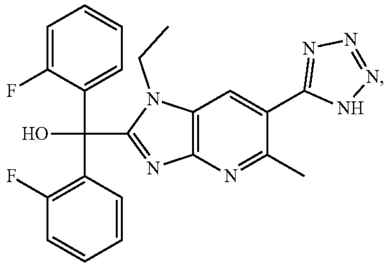
-continued
60
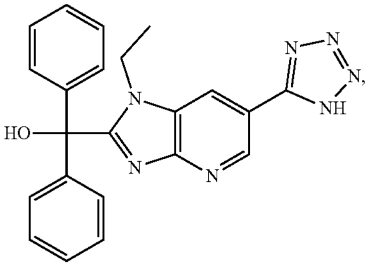
61
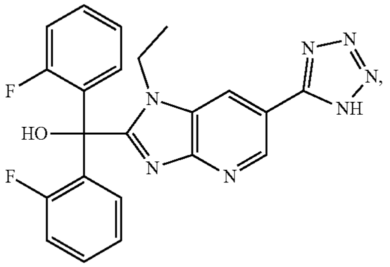
62
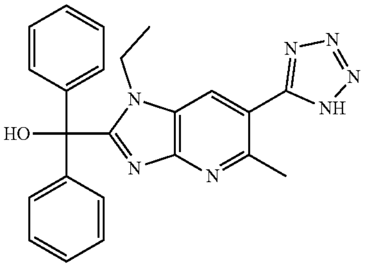
and
63
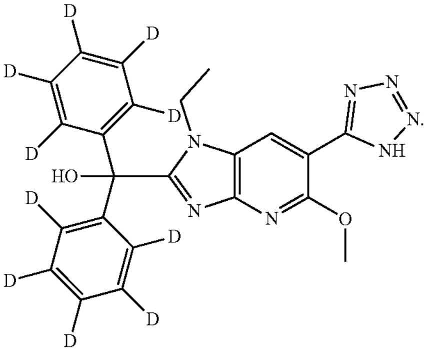
or a pharmaceutically acceptable salt, deuteroisotope, stereoisomer, or tautomer thereof.
* * * * *